(12) United States Patent
deJesus et al.

(10) Patent No.: US 10,513,518 B2
(45) Date of Patent: Dec. 24, 2019

(54) INHIBITORS OF THE RENAL OUTER MEDULLARY POTASSIUM CHANNEL

(71) Applicant: Merck Sharp & Dohme Corp., Rahway, NJ (US)

(72) Inventors: Reynalda K. deJesus, East Brunswick, NJ (US); Qinghong Fu, Plainsboro, NJ (US); Jinlong Jiang, Scotch Plains, NJ (US); Haifeng Tang, Metuchen, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/544,295

(22) PCT Filed: Jan. 25, 2016

(86) PCT No.: PCT/US2016/014664
§ 371 (c)(1),
(2) Date: Jul. 18, 2017

(87) PCT Pub. No.: WO2016/122994
PCT Pub. Date: Aug. 4, 2016

(65) Prior Publication Data
US 2018/0009807 A1 Jan. 11, 2018

Related U.S. Application Data

(60) Provisional application No. 62/109,232, filed on Jan. 29, 2015.

(51) Int. Cl.
| | | |
|---|---|---|
| *A61K 31/435* | (2006.01) |
| *A61K 31/55* | (2006.01) |
| *A61K 31/5386* | (2006.01) |
| *A61K 31/424* | (2006.01) |
| *C07D 471/10* | (2006.01) |
| *C07D 487/10* | (2006.01) |
| *C07D 498/10* | (2006.01) |
| *A61K 31/401* | (2006.01) |
| *A61K 31/41* | (2006.01) |
| *A61K 31/4178* | (2006.01) |
| *A61K 31/4184* | (2006.01) |
| *A61K 31/439* | (2006.01) |
| *A61K 31/4422* | (2006.01) |
| *A61K 31/4523* | (2006.01) |
| *A61K 31/5377* | (2006.01) |
| *C07D 471/20* | (2006.01) |
| *A61K 31/444* | (2006.01) |

(Continued)

(52) U.S. Cl.
CPC .......... *C07D 471/10* (2013.01); *A61K 31/401* (2013.01); *A61K 31/41* (2013.01); *A61K 31/4178* (2013.01); *A61K 31/4184* (2013.01); *A61K 31/435* (2013.01); *A61K 31/439* (2013.01); *A61K 31/444* (2013.01); *A61K 31/4422* (2013.01); *A61K 31/4523* (2013.01); *A61K 31/46* (2013.01); *A61K 31/5377* (2013.01); *A61K 31/5386* (2013.01); *A61K 31/55* (2013.01); *A61K 45/06* (2013.01); *C07D 451/00* (2013.01); *C07D 471/20* (2013.01); *C07D 487/10* (2013.01); *C07D 498/10* (2013.01)

(58) Field of Classification Search
CPC .. C07D 471/10; C07D 487/10; C07D 498/10; A61K 31/435; A61K 31/55; A61K 31/5386; A61K 31/424
USPC ........ 546/16, 19; 548/410, 409, 216; 544/70; 514/278, 212.02, 409, 374, 231.2
See application file for complete search history.

(56) References Cited

U.S. PATENT DOCUMENTS 9,839,629 B2 * 12/2017 Dong .................. C07D 519/00

FOREIGN PATENT DOCUMENTS

| EP | 2218788 A1 | 8/2010 |
| WO | 2010129379 A1 | 11/2010 |

(Continued)

OTHER PUBLICATIONS

Sheridan, Robert, "The Most Common Chemical Replacements in Drug-Like Compounds" J. Chem. Inf. Comp. Sci. (2002), 42: pp. 103-108. (Year: 2002).*

(Continued)

*Primary Examiner* — Matthew P Coughlin
*Assistant Examiner* — Sagar Patel
(74) *Attorney, Agent, or Firm* — Sarah L. Hooson; Catherine D. Fitch

(57) ABSTRACT

The present invention provides compounds of Formula I (I) and the pharmaceutically acceptable salts thereof, which are inhibitors of the ROMK (Kir1.1) channel. The compounds may be used as diuretic and/or natriuretic agents and for the therapy and prophylaxis of medical conditions including cardiovascular diseases such as hypertension, heart failure and chronic kidney disease and conditions associated with excessive salt and water retention.

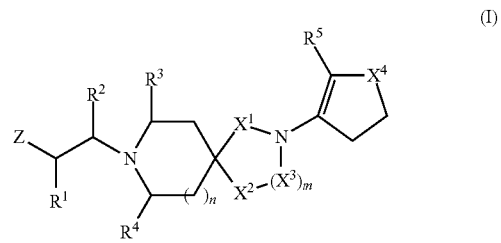

13 Claims, No Drawings

(51) Int. Cl.
*A61K 31/46* (2006.01)
*A61K 45/06* (2006.01)
*C07D 451/00* (2006.01)

(56) References Cited

FOREIGN PATENT DOCUMENTS

| WO | 2012058116 | A1 | | 5/2012 | | |
|----|------------|----|---|--------|---|---|
| WO | 2012058134 | A1 | | 5/2012 | | |
| WO | 2013028474 | A1 | | 2/2013 | | |
| WO | 2013039802 | A1 | | 3/2013 | | |
| WO | 2013062892 | A1 | | 5/2013 | | |
| WO | 2013062900 | A1 | | 5/2013 | | |
| WO | 2013066714 | A1 | | 5/2013 | | |
| WO | 2013066717 | A1 | | 5/2013 | | |
| WO | 2013066718 | A2 | | 5/2013 | | |
| WO | 2013090271 | A1 | | 6/2013 | | |
| WO | 2014015495 | A1 | | 1/2014 | | |
| WO | 2014018764 | A1 | * | 1/2014 | ........... | A61K 31/435 |
| WO | 2014018764 | A1 | | 1/2014 | | |
| WO | 2014085210 | A1 | | 6/2014 | | |
| WO | 2014099633 | A2 | | 6/2014 | | |
| WO | 2014126944 | A2 | | 8/2014 | | |
| WO | 2014150132 | A1 | | 9/2014 | | |
| WO | 2015100147 | A1 | * | 7/2015 | ........... | C07D 519/00 |
| WO | WO2016122994 | A1 | | 8/2016 | | |

OTHER PUBLICATIONS

Bhave, G., Development of a selective small-molecule inhibitor Kir1.1, the renal outer medullary potassium channel, Mol. Pharmacol., 2011, 42-50, 79.

Hebert, S. C. et al., Molecular Diversity and Regulation of Renal Potassium Channels, Physiol Rev., 2005, p. 319-371, vol. 85.

Ho, K. et al., Cloning and expression of an inwardly rectifying ATP-regulated potassium channel, Nature, 1993, p. 31-38, vol. 362.

International Search Report and Written Opinion for PCT/US2016/014664 dated Apr. 21, 2016; 9 pages.

Ji, W. et al., Rare independent mutations in renal salt handling genes contribute to blood pressure variation, Nature Genetics, 2008, p. 592-599, vol. 40, No. 5.

Lewis, L M., High-throughput screening reveals a small-molecule inhibitor of the Renal Outer Medullary Potassium Channel and Kir7.1, Mol. Phamcol., 2009, 1094-1103, 76.

Lifton, R. P. et al., Molecular Mechanisms of Human Hypertension, Cell, 2001, p. 545-556, vol. 104.

Lorenz, J. N. et al., Impaired Renal NaCl Absorption inMic Lacking the ROMK Potassium Cannel, a Model for Type II Bartter's Syndrome, The Journal of Biological Chemistry, 2002, p. 37871-37880, vol. 277, No. 40.

Lu, M. et al., Absence of Small Conductance K+ Channel (SK) Activity in Apical Membranes of Thick Ascending Limb and Cortical Collectiong Duct in ROMK (Bartter's) Knockout Mice, The Journal of Biological Chemistry, 2002, p. 37881-37887, vol. 277, No. 40.

Molander, G. A. et al., Stereoselective Suzuki-Miyaura Cross-Coupling Reactions of Potassium Alkenyltrifluoroborates with Alkenyl Bromides, J. Org. Chem, 2005, p. 3950-3956, vol. 70.

Nomura, Y. et al., Synthesis and Structure-Activity Relationships of 2-(4-Benzhydryl-1-piperazinyl)-1-phenylethanols as New Calcium Blockers, Chem. Phar. Bull, 1995, p. 241-246, vol. 43, No. 2.

Reinalter, S. C. et al., Pharmacotyping of hypokalaemic salt-losing tubular disorders, Acta Physiol Scand, 2004, p. 513-521, vol. 181.

Shuck, M. E et al., Cloning and Characterization of Multiple Forms of the Human Kidney ROM-K Potassium Channel, The Journal of Biological Chemistry, 1994, p. 24261-24270, Vo. 269, No. 39.

Tobin, M. D. et al., Common Variants in Genes Underlying Monogenic Hypertension and Hypotension and Blood Pressure in the General Population, Hypertension, 2008, p. 1658-1664, vol. 51, No. 6.

Wang, W. et al., Renal potassium channesl: recent developments, Current Opinion in Nephrology and Hypertension, 2004, p. 549-555, vol. 13, No. 5.

* cited by examiner

INHIBITORS OF THE RENAL OUTER MEDULLARY POTASSIUM CHANNEL

CROSS-REFERENCE TO RELATED APPLICATIONS

This application is a U.S. National Phase application under 35 U.S.C. § 371 of PCT Application No. PCT/US2016/014664, filed on Jan. 25, 2016, which claims priority from and the benefit of U.S. Provisional Application Ser. No. 62/109,232, filed Jan. 29, 2015.

FIELD OF THE INVENTION

The present invention relates to novel spirocyclic compounds and salts thereof useful as renal outer medullary potassium channel inhibitors. The present invention further relates to compositions containing such compounds, and methods of use thereof.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the Na+/K+/2Cl⁻ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are expected to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first publicly disclosed small molecule selective inhibitors of ROMK, including VU590, were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. The compound VU591 was later reported in Bhave, G. et al., *Development of a Selective Small-Molecule Inhibitor of Kir1.1, the Renal Outer Medullary Potassium Channel*, Mol Pharmacol, 2011, 79(1), p. 42-50, the text of which states that "ROMK (Kir1.1), is a putative drug target for a novel class of loop diuretics that would lower blood pressure without causing hypokalemia."

Since then, other ROMK inhibitors have been described in WO2013/028474, WO2010/129379, WO2012/058134, WO2014/085210, WO2012/058116, WO2013/039802, WO2013/090271, WO2014/099633, WO2013/062892, WO2013/062900, WO2013/066714, WO2013/066717, WO2013/066718, WO 2014/015495, WO2014/018764, WO2014/126944 and WO2014/150132.

The continued discovery of selective small molecule inhibitors of ROMK is needed for the development of new treatments for hypertension, heart failure, edematous states and related disorders. The compounds of Formula I and salts thereof of this invention are selective inhibitors of the ROMK channel and could be used for the treatment of hypertension, heart failure and other conditions where treatment with a diuretic or natriuretic would be beneficial.

SUMMARY OF THE INVENTION

The present invention provides compounds of Formula I

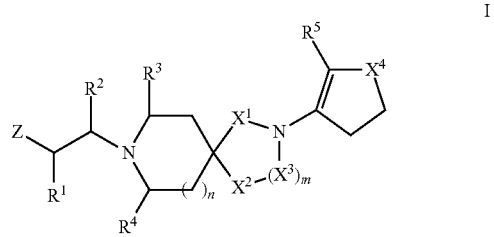

and pharmaceutically acceptable salts thereof. The compounds of Formula I are inhibitors of the ROMK (Kir1.1) channel. As a result, the compounds of Formula I could be used in methods of treatment, inhibition or amelioration of one or more disease states that could benefit from inhibition of ROMK. The compounds of this invention could be used in methods of treatment which comprise administering a therapeutically or prophylactically effective amount of a compound of Formula I to a patient in need of a diuretic and/or natriuretic agent. Therefore, the compounds of Formula I could be valuable pharmaceutically active compounds for the therapy, prophylaxis or both of medical conditions, including, but not limited to, cardiovascular diseases such as hypertension and heart failure as well as chronic kidney disease, and conditions associated with excessive salt and water retention. The compounds of this invention could further be used in combination with other therapeutically effective agents, including but not limited to, other drugs which are useful for the treatment of hypertension, heart failure and conditions associated with excessive salt and water retention. The invention furthermore relates to processes for preparing compounds of Formula I, and pharmaceutical compositions which comprise compounds of Formula I. These and other aspects of the invention will be evident from the description contained herein.

DETAILED DESCRIPTION OF THE INVENTION

The present invention addresses the following compounds, compounds of having structural Formula I:

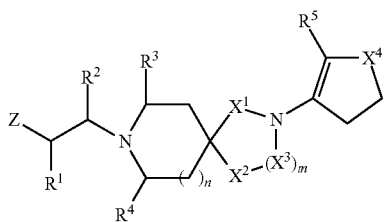

I or a pharmaceutically acceptable salt thereof wherein:
$R^1$ is —H, halo, —OH, —$C_{1-3}$alkyl or —$OC_{1-3}$alkyl;
$R^2$ is —H, or $C_{1-4}$alkyl;
$R^3$ is —H, or —$C_{1-3}$alkyl optionally substituted with —OH, —$OCH_3$ or 1 to 3 halo, or $R^3$ and $R^4$ are joined together to form —$CH_2$—$CH_2$—;
$R^4$ is —H, or —$C_{1-3}$alkyl optionally substituted with —OH, —$OCH_3$ or 1 to 3 halo, or $R^3$ and $R^4$ are joined together to form —$CH_2$—$CH_2$—;
n is 1 or 2;
m is 1 or 2, wherein when m is 2, $X^3$ is —$CH_2$—;
$R^5$ is —H, halo, —$C_{3-6}$cycloalkyl or —$C_{1-3}$alkyl;
$X^1$ is —C(O)— or —$CH_2$—;
$X^2$ is —O— or —$CH_2$—;
$X^3$ is —C(O)— or —$CH_2$—, wherein when $X^3$ is —$CH_2$—, m is 2;
$X^4$ is —C(O)— or —$SO_2$—;
Z is

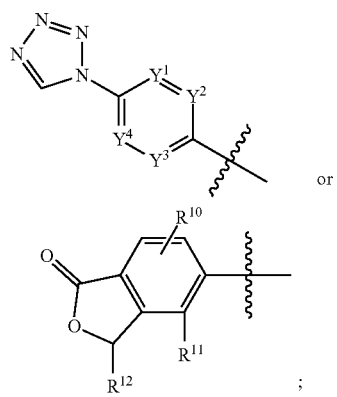

or

;

$Y^1$, $Y^2$, and $Y^4$ are each independently $C(R^9)$ or N;
provided that at most two of $Y^1$, $Y^2$, $Y^3$ and $Y^4$ are N;
each $R^9$ is independently —H, halo, $OC_{1-4}$alkyl or $C_{1-4}$alkyl optionally substituted with 1 to 3 halo;
$R^{10}$ is —H, halo, or $C_{1-4}$alkyl optionally substituted with 1 to 3 halo;

$R^{11}$ is —H, $C_{1-4}$alkyl optionally substituted with 1 to 3 halo; and
$R^{12}$ is —H or $C_{1-4}$alkyl.

With respect to the compounds described herein, $R^1$ is —H, halo, —OH, —$C_{1-3}$alkyl or —$OC_{1-3}$alkyl. In certain embodiments, $R^1$ is —H. In other embodiments, $R^1$ is halogen. Suitable halogens include, but are not limited to, fluorine, chlorine, bromine and iodine. In still other embodiments, $R^1$ is —OH. In yet other embodiments, $R^1$ is —$C_{1-3}$alkyl. Suitable examples of —$C_{1-3}$alkyls include, but are not limited to, methyl, ethyl or propyl. In still other embodiments, $R^1$ is —$OC_{1-3}$alkyl. Suitable examples of —$OC_{1-3}$alkyl include, but are not limited to, methoxy, ethoxy or propoxy.

With respect to the compounds described herein, $R^2$ is —H or —$C_{1-4}$alkyl. In certain embodiments, $R^2$ is —H. In other embodiments, $R^2$ is —$C_{1-4}$alkyl. Suitable examples of —$C_{1-4}$alkyl include, but are not limited to, methyl, ethyl, propyl or butyl.

With respect to the compounds described herein, $R^3$ is —H, or —$C_{1-3}$alkyl optionally substituted with —OH, —$OCH_3$ or 1 to 3 of halo, or $R^3$ and $R^4$ are joined together to form —$CH_2$—$CH_2$—. In certain embodiments, $R^3$ is —H. In other embodiments, $R^3$—$C_{1-3}$alkyl. Suitable —$C_{1-3}$alkyls include, but are not limited to, methyl, ethyl and propyl. In certain embodiments, when $R^3$ is —$C_{1-3}$alkyl, the —$C_{1-3}$alkyl is unsubstituted. In other embodiments, when $R^3$ is —$C_{1-3}$alkyl, the —$C_{1-3}$alkyl is substituted. For example, —$C_{1-3}$alkyl can be substituted with —OH, —$OCH_3$ or 1, 2 or 3 halogens. Suitable halogens include, but are not limited to, fluorine, chlorine, bromine and iodine.

With respect to the compounds described herein, $R^4$ is —H, or —$C_{1-3}$alkyl optionally substituted with —OH, —$OCH_3$ or 1 to 3 halogens, or $R^3$ and $R^4$ are joined together to form —$CH_2$—$CH_2$—. In certain embodiments, $R^4$ is —H. In other embodiments, $R^4$ is —$C_{1-3}$alkyl. Suitable —$C_{1-3}$alkyls include, but are not limited to, methyl, ethyl and propyl. In certain embodiments, when $R^4$ is —$C_{1-3}$alkyl, the —$C_{1-3}$alkyl is unsubstituted. In other embodiments, when $R^4$ is —$C_{1-3}$alkyl, the —$C_{1-3}$alkyl is substituted. For example, —$C_{1-3}$alkyl can be substituted with —OH, —$OCH_3$ or 1 to 3 halogens. Suitable halogens include, but are not limited to, fluorine, chlorine, bromine and iodine.

In certain embodiments of the compounds described herein, $R^3$ and $R^4$ are joined together to form —$CH_2CH_2$—.

In one embodiment of the compounds described herein, each of $R^3$ and $R^4$ are —H, or $R^3$ and $R^4$ are joined together to form —$CH_2CH_2$—.

With respect to the compounds described herein, n is 1 or 2. In certain embodiments, n is 1. In other embodiments, n is 2.

With respect to the compounds described herein, m is 1 or 2. In certain embodiments, m is 1. In other embodiments, m is 2. In certain embodiments, m is 2 when $X^3$ is —$CH_2$—. In other embodiments, m is 2 only when $X^2$ is —O—. In other embodiments, m is 2 when $X^1$ is —C(O)—. In still other embodiments, m is 2 when $X^2$ is —O— and $X^1$ is —C(O)—. In still other embodiments, m is 2 when $X^2$ is —O— or $X^1$ is —C(O)—. In still other embodiments, m is 2 when $X^3$ is —$CH_2$— and $X^2$ is —O— or $X^1$ is —C(O)—.

With respect to the compounds described herein, $R^5$ is —H, halo, —$C_{3-6}$cycloalkyl or —$C_{1-3}$alkyl. In certain embodiments, $R^5$ is —H. In other embodiments, $R^5$ is halogen. Suitable halogens include, but are not limited to, fluorine, chlorine, bromine and iodine. In still other embodiments, $R^5$ is —$C_{3-6}$cycloalkyl. Suitable —$C_{3-6}$cycloalkyls include, but are not limited to, cyclopropyl, cyclobutyl, cyclopentyl and cyclohexyl. In yet other embodiments, $R^1$ is —$C_{1-3}$alkyl. Suitable examples of —$C_{1-3}$alkyl include, but are not limited to, methyl, ethyl or propyl. In one embodiment of the compounds described herein, $R^5$ is —H or —$CH_3$. In another embodiment of the compounds described herein, $R^5$ is —$CH_3$.

With respect to the compounds described herein, $X^1$ is —C(O)— or —$CH_2$—. In certain embodiments of the compounds described herein, $X^1$ is —C(O)—. In other embodiments of the compounds described herein, $X^1$ is —$CH_2$—.

With respect to the compounds described herein, $X^2$ is —O— or —$CH_2$—. In certain embodiments of the compounds described herein, $X^2$ is —O—. In other embodiments of the compounds described herein, $X^2$ is —$CH_2$—.

With respect to the compounds described herein, $X^3$ is —C(O)— or —$CH_2$—. In certain embodiments, $X^3$ is —C(O)—. In other embodiments, $X^3$ is —$CH_2$—. In certain embodiments, $X^3$ is —C(O)— or —$CH_2$— when m is 1. In yet other embodiments, $X^3$ is —$CH_2$— when m is 2. In certain embodiments of the compounds described herein, $X^3$ is —C(O)— and m is 1. In other embodiments of the compounds described herein, $X^3$ is —$CH_2$— and m is 1. In other embodiments of the compounds described herein, $X^3$ is —$CH_2$— and m is 2.

With respect to the compounds described herein, $X^4$ is —C(O) or —$SO_2$—. In certain embodiments of the compounds described herein, $X^4$ is —C(O)—. In other embodiments of the compounds described herein, $X^4$ is —$SO_2$—.

In certain embodiments of the compounds described herein, $X^1$ is —C(O)— and $X^2$ is —$CH_2$—. Additionally, in such an embodiment, n can be 1.

In other embodiments of the compounds described herein, $X^1$ is —$CH_2$— and $X^2$ is —O—. Additionally, in such an embodiment, n can be 2.

With respect to the compounds described herein, Z is

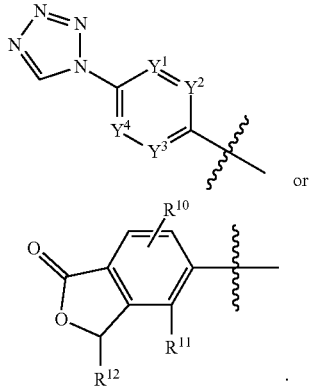

or

In certain embodiments, Z is

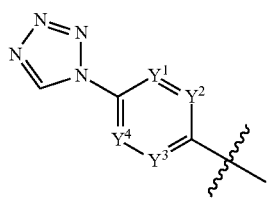

wherein, $Y^1$, $Y^2$, $Y^3$ and $Y^4$ are each independently $C(R^9)$ or N; provided that at most two of $Y^1$, $Y^2$, $Y^3$ and $Y^4$ are N. In certain embodiments, $Y^1$ is $C(R^9)$. In other embodiments, $Y^1$ is N. In other embodiments, $Y^2$ is N. In other embodiments, $Y^3$ is N. In other embodiments, $Y^4$ is N. In certain embodiments, $Y^2$ is $C(R^9)$. In certain embodiments, $Y^3$ is $C(R^9)$. In certain embodiments, $Y^4$ is $C(R^9)$.

With respect to the compounds described herein, each $R^9$ is independently —H, halogen, —$OC_{1-4}$alkyl or $C_{1-4}$alkyl optionally substituted with 1 to 3 halogens. In certain embodiments, $R^9$ is —H. In other embodiments, $R^9$ is halogen. Suitable halogens include, but are not limited to, fluorine, chlorine, bromine and iodine. In yet other embodiments, $R^9$ is $C_{1-4}$alkyl. Suitable $C_{1-4}$alkyl include, but are not limited to, methyl, ethyl, propyl and butyl. In certain embodiments wherein $R^9$ is $C_{1-4}$alkyl, the $C_{1-4}$alkyl is unsubstituted. In other embodiments wherein $R^9$ is $C_{1-4}$alkyl, the $C_{1-4}$alkyl is substituted with 1 to 3 halogens. In certain embodiments wherein $R^9$ is $C_{1-4}$alkyl, the $C_{1-4}$alkyl is substituted with 1, 2 or 3 halogens. Suitable halogens include, but are not limited to, fluorine, chlorine, bromine and iodine. In other embodiments, $R^9$ is $OC_{1-4}$alkyl. Suitable $OC_{1-4}$alkyls include, but are not limited to, methoxy, ethoxy, propoxy and butoxy.

In certain embodiments of the compounds described herein, $Y^1$, $Y^2$, $Y^3$ and $Y^4$ are each —CH—. In certain embodiments of the compounds described herein, $Y^1$, $Y^2$ and $Y^3$ are each —CH— and $Y^4$ is $C(CH_3)$. In other embodiments, $Y^3$ is —N— and $Y^1$, $Y^2$ and $Y^4$ are each —CH—. In yet other embodiments, $Y^4$ is —N— and $Y^1$, $Y^2$ and $Y^3$ are each —CH—. In yet other embodiments, $Y^4$ is —N— and $Y^1$ and $Y^2$ are each —CH— and $Y^3$ is $C(CH_3)$.

In other embodiments, Z is

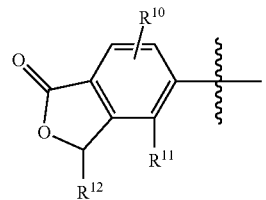

wherein $R^{10}$ is —H, halo, or $C_{1-4}$alkyl optionally substituted with 1 to 3 halo; $R^{11}$ is —H, $C_{1-4}$alkyl optionally substituted with 1 to 3 halo; and $R^{12}$ is —H or $C_{1-4}$alkyl.

In certain embodiments, $R^{10}$ is —H. In other embodiments, $R^{10}$ is halogen. Suitable halogens include, but are not limited to, fluorine, chlorine, bromine and iodine. In yet other embodiments, $R^{10}$ is $C_{1-4}$alkyl. Suitable $C_{1-4}$alkyl include, but are not limited to, methyl, ethyl, propyl and butyl. In certain embodiments wherein $R^{10}$ is $C_{1-4}$alkyl, the $C_{1-4}$alkyl is unsubstituted. In other embodiments wherein $R^{10}$ is $C_{1-4}$alkyl, the $C_{1-4}$alkyl is substituted. In certain embodiments wherein $R^{10}$ is $C_{1-4}$alkyl, the $C_{1-4}$alkyl is substituted with 1, 2 or 3 halogens. Suitable halogens include, but are not limited to, fluorine, chlorine, bromine and iodine.

In certain embodiments, $R^{11}$ is —H. In other embodiments, $R^{11}$ is halogen. Suitable halogens include, but are not limited to, fluorine, chlorine, bromine and iodine. In yet other embodiments, $R^{11}$ is $C_{1-4}$alkyl. Suitable $C_{1-4}$alkyls include, but are not limited to, methyl, ethyl, propyl and butyl. In certain embodiments wherein $R^{11}$ is $C_{1-4}$alkyl, the $C_{1-4}$alkyl is unsubstituted. In other embodiments wherein $R^{11}$ is $C_{1-4}$alkyl, the $C_{1-4}$alkyl is substituted. In certain embodiments wherein $R^{11}$ is $C_{1-4}$alkyl, the $C_{1-4}$alkyl is substituted with 1, 2 or 3 halogens. Suitable halogens include, but are not limited to, fluorine, chlorine, bromine and iodine.

In certain embodiments, $R^{12}$ is —H. In yet other embodiments, $R^{12}$ is $C_{1-4}$alkyl. Suitable $C_{1-4}$alkyl include, but are not limited to, methyl, ethyl, propyl and butyl.

In certain embodiments of the compounds described herein Z is

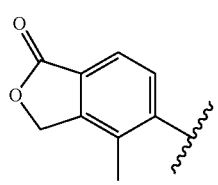

Specifically, described and exemplified herein are the following compounds:

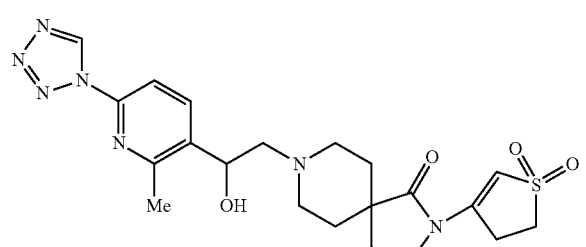

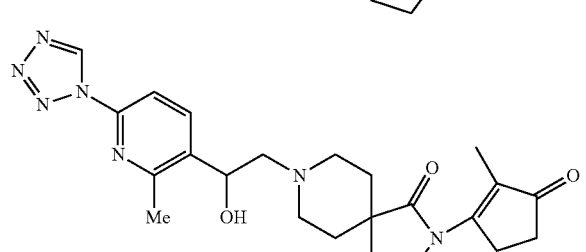

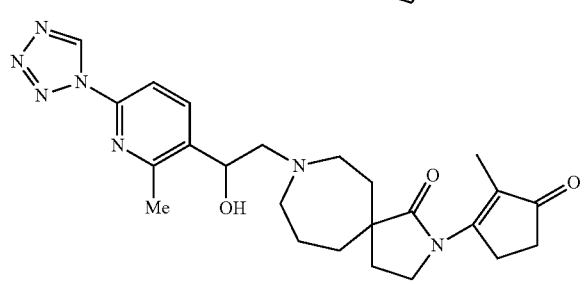

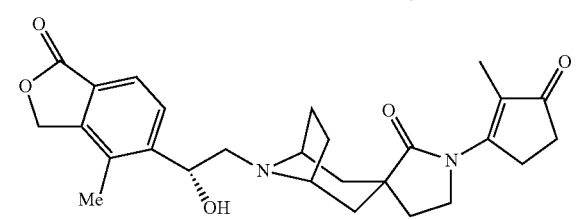

-continued

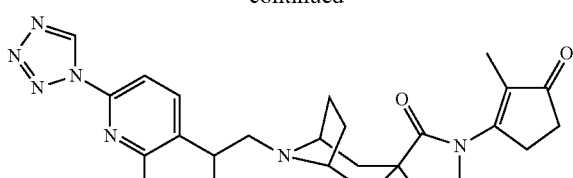

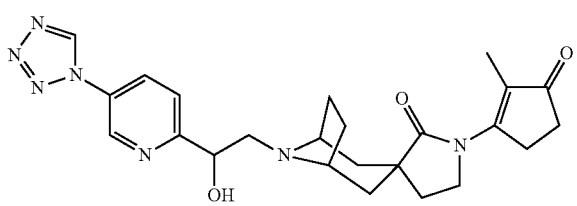

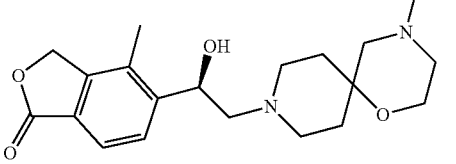

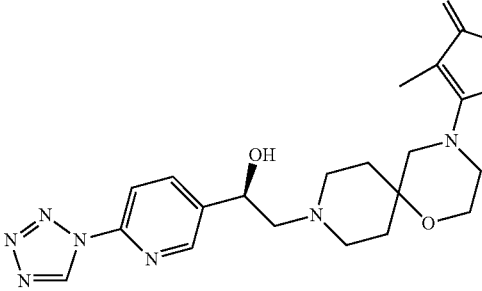

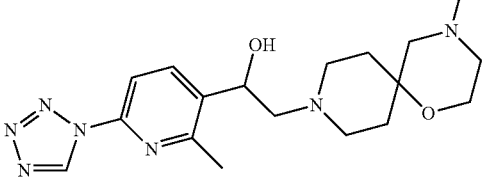

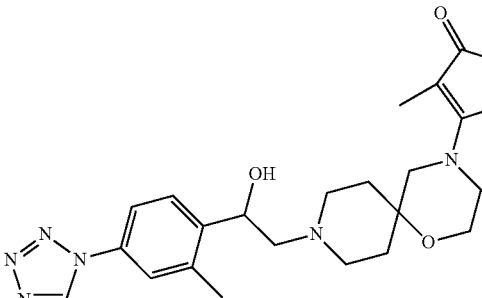

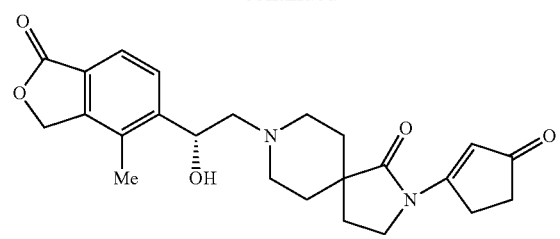
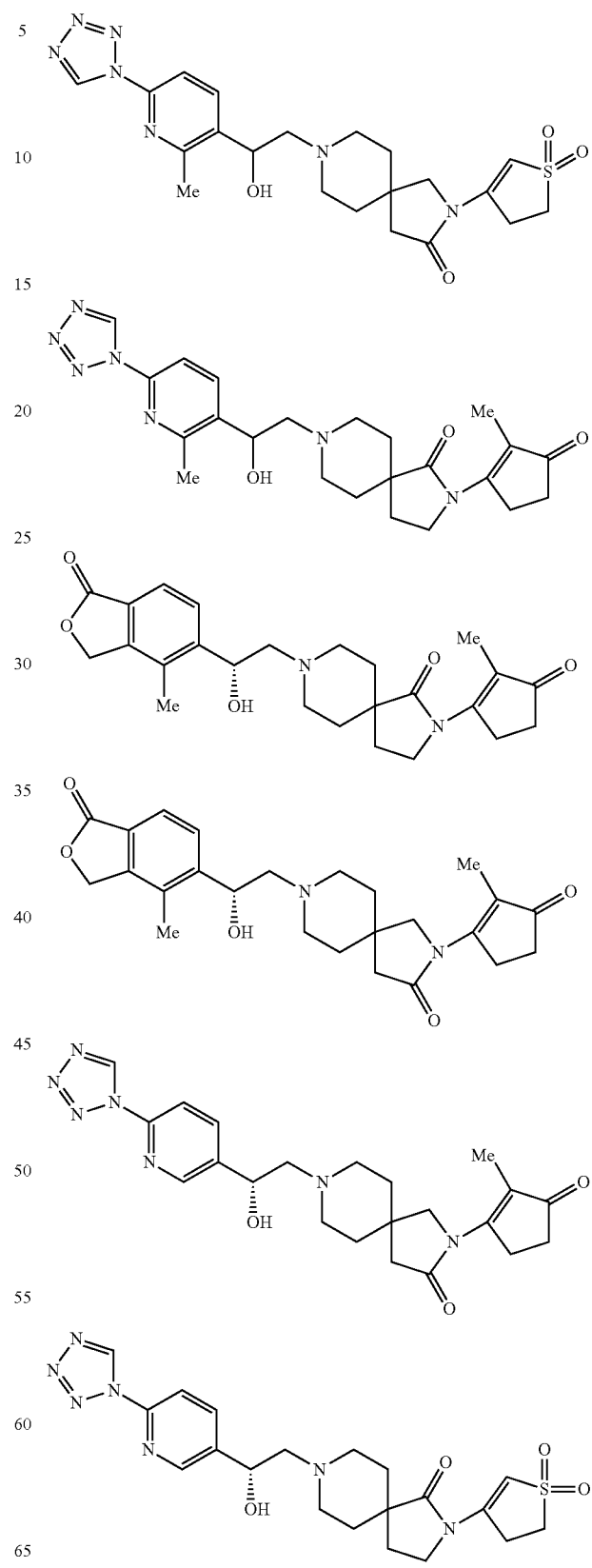

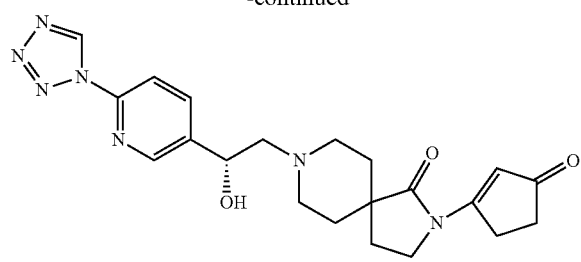
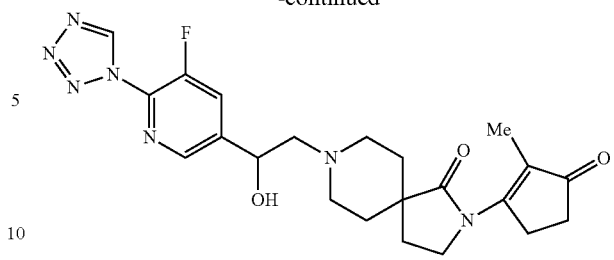
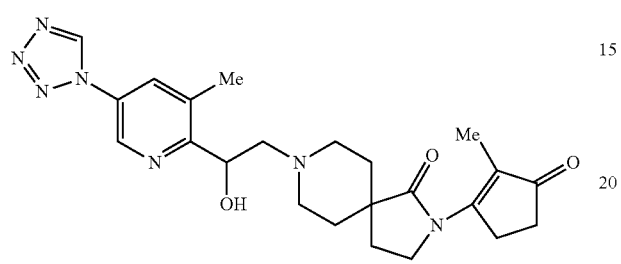
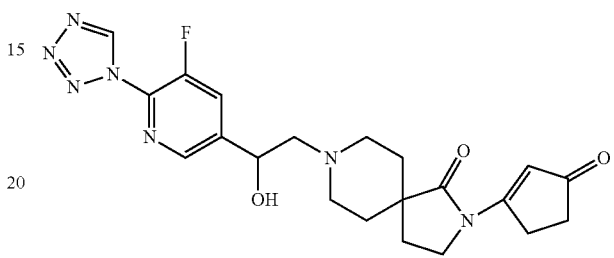
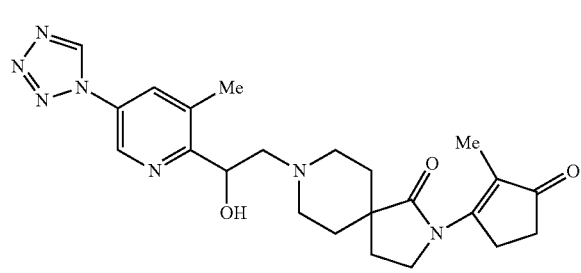
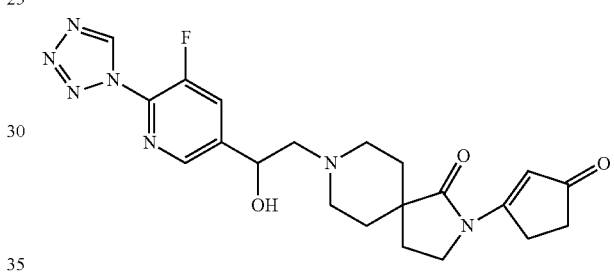
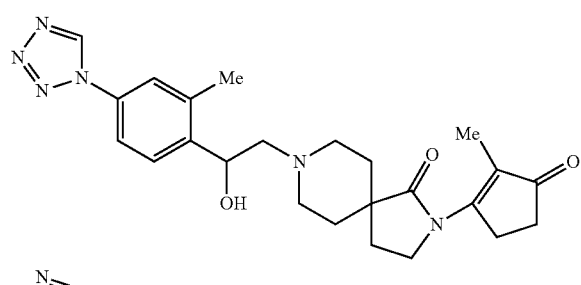
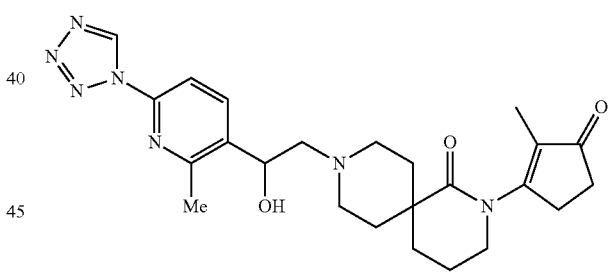
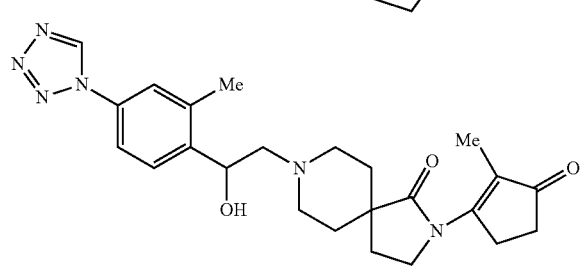
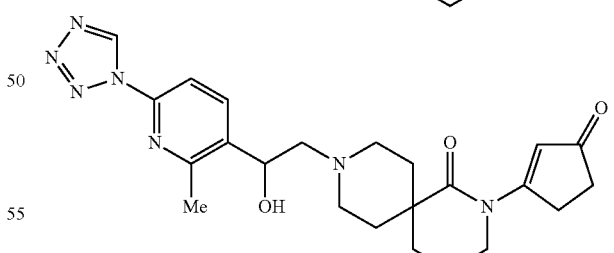
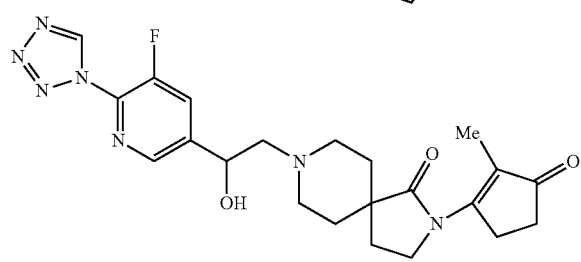
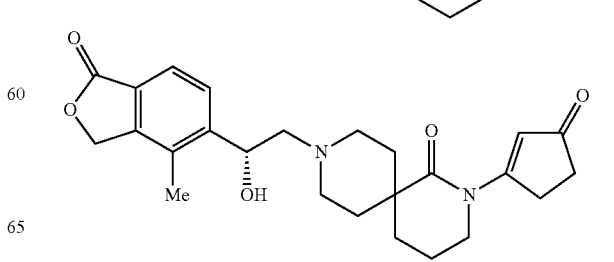

-continued

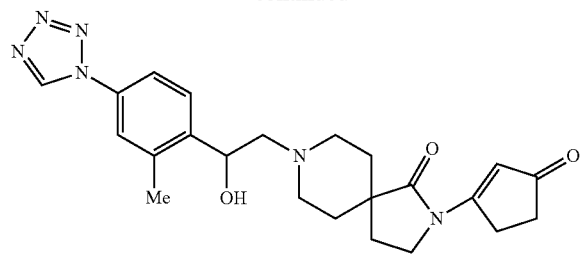
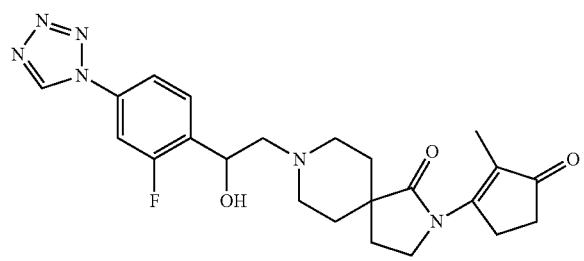
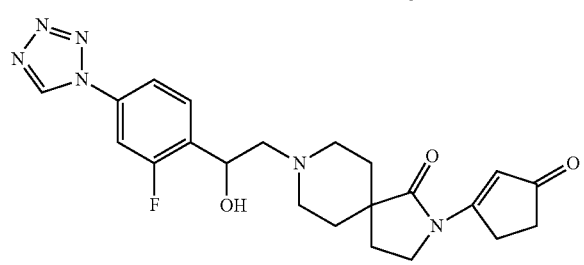
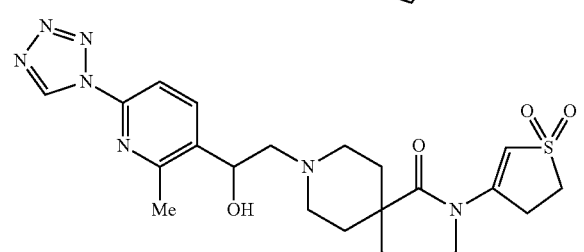
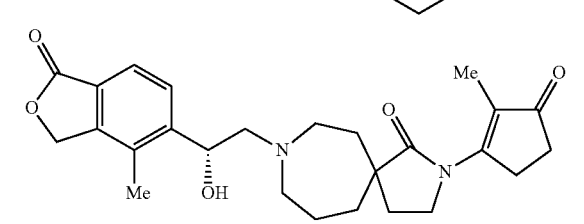
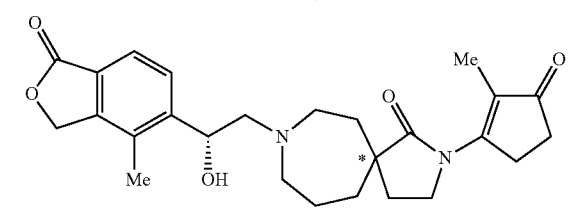
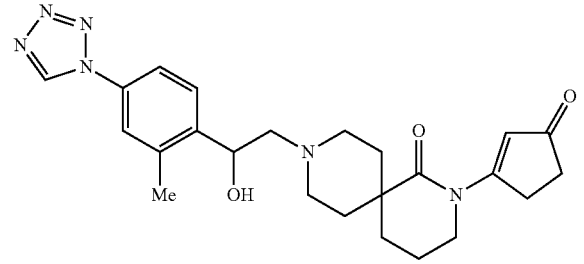

-continued

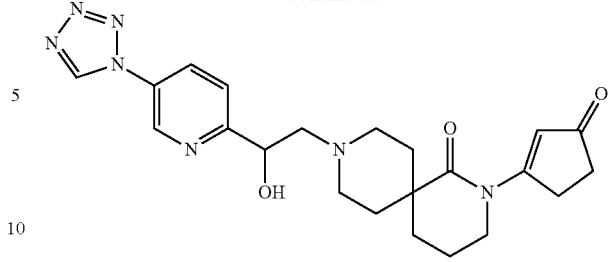
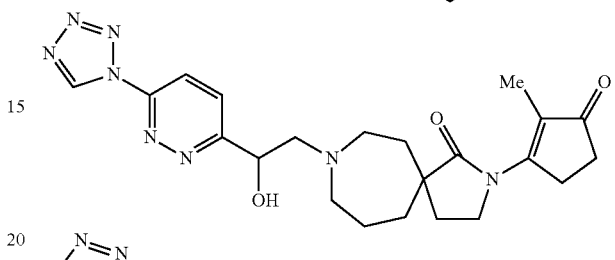
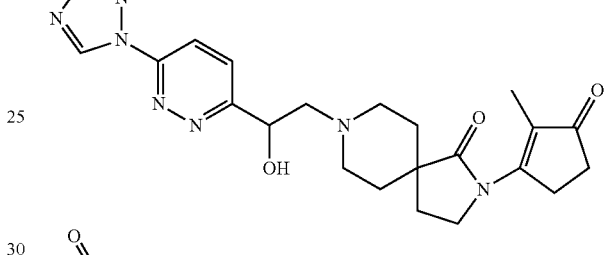
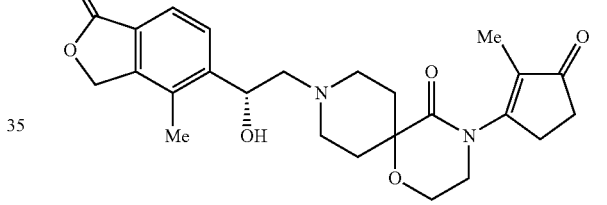

The compounds of the present invention are further described herein using the terms defined below unless otherwise specified.

"Alkyl", as well as other groups having the prefix "alk", such as alkoxy, and the like, means carbon chains which may be linear or branched, or combinations thereof, containing the indicated number of carbon atoms. Examples of alkyl groups include methyl, ethyl, propyl, isopropyl, butyl, sec- and tert-butyl, pentyl, hexyl, heptyl, octyl, nonyl and the like. In specific embodiments, alkyl means a linear or branched $C_{1-3}3$ or $C_{1-4}$alkyl.

"Alkoxy" refers to an alkyl group linked to oxygen. In specific embodiments, alkoxy means a linear or branched $C_{1-3}$ or $C_{1-4}$ alkoxy in which the point of attachment is at oxygen.

"Cycloalkyl" means a saturated cyclic hydrocarbon radical having the number of carbon atoms designated. Examples of cycloalkyl include cyclopropyl, cyclobutyl, cyclopentyl and cyclohexyl. In specific embodiments, cycloalkyl means a $C_{3-6}$ or $C_{3-4}$ cycloalkyl. In particular embodiments, cycloalkyl means $C_3$ cycloalkyl (or cyclopropyl).

"Halogen" or "halo" includes fluorine, chlorine, bromine and iodine.

Unless expressly depicted or described otherwise, variables depicted in a structural formula with a "floating" bond, such as substituent $R^{10}$, are permitted on any available carbon atom in the ring to which each is attached.

Substitution, where applicable, may be on any available carbon atom that results in a stable structure.

Also, number ranges where provided (e.g., 1-6) expressly include each and every number in that range as a discrete embodiment. For example, "1-6" includes 1-6, 1-5, 1-4, 1-3, 1-2, 6, 5, 4, 3, 2 and 1 as distinct embodiments.

Atoms of the compounds described herein may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of any of (1)-(45). For example, different isotopic forms of hydrogen (H) include protium (1H) and deuterium (2H). Protium is the predominant hydrogen isotope found in nature. Enriching for deuterium may yield certain therapeutic advantages, such as increasing in vivo half-life or reducing dosage requirements, or may provide a compound useful as a standard for characterization of biological samples. Isotopically-enriched compounds of any of (1)-(45) described herein can be prepared without undue experimentation by conventional techniques well known to those skilled in the art or by processes analogous to those described in the Examples herein using appropriate isotopically-enriched reagents and/or intermediates.

Individual tautomers of the compounds of any of (1)-(45), as well as mixtures thereof, are encompassed herein. Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers.

Compounds described herein may contain an asymmetric center and may thus exist as enantiomers. Where the compounds according to the invention possess two or more asymmetric centers, they may additionally exist as diastereomers. When bonds to the chiral carbon are depicted as straight lines in the formulas of the invention, it is understood that both the (R) and (S) configurations of the chiral carbon, and hence both enantiomers and mixtures thereof, are embraced. The present invention includes all such possible stereoisomers as substantially pure resolved enantiomers, racemic mixtures thereof, as well as mixtures of diastereomers. Except where otherwise specified, the formulae encompassing compounds of the present invention are shown without a definitive stereochemistry at certain positions. The present invention therefore may be understood to include all stereoisomers of compounds of any of (1)-(45) and pharmaceutically acceptable salts thereof.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of any of (1)-(45) may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Solvates, and in particular, the hydrates of the compounds of any of (1)-(45) are also included in the present invention.

The term "pharmaceutically acceptable salt" refers to a salt prepared from pharmaceutically acceptable non-toxic bases or acids including inorganic bases or acids and organic bases or acids.

Salts of basic compounds encompassed within the term "pharmaceutically acceptable salt" refer to non-toxic salts of the compounds described herein which are generally prepared by reacting the free base with a suitable organic or inorganic acid. Representative salts of basic compounds described herein include, but are not limited to, the following: acetate, benzenesulfonate, benzoate, bicarbonate, bisulfate, bitartrate, borate, bromide, camsylate, carbonate, chloride, clavulanate, citrate, edetate, edisylate, estolate, esylate, formate, fumarate, gluceptate, gluconate, glutamate, hexylresorcinate, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, palmitate, pamoate (embonate), pantothenate, phosphate/diphosphate, polygalacturonate, salicylate, stearate, sulfate, subacetate, succinate, tannate, tartrate, teoclate, tosylate, triethiodide and valerate. Furthermore, where the compounds described herein carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In particular embodiments, the salt is selected from ammonium, calcium, magnesium, potassium, or sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, isopropylamine, lysine, methylglucamine, morpholine, piperazine, piperidine, polyamine resins, procaine, purines, theobromine, triethylamine, trimethylamine, tripropylamine, tromethamine, and the like.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$alkyl esters and —$C_{1-6}$alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and therefore could be used as diuretic and/or natriuretic agents. ROMK inhibitors may be used to help to increase urination and increase urine volume and also to prevent or reduce reabsorption of sodium in the kidneys leading to increased excretion of sodium and water. Therefore, the compounds could be used for treatment or prophylaxis or both of disorders that benefit from increased excretion of water and sodium from the body. Accordingly, the compounds of this invention could be used in a method for inhibiting ROMK comprising administering a compound of Formula I in a ROMK-inhibitory effective amount to a patient in need thereof. This also encompasses the use of the compounds for inhibiting ROMK in a patient comprising administering a compound of Formula I in a therapeutically effective amount to a patient in need of diueresis, natriuresis or both. The inhibition of ROMK by the compounds of Formula I can be examined, for example, in the Thallium Flux Assay described below. Moreover, this invention also relates to the use of the compounds of Formula I or salts thereof to validate in vitro assays, for example but not limited to the Thallium Flux Assay described herein.

The compounds of this invention could be used in a method for causing diuresis, natriuresis or both, comprising administering a compound of Formula I, or a pharmaceutically acceptable salt thereof, in a therapeutically effective amount to a patient in need thereof. Therefore, the compounds of Formula I, or a pharmaceutically acceptable salt thereof, of this invention could be used in methods for treatment of, prevention of or reduction of risk for developing medical conditions that benefit from increased excretion of water and sodium, such as but not limited to one or more of hypertension, such as essential hypertension (also known as primary or idiopathic hypertension) which is a form of hypertension for which no cause can be found, heart failure (which includes both acute heart failure and chronic heart failure, the latter also known as congestive heart failure) and/or other conditions associated with excessive salt and water retention. The compounds could also be used to treat hypertension which is associated with any of several primary diseases, such as renal, pulmonary, endocrine, and vascular diseases, including treatment of patients with medical conditions such as heart failure and/or chronic kidney disease. Furthermore, the compounds of Formula I, or a pharmaceutically acceptable salt thereof, could be used in methods for treatment of, prevention of or reduction of risk for developing one or more disorders such as pulmonary hypertension, particularly pulmonary arterial hypertension (PAH), cardiovascular disease, edematous states, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute kidney insufficiency, chronic kidney insufficiency (also referred to as chronic kidney disease, or more generally as renal impairment), acute tubular necrosis, hypercalcemia, idiopathic edema, Dent's disease, Meniere's disease, glaucoma, benign intracranial hypertension, and other conditions for which a diuretic or natriuretic or both would have therapeutic or prophylactic benefit. The compounds of the invention may be administered to a patient having, or at risk of having, one or more conditions for which a diuretic or natriuretic or both would have therapeutic or prophylactic benefit such as those described herein.

The compounds of Formula I may potentially have reduced unintended effects (for example, hypo- or hyperkalemia, new onset of diabetes, dyslipidemia, etc.) over currently used clinical agents. Also the compounds may have reduced risk for diuretic tolerance, which can be a problem with long-term use of loop diuretics.

In general, compounds that are ROMK inhibitors can be identified as those compounds which, when tested, have an $IC_{50}$ of 5 µM or less, preferably 1 µM or less, and more particularly 0.25 µM or less, in the Thallium Flux Assay, described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, particularly 0.001 to 30 mg/kg, in particular 0.001 to 10 mg/kg (in each case mg per kg of bodyweight) is appropriate for administration to an adult weighing approximately 75 kg in order to obtain the desired results. The daily dose is particularly administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the potency of the compound or the individual response, it may be necessary to deviate upwards or downwards from the given daily dose. Furthermore, the compound may be formulated for immediate or modified release such as extended or controlled release.

The term "patient" includes animals, particularly mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. A "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. The terms "preventing," "prevention," "prophylactic" and derivatives of these terms as used herein refer to administering a compound to a patient before the onset of clinical symptoms of a condition not yet present in the patient. It is understood that a specific daily dosage amount can simultaneously be both a therapeutically effective amount, e.g., for treatment of hypertension, and a prophylactically effective amount, e.g., for prevention or reduction of risk of myocardial infarction or prevention or reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous (IV), intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example for the treatment of acute heart failure.

This invention also provides pharmaceutical compositions comprised of a compound of Formula I, or a pharmaceutically acceptable salt thereof, and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients which are suitable for the manufacture of tablets. The excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example but not limited to, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants. Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I, or a pharmaceutically acceptable salt thereof, with a pharmaceutically acceptable carrier. Also encompassed is the pharmaceutical composition which is made by combining a compound of Formula I, or a pharmaceutically acceptable salt thereof, with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from about 0.1 mg to 1 g, particularly 0.1 mg to about 200 mg, more particularly from about 0.1 mg to about 100 mg, and even more particularly from about 0.1 to about 50 mg, per dose on a free acid/free base weight basis, but depending on the type of the pharmaceutical composition, potency of the active ingredient and/or the medical condition being treated, it could also be lower or higher. Pharmaceutical compositions usually comprise about 0.5 to about 90 percent by weight of the active compound on a free acid/free base weight basis.

The compounds of Formula I inhibit ROMK. Due to this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I, or a pharmaceutically acceptable salt thereof. The additional active agent (or agents) is intended to mean a medicinal compound that is different from the compound of Formula I, and which is a pharmaceutically active agent (or agents) that is active in the body, including pro-drugs, for example esterified forms, that convert to pharmaceutically active form after administration, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of the one or more additional active agents which may be employed include but are not limited to thiazide-like diuretics, e.g., hydrochlorothiazide (HCTZ or HCT); angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); dual inhibitors of angiotensin converting enzyme (ACE) and neutral endopeptidase (NEP) such as omapatrilat, sampatrilat and fasidotril; angiotensin II receptor antagonists, also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; carbonic anhydrase inhibitors, such as acetazolamide; neutral endopeptidase inhibitors (e.g., thiorphan and phosphoramidon); angiotensin receptor neprilysin inhibitors (e.g., LCZ696); aldosterone antagonists; aldosterone synthase inhibitors; renin inhibitors (e.g., enalkrein; RO 42-5892; A 65317; CP 80794; ES 1005; ES 8891; SQ 34017; aliskiren (2(S), 4(S), 5(S), 7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate), SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine, bepridil, nisoldipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g. isosorbide mononitrate; lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), SGLT2 inhibitors (e.g., canagliflozin, dapagliflozin, ipragliflozin, empagliflozin, tofogliflozin, luseogliflozin/TS-071, ertugliflozin, and remogliflozin), dipeptidyl peptidase inhibitors, (e.g., sitagliptin (JANUVIA®), omarigliptin, alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; phosphodiesterase-5 (PDE5) inhibitors such as sildenafil (Revatio, Viagra), tadalafil (Cialis, Adcirca) vardenafil HCl (Levitra); or with other drugs beneficial for the prevention or the treatment of the above-mentioned diseases including but not limited to diazoxide; and including the free-acid, free-base, and pharmaceutically acceptable salt forms, pro-drug forms (including but not limited to esters), and salts of pro-drugs of the above medicinal agents where chemically possible. Trademark names of pharmaceutical drugs noted above are provided for exemplification of the marketed form of the active agent(s); such pharmaceutical drugs could be used in a separate dosage form for concurrent or sequential administration with a compound of Formula I, or the active agent(s) therein could be used in a fixed dose drug combination including a compound of Formula I.

EXAMPLES

Several methods for preparing the compounds of this invention are described in the following Schemes and Examples. Starting materials and intermediates are purchased, made from known procedures, or as otherwise illustrated. Some frequently applied routes to the compounds of Formula I are also described by the Schemes as follows. In some cases the order of carrying out the the steps of reaction schemes may be varied to facilitate the reaction or to avoid unwanted reaction products. Unless specified otherwise, the "R", "Z", "X", "m" and "n" substituents in the Schemes correspond to the substituents defined in Formula I at the same positions on the structures.

Compound 1.3, which is substituted at the benzylic position with an OH group, can be prepared following the sequence detailed in Scheme 1. Coupling of epoxide 1.1 to spirocyclic amines 1.2 at elevated temperatures leads to the formation of alcohols 1.3 (Nomura, Y. et al. Chemical &

Pharmaceutical Bulletin, 1995, 43(2), 241-6). The reaction can be carried out with conventional heating, or by heating using a microwave apparatus. A number of solvents can be used in this reaction, for example, ethanol and 2-propanol. Spirocyclic amines may be free bases, or they may be salts, in which case a base such as triethylamine or N;N-diisopropylethylamine may be added. Note that when enantiomerically pure chiral epoxides are employed (such as (R)-1.1 in Scheme 1) epoxide opening occurs with retention of stereochemistry in the benzylic position and individual isomer (R)-1.3 may be obtained (and if the (S)-epoxide is employed the alcohol produced will have the opposite stereochemistry to that shown). Alternatively, chiral HPLC separation of enantiomers or diastereomers of 1.3 may be performed to provide single enantiomers or diastereomers.

The corresponding epoxides 1.1 can then be obtained by epoxidation of intermediates 2.2 with NBS/NaOH or with a peroxide reagent such as meta-chloro peroxybenzoic acid. Other methods for formation of styrene 2.3 may be employed, for example, using vinylstannane reagents and palladium catalysis. The racemic epoxides of formula 1.1 can be resolved under chiral HPLC chromatography conditions to afford single enantiomers (R)-1.1 and (S)-1.1, which can be used in place of 1.1 according to Scheme 1.

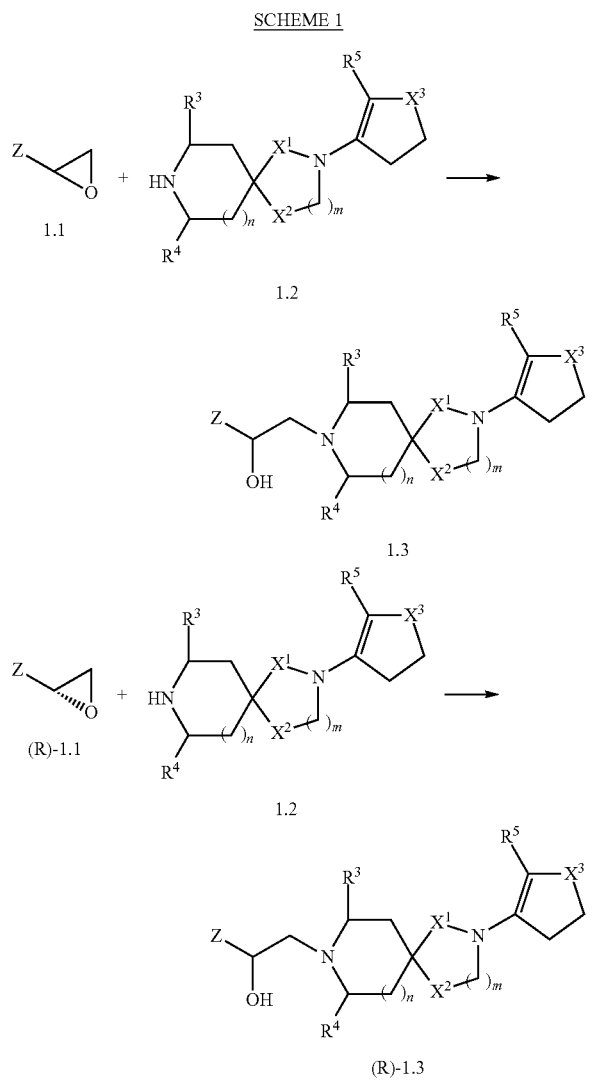

Alternatively, enantiopure epoxides (R)-1.1 or (S)-1.1 can be prepared as shown in Scheme 3. Treatment of 2.1, where Z is defined as described for Formula I, and X is chloride, bromide, iodide, or trifluoromethane sulfonate, with commercially available vinyl butylether 3.1 under palladium catalyzed conditions with a suitable ligand (for example Pd(OAc)$_2$, DPPP) can provide the enol ethers 3.2. Enol ethers may be prepared using other methods known to the chemist. Treatment of the resulting enol ethers 3.2 with NBS or other similar reagents affords the corresponding bromomethyl ketones 3.3. These can be subjected to a variety of asymmetric ketone reduction conditions, for example with an enzyme that can affect such a transformation with high enantioselectivity. Subsequent treatment with a base such as triethylamine leads to cyclization, affording the enantioenriched epoxides (R)-1.1 or (S)-1.1 (depending upon the asymmetric reducing agent).

A typical route for the preparation epoxide intermediates 1.1 is depicted in Scheme 2. Intermediates 2.1, where Z is defined as described for Formula I, and X is chloride, bromide, iodide, or trifluoromethane sulfonate, can be converted to the corresponding alkenyl intermediates 2.2 by treatment with potassium vinyl trifluoroborate (Molander, G.; Luciana, A. Journal of Organic Chemistry, 2005, 70(10), 3950-3956) under palladium catalyzed coupling conditions.

Spirocyclic amines 1.2 can be prepared as described in Scheme 4. Spirocyclic intermediates 4.1, where an amine is protected as appropriate, for example with tert-butoxycarbonyl as shown, (Greene, T.; Wuts, P. G. M. *protective Groups in Organic Synthesis*, John Wiley and Sons, Inc., New York, N.Y. 1991), can be coupled to triflates or bromides 4.2 using a palladium catalyst and ligand, for example palladium acetate and 4,5-Bis(diphenylphosphino)-9,9-dimethylxanthene to afford intermediates 4.3. Some intermediates 4.1 described herein are commercially available; others can be prepared as described in the Schemes and experimental section below. In some instances, intermediates 4.3 can also be prepared by heating intermediates 4.1 with a subset of intermediates 4.2 where X is hydroxy. Removal of the protective group present in intermediates 4.3, for example tert-butoxycarbonyl, can be achieved according to the nature of the protective group; for tert-butoxycarbonyl commonly this involves treatment with TFA or HCl. The resulting spirocyclic intermediates 1.2 can be used as described in Scheme 1 above to afford ROMK inhibitors.

SCHEME 4

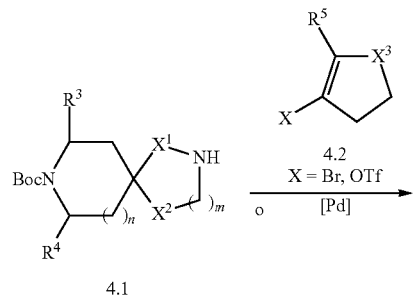
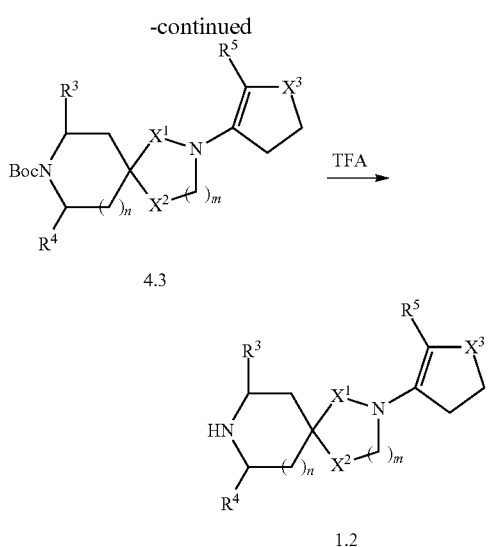

Spirocyclic protected amines 4.1, can be prepared in numerous ways, depending on their individual structures. Syntheses of several types of 4.1 are described in the Experimental Section below. One typical example of 4.1 (4.1a) can be prepared as described in Scheme 5. Aminoesters 5.1 can be alkylated with bromoacetonitrile 5.2 using a base such as lithium diisopropylamide to afford nitrile intermediates 5.3. Reduction, for example using platinum oxide and hydrogen, or Raney Nickel, produces lactams 4.1a. Alternatively, aminoesters may be alkylated with allyl halides 5.4 using a base such as lithium diisopropylamide to furnish allyl intermediates 5.5. Oxidative cleavage, employing, for example, osmium tetroxide and sodium periodate provides ketones or aldehydes 5.6. Reductive amination with tandem lactam cyclization to 4.1a can be accomplished in several ways, including by treatment with ammonium acetate and sodium cyanoborohydride in a solvent such as methanol (as shown). Intermediates 4.1a may be used in place of 4.1 in Scheme 4.

SCHEME 5

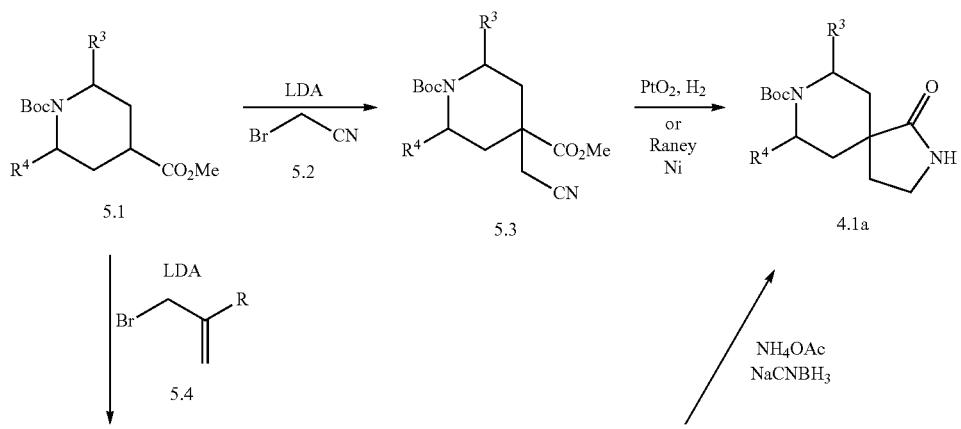

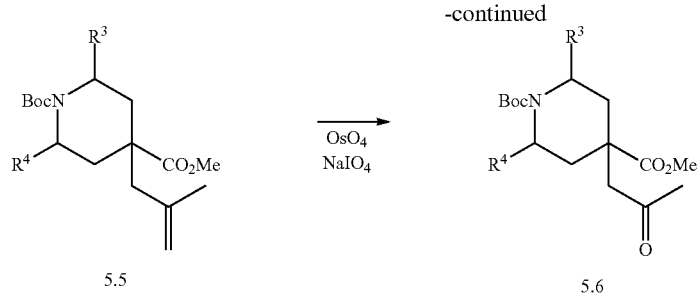

Intermediates 4.2 are either commercially available, or can be prepared as described in the Experimental Section. Two typical procedures providing intermediate bromides or triflates are outlined in Scheme 6. 1,3-Cyclopentadiones 6.1 can be treated with a brominating reagent, for example dibromotriphenylphosphorane, followed by an amine such as triethylamine to afford bromides 4.2a. Alternatively, 1,3-cyclopentadiones 6.1 can be treated with triflic anhydride in the presence of a base such as 2,6-lutidine at low temperature to afford triflates 4.2b. These may be used in place of 4.2 in Scheme 4.

SCHEME 6

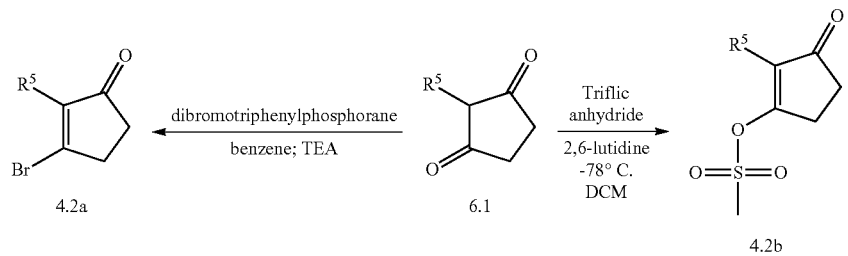

One useful example of 2.1 (2.1a) when Z in Formula I is

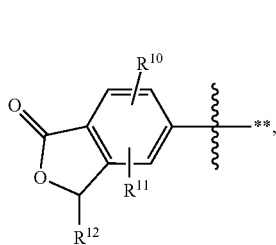

can be prepared as described in Scheme 7. Benzoic acids of the type 7.1 can be reduced in a variety of ways to benzyl alcohols 7.2, including, for example, by treatment with sodium borohydride and $BF_3$-etherate. Bromination of benzyl alcohols 7.2 to afford bromides 7.3 can be achieved, for example, by treatment with N-bromosuccinimide and trifluoroacetic acid. Replacement of the bromide in 7.3 with cyano by heating with CuCN in DMF, followed by hydrolysis can provide phthalides 7.4 in one pot. Finally, treatment with triflic anhydride in the presence of a base, such as triethylamine, can provide triflates 2.1a. Triflates 2.1a can be used in place of 2.1 in Schemes 2 and 3.

SCHEME 7

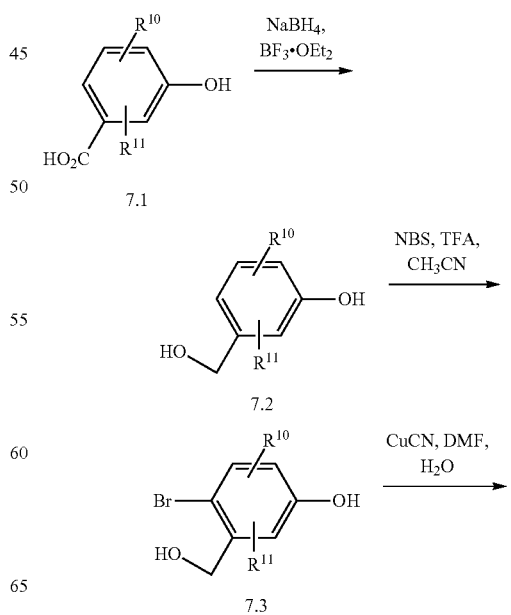

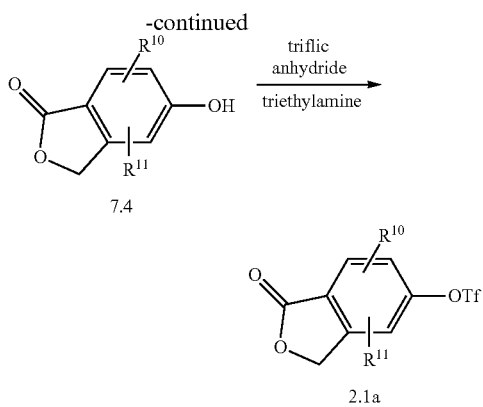

Another useful example of 2.1 (2.1b) when Z in Formula I is

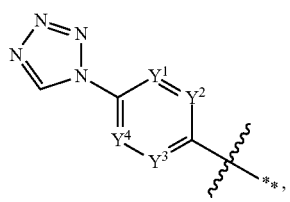

can be prepared as described in Scheme 8. Starting from amines 8.1, formation of the tetrazole ring can be accomplished by treatment with $CF_3CO_2TMS$, $N_3TMS$ and $CH(OEt)_3$ in ethyl acetate or by treatment with $NaN_3$ and $CH(OEt)_3$ in acetic acid to afford 2.1b. Bromides 2.1b can be used in place of 2.1 in Schemes 2 and 3.

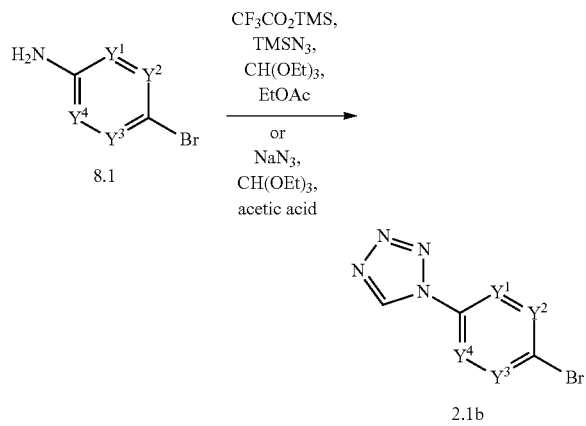

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry, or by vibrational circular dichroism (VCD) spectroscopy.

The subject compounds may be prepared by modification of the procedures disclosed in the Examples as appropriate.

Starting materials are commercially available or made by known procedures or as illustrated Reactions sensitive to moisture or air were performed under nitrogen or argon using anhydrous solvents and reagents. The progress of reactions was determined by either analytical thin layer chromatography (TLC) usually performed with E. Merck pre-coated TLC plates, silica gel 60F-254, layer thickness 0.25 mm or liquid chromatography-mass spectrometry (LC-MS).

Typically the analytical LC-MS system used consisted of a Waters ZQ platform with electrospray ionization in positive ion detection mode with an Agilent 1100 series HPLC with autosampler. The column was usually a Water Xterra MS C18, 3.0×50 mm, 5 µm. The flow rate was 1 mL/min, and the injection volume was 10 µL. UV detection was in the range 210-400 nm. The mobile phase consisted of solvent A (water plus 0.06% TFA) and solvent B (acetonitrile plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using a mass spectrometry directed system. Usually they were performed on a Waters Chromatography Workstation configured with LC-MS System Consisting of: Waters ZQ single quad MS system with Electrospray Ionization, Waters 2525 Gradient Pump, Waters 2767 Injector/Collector, Waters 996 PDA Detector, the MS Conditions of: 150-750 amu, Positive Electrospray, Collection Triggered by MS, and a Waters Sunfire C-18 5 micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. Mobile phase gradients were optimized for the individual compounds.

Reactions performed using microwave irradiation were normally carried out using an Emrys Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1H$ NMR spectra were acquired at 500 MHz spectrometers in $CDCl_3$ solutions unless otherwise noted. Chemical shifts were reported in parts per million (ppm). Tetramethylsilane (TMS) was used as internal reference in $CD_3Cl$ solutions, and residual $CH_3OH$ peak or TMS was used as internal reference in $CD_3OD$ solutions. Coupling constants (J) were reported in hertz (Hz).

Chiral analytical chromatography was usually performed on one of Chiralpak AS, Chiralpak AD, Chiralcel OD, Chiralcel IA, or Chiralcel OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was sometimes conducted on one of Chiralpak AS, Chiralpak AD, Chiralcel OD, Ciralcel IA, or Chiralcel OJ columns (20×250 mm) (Daicel Chemical Industries, Ltd.) with desired isocratic solvent systems identified on chiral analytical chromatography or by supercritical fluid (SFC) conditions. Alternatively, chiral preparative chromatography was by supercritical fluid (SFC) conditions using one of Chiralpak AS, Chiralpak AD-H, Chiralcel OD-H, Chiralpak IC, or Chiralcel OJ-H columns (250×21.2 mm) (Daicel Chemical Industries, Ltd.). Where retention times (or order of elution) are provided in the Examples and Tables, they are not intended to be a definitive characteristic of a particular compound since, as known to those skilled in the art, retention times will vary and the timing and/or order of peak elution may change depending on the chromatographic conditions, such as the column used, the condition of the column, and the solvent system and instruments used. Concentration of solutions was generally carried out on a rotary evaporator under reduced pressure Crystallization or recrystallization techniques are intended to describe a purification procedure that was used, but do not imply that the resulting product obtained from the procedure is crystalline.

Abbreviations and acronyms that may be used herein include: —C(O)CH$_3$ (Ac); —OC(O)CH$_3$ (OAc); acetic acid (AcOH; HOAc); 1-chloroethylchloroformate (ACE-Cl); 2,2'-bis(diphenylphosphino)-1,1'-binaphthyl (BINAP); benzyl (Bn); t-butyloxycarbonyl (Boc or BOC); di-t-butyl dicarbonate ((BOC)$_2$O, Boc$_2$O); benzyloxycarbonyl (Cbz); Cyclopentyl methyl ether (CPME); Carbonyldiimidazole (CDI); Diethylaminosulfur trifluoride (DAST); dibenzylideneacetone (dba); 1,8-Diazabicyclo[5.4.0]undec-7-ene (DBU); 1,2-dichloroethane (DCE); dichloromethane (DCM); diethyl amine (DEA); dimethoxyethane (DME); Diisobutylaluminium hydride (DIBAL-H); N,N-diisopropylethylamine (DIEA, DIPEA, Hunig's base); dioxane is 1,4-dioxane; di-isopropylamine (DIPA); 1,1'-bis(diphenylphosphino)ferrocene (dppf, DPPF); Dess-Martin Periodinane (DMP; 1,1,1-Triacetoxy-1,1-dihydro-1,2-benziodoxol-3 (1H)-one); dimethylsulfide (DMS); dimethylsulfoxide (DMSO); N;N-dimethylformamide (DMF); 4-dimethylaminopyridine (DMAP); dimethylacetamide (DMA; DMAC); 1,3-Bis(diphenylphosphino)propane (DPPP); (Oxydi-2,1-phenylene)bis(diphenylphosphine) (DPEPhos); ethyl acetate (EtOAc or EA); diethyl ether (ether or Et$_2$O); 1-ethyl-3-(3-dimethylaminopropyl)carbodiimide (EDC, EDAC or EDCl); 2-(7-Aza-1H-benzotriazole-1-yl)-1,1,3,3-tetramethyluronium hexafluorophosphate (HATU); hexane (Hex); hexamethylphosphoramide (HMPA); 1-Hydroxybenzotriazole hydrate (HOBt); isopropanol (IPA); isopropyl acetate (IPAc); Potassium bis(trimethylsilyl)amide (KHMDS); lithium aluminum hydride (LAH); lithium diisopropylamide (LDA); 3-chloroperoxybenzoic acid (mCPBA); methanol (MeOH); CH$_3$SO$_2$— (mesyl or Ms); methane sulfonyl chloride or mesyl chloride (MsCl); methanesulfonic acid (MsOH); methyl tert-butyl ether (MTBE); nicotinamide adenine dinucleotide phosphate (NADP); N-bromo succinimide (NBS); N-chlorosuccinimide (NCS); N-iodosuccinimide (NIS); N-methylmorpholine-N-oxide (NMO); N-methyl morpholine (NMP); sodium hexamethyldisilazide (NaHMDS); sodium triacetoxyborohydride (NaBH(OAc)$_3$); Pyridinium chlorochromate (PCC); phenyl (Ph); petroleum ether (PE or petrol ether); tetrakis(triphenylphosphine)palladium (Pd(PPh$_3$)$_4$); tris(dibenzylidineacetone)dipalladium (Pd$_2$(dba)$_3$); Pd(dppf)Cl$_2$ or PdCl$_2$(dppf) is 1,1'-Bis(diphenylphosphino)ferrocene]dichloropalladium (II) which may be complexed with CH$_2$Cl$_2$; tetra-n-butylammonium fluoride (TBAF); tert-butyldimethylsilyl chloride (TBS-Cl); triethylamine (TEA); trifluoroacetic acid (TFA); —SO$_2$CF$_3$ (Tf); trifluoromethanesulfonic acid (triflic acid, TfOH); trifluoromethanesulfonic anhydride (triflic anhydride, (Tf)$_2$O); 2-tetrahydrofuran (THF); N,N,N',N'-Tetramethylethylenediamine (TMEDA); p-toluenesulfonic acid (TsOH or PTSA); Dicyclohexylphosphino-2',4',6'-triisopropylbiphenyl (X-Phos); Diethylaminodifluorosulfinium tetrafluoroborate (XtalFluor-E®); 4,5-Bis(diphenylphosphino)-9,9-dimethylxanthene (Xantphos). Additional abbreviations and acronyms are: racemic or racemate (rac.); starting material (SM); round-bottom flask (RB or RBF); aqueous (aq); saturated aqueous (sat'd); saturated aqueous sodium chloride solution (brine); medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); mass spectrum (ms or MS); liquid chromatography-mass spectrometry (LC-MS, LCMS or LC/MS); column volume (CV); room temperature (rt, r.t. or RT); hour(s) (h or hr); minute(s) (min); retention time (R$_t$); gram(s) (g); milligram(s) (mg); milliliter(s) (mL); microliter(s) (□L); millimole (mmol); volume:volume (V/V). CELITE is a trademark name for diatomaceous earth, and SOLKA FLOC is a trademark name for powdered cellulose. X or x may be used to express the number of times an action was repeated (e.g., washed with 2×200 mL 1N HCl), or to convey a dimension (e.g., the dimension of a column is 30×250 mm).

The following are representative procedures for the preparation of intermediates used to prepare the final products described in the Examples that follow thereafter. These examples are provided for the purpose of further illustration only and are not intended to be limitations on the disclosed invention.

It is understood that a chiral center in a compound may exist in the "S" or "R" stereo-configurations, or as a mixture of both. In many of the examples for intermediate compounds and final compounds, such compounds having a racemic chiral center were separated into individual stereoisomers, for example, referred to as isomer A (or enantiomer A or the like), which refers to the observed faster eluting isomer, and isomer B (or enantiomer B or the like), which refers to the observed slower eluting isomer, and each such isomer may be noted in the example as either the fast or slow eluting isomer. When a single "A" or "B" isomer intermediate is used to prepare a downstream compound, the downstream compound may take the "A" or "B" designation that corresponds to the previously used intermediate. Any Intermediates described below may be referred to herein by their number preceded by "I-." For illustration, in the example titled "Intermediate 2," the racemic parent title compound would be referred to as Intermediate 2 (or I-2), and the separated stereoisomers are noted as Intermediates 2A and 2B (or I-2A and I-2B). In some examples, compounds having a chiral center were derived synthetically from a single isomer intermediate; e.g., Example 2 was made using stereoisomer I-1B. Except for a defined chiral center in a parent isomer mixture, absolute stereochemistry (R or S) of each of the separated isomers was not determined, unless specifically described otherwise. An asterisk (*) may be used in a chemical structure drawing that indicates the location of a chiral center.

Intermediate 1

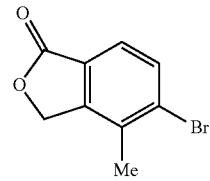 [SMILES: Cc1c(Br)ccc2c1COC2=O]

5-bromo-4-methyl-2-benzofuran-1(3H)-one

Step A: (3-bromo-2-methylphenyl)methanol

To a solution of 3-bromo-2-methyl benzoic acid (35 g, 163 mmol) in THF (200 mL) was added Borane in THF (1.0 M, 212 mL, 212 mmol). The mixture was allowed to stir for 24 h. TLC showed one single product spot. The reaction was quenched with water. The solvent THF was removed under reduced pressure. The resulting solid was dissolved in ethyl acetate (500 mL), washed with 1N HCl, sodium carbonate, and brine. The organic layer was dried over sodium sulfate and concentrated to afford (3-bromo-2-methylphenyl)methanol. $^1$H NMR (500 MHz, CDCl$_3$) δ 7.76 (d, J=8.0 Hz, 1H), 7.63 (d, J=8.0 Hz, 1H), 5.30 (s, 2H), 2.42 (s, 3H).

Step B: 5-bromo-4-methyl-2-benzofuran-1(3H)-one

To a flask charged with (3-bromo-2-methylphenyl)methanol (6.0 g, 30 mmol) was added a 1M TFA solution of Thallium Trifluoroacetate (16.2 g, 29.8 mmol). The mixture was stirred at rt overnight. Analysis by TLC showed no starting material remaining. The solvent was removed under vacuum, and the residue was pumped under high vacuum for 30 min to ensure complete removal of TFA. To the residue was then added Palladium(II) Chloride (529 mg, 2.98 mmol), Lithium Chloride (2.53 g, 59.7 mmol), Magnesium Oxide (2.41 g, 59.7 mmol), and MeOH (150 mL). The reaction was flushed with CO twice, and kept under CO at room temperature. Analysis by LC showed a big product spot within 2 hours. To this solution was added ethyl acetate to precipitate the salts. The black solution was filtered through a CELITE pad, washed with EtOAc, adsorbed onto silica and purified by silica gel chromatography to afford title compound. $^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 2

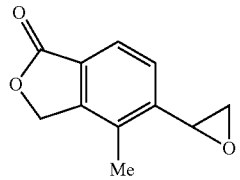 [SMILES: Cc1c(C2CO2)ccc2c1COC2=O]

4-methyl-5-oxiran-2-yl-2-benzofuran-1(3H)-one

Step A: 5-ethenyl-4-methyl-2-benzofuran-1(3H)-one

5-Bromo-4-methyl-2-benzofuran-1(3H)-one (598 mg, 4.47 mmol), potassium vinyl trifluoroborate (507 mg, 2.23 mmmol), PdCl$_2$(dppf)-CH$_2$Cl$_2$Adduct (182 mg, 0.223 mmmol), and TEA (0.622 mL, 4.47 mmol) were added to 10 mL ethanol in a 20 mL microwave tube. The tube was sealed and degassed, then heated to 140° C. for 20 min. Analysis by LC-MS showed product peak. The reaction mixture was diluted with ethyl acetate, washed with brine twice, dried and evaporated to dryness. The crude product was purified by MPLC chromatography using a 120 g Redi-sep column and 0-80% ETOAC/Hexane solvent system to yield 5-ethenyl-4-methyl-2-benzofuran-1(3H)-one. $^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H); LC-MS: M+1=175;

Step B: 4-methyl-5-oxiran-2-yl-2-benzofuran-1(3H)-one 5-ethenyl-4-methyl-2-benzofuran-1(3H)-one (1.46 g, 8.38 mmol) was added to DCM (25 mL) at 0° C. then mCPBA (2.89 g, 16.8 mmol) was added and the mixture was stirred at rt overnight. The reaction mixture was washed once each with saturated aqueous Na$_2$S$_2$O$_3$, NaHCO$_3$, and brine. The organic layer was dried over Na$_2$SO$_4$, filtered, and evaporated to dryness. The crude material was purified by MPLC chromatography through 120 g Redi-sep column eluting with 0-80% EtOAc/hexane solvent system to yield target 4-methyl-5-oxiran-2-yl-2-benzofuran-1(3H)-one. $^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.735 (dd, J=2.2, 5.5 Hz, 1H), 2.43 (s, 3H). LC-MS: M+1=191.

Intermediates 2A and 2B (Method 1)

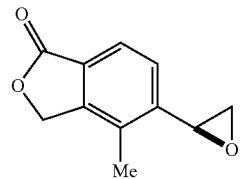

Slow eluting 2A

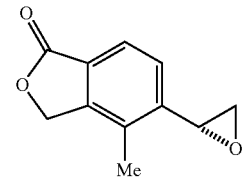

Fast eluting 2B

3A: 4-methyl-5-[(2S)-oxiran-2-yl]-2-benzofuran-1(3H)-one

3B: 4-methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/mL in 1:1 DCM:MeOH. The separation was accomplished using 10% EtOH/CO$_2$, flow rate 200 mL/min, 100 bar, 25° C. 500 ul Injections were spaced every 2.12 mins. The fast epoxide (4-methyl-5-[(2R)-oxiran-2-yl]-2-benzofuran-1(3H)-one, 2B) eluted first, and the slow epoxide (4-methyl-5-[(2S)-oxiran-2-yl]-2-benzofuran-1(3H)-one, 2A) eluted second.

Alternatively, the resolution could also be achieved using a mobile phase of 8% MeOH/98% CO$_2$ with a flow rate of 100 mL/min. In that case the sample was prepared by dissolving in methanol, 20 mg/mL, and using a 1 mL volume per injection. After separation, the fractions were dried off via rotary evaporator at bath temperature 40° C.

The absolute stereochemistry of each enantiomer was inferred based on the X-ray crystal structure determination of a final compound made with 2B and by Mosher ester and Trost ester HNMR analysis of esters made starting from 2B. Both epoxide isomers find utility in the present invention.

Intermediate 2B (Method 2)

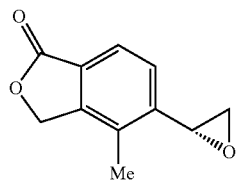 [SMILES: Cc1c([C@@H]2CO2)ccc2c1COC2=O]

4-methyl-5-[(2R)-oxiran-2-yl]-2-benzofuran-1(3H)-one

Step A: 3-hydroxymethyl-2-methyl phenol

To a 5 L 3 neck round bottom flask equipped with overhead stirrer was charged NaBH$_4$ (87.0 g, 2.30 mol) and THF (3.0 L) and the resulting slurry was cooled to 10° C. To the slurry was then added 3-hydroxy-2-methyl benzoic acid (175 g, 1.15 mol) portionwise over 20 min (Tmax 17° C.). A stirrable slurry formed, and was aged for an additional 45 min at 10-15° C. after which BF$_3$-OEt$_2$ (321 mL, 2.53 mol) was added slowly over 1.5 hours. The slurry was aged at 10° C.-15° C. for 2 h then assayed for reaction completion (98.5% conversion). The slurry was cooled to <10° C. and quenched with 931 mL MeOH slowly over 1.5 h (gas evolution). The resulting slurry was aged overnight at rt. The batch was cooled to <10° C. then quenched with 1 N HCl (1.5 L) to get a homogeneous solution (pH solution~1), which was aged for 30 min and then the organic solvents were removed by rotary evaporation to approximately 1.8 L of total reaction volume (bath temperature was set to 50° C.; internal temp of concentrate after rotary evaporation was ~40° C.). The slurry was held at 45° C. for 30 min then cooled slowly to 15° C. The solids were filtered and washed with cold (15° C.) water (2×300 mL), providing 3-hydroxymethyl-2-methyl phenol. $^1$H-NMR (400 MHz, DMSO-d$_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 min during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol. $^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C: 5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 min then heated to 145° C. to obtain a homogeneous solution. The solution was aged at 145° C. for 2 h, then the reaction mixture was cooled to 95° C. 41.5 mL water was added (sparged with N$_2$), and the reaction aged for 20 h. The reaction was cooled to rt then the solids filtered through SOLKA FLOK and the cake washed with 50 mL DMF. To a 3 L flask containing 1 L EtOAc was added the DMF filtrate. A precipitate coating formed in bottom of flask. The DMF/EtOAc suspension was filtered through SOLKA FLOK and the cake was washed with 250 mL EtOAc. The resulting filtrate was washed with 5% brine solution (3×500 mL). The aqueous layers were extracted with 500 mL EtOAc and the combined organics were dried over MgSO4, fitered and evaporated. The solids were slurried in 250 mL MTBE at rt then filtered and washed with 100 mL MTBE. The solids were dried under vacuum at rt, providing 5-hydroxy-4-methyl-3H-isobenzofuran-1-one. $^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: 4-methyl-1-oxo-1,3-dihydroisobenzofuran-5-yl trifluoromethanesulfonate

5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 min, keeping the temperature <10° C. After stirring the reaction mixture for an additional 15 min, the reaction mixture was quenched with water (200 mL), then stirred with DARCO® KB (activated carbon, 25 g) for 15 min. The biphasic mixture was filtered over Solka floc, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, the solid washed with heptane and dried under vacuum and nitrogen, providing trifluoromethanesulfonic acid 4-methyl-1-oxo-1,3-dihydro-isobenzofuran-5-yl ester. $^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H)

Step E: 5-(1-Butoxy-vinyl)-4-methyl-3H-isobenzofuran-1-one

To a 1 L 3-neck round bottom flask was charged trifluoromethanesulfonic acid 4-methyl-1-oxo-1,3-dihydro-isobenzofuran-5-yl ester (63.0 g, 213 mmol), DMF (315 mL), butyl vinyl ether (138 mL, 1063 mmol)) then Et$_3$N (35.6 mL, 255 mmol). The solution was sparged with N$_2$ for 20 min. To the solution was added Pd(OAc)$_2$ (1.19 g., 5.32 mmol) and DPPP (2.41 g., 5.85 mmol) and sparged for an additional 10 min then heated to 80° C. After a 1 hr age, the solution was cooled to <10° C. then quenched with 630 mL EtOAc and washed with 5% NH$_4$Cl (2×315 mL), 10% brine (2×315 mL), dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one. $^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H)

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portion-wise while maintaining Tmax=19° C. The solution was then warmed to rt for 30 minutes. HBr (48%, 0.241 mL) was added and the reaction was aged at rt for approximately 1 h after which 236 mL water was then added to the batch. A water bath is used to maintain temp at 20° C. Another 315 mL of water was added (solvent composition 1:2 THF:water) and the slurry was cooled to 15° C. The resulting solids were filtered and washed with cold 1:2 THF:water (15° C.): 150 mL displacement wash followed by 100 mL slurry wash. The solids were dried under vacuum at rt to provide 5-(2-bromo-acetyl)-4-methyl-3H-isobenzofuran-1-one. $^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H)

Step G: 4-methyl-5-[(2R)-oxiran-2-yl]-2-benzofuran-1(3H)-one 5-(2-Bromo-acetyl)-4-methyl-3H-isobenzofuran-1-one (48.8 g., 181 mmol) was charged to a 5 L 3 neck round bottom equipped with overhead stirrer, thermocouple, and heating mantle. 2-Propanol (1.22 L) was added, followed by 610 mL of pH 7 0.1M potassium phosphate buffer. Buffer solution (610 mL) was charged to a 1.0 L erlenmeyer, and 2.44 g of NADP was added to the erlenmeyer and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the erlenmeyer flask and the mixture was swirled to dissolve the solids. The resulting solution was added to the 5 L round bottom, which was then heated to 28° C. and aged for 6 hours, at which point the reaction was cooled to rt and triethylamine (50.2 mL, 360 mmol) was added. The resulting solution was aged at 40° C. for 1 h. The light slurry solution was cooled to rt, after which 122 g NaCl was added. The solution was aged at rt then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at rt then filtered and washed w/5:1 Hexanes:IPAc solution (150 mL). The crystalline solids were dried under vacuum at rt to provide 4-methyl-5-[(2R)-oxiran-2-yl]-2-benzofuran-1 (3H)-one. $^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

Intermediate 3A and 3B

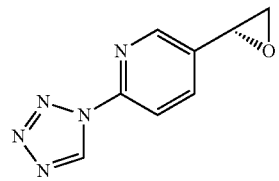

3A

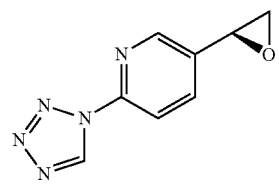

3B (S)-5-(Oxiran-2-yl)-2-(1H-tetrazol-1-yl)pyridine (3A) and (R)-5-(Oxiran-2-yl)-2-(1H-tetrazol-1-yl)pyridine (3B)

Step A: 5-Bromo-2-(1H-tetrazol-1-yl)pyridine

To a solution of 5-bromopyridin-2-amine (5.0 g, 28.9 mmol) in acetic acid (40 ml, 699 mmol) was added (di-ethoxymethoxy) ethane (7.70 ml, 46.2 mmol), followed by sodium azide (2.82 g, 43.3 mmol). The mixture was heated at 80° C. for 1 h, cooled to room temperature and diluted with water. Precipitate was collected by filtration and dried under high vacuum to provide the title compound.

Step B: 5-Ethenyl-2-(1H-tetrazol-1-yl)pyridine

To a stirring solution of 5-bromo-2-(1H-tetrazol-1-yl) pyridine (1.0 g, 4.42 mmol), in EtOH (70 mL) was added bis[(diphenylphosphino)ferrocene]dichloropalladium(II), complex with dichloromethane (0.361 g, 0.442 mmol), potassium vinyl trifluoroborate (1.18 g, 8.85 mmol, 2 equiv.), triethylamine (1.23 mL, 8.85 mmol, 2 equiv), and water (0.5 mL). The reaction mixture was heated at reflux (90° C., oil bath) under $N_2$. Upon completion (1-2 h) as determined by reverse phase HPLC-MS and TLC (eluent: 10% ethyl acetate in hexane), the mixture was cooled to room temperature, and then diluted with water. The organic layer was separated, and the aqueous layer was extracted with EtOAc. The combined organic layers were washed with brine, dried over $MgSO_4$, and concentrated. The crude material was chromatographed over a column of $SiO_2$ (0-20% EtOAc in hexane as eluent). Evaporation of the solvent yielded the title compound. LCMS $[M+1]^+=174.0$.

Step C: 5-(Oxiran-2-yl)-2-(1H-tetrazol-1-yl)pyridine

To a solution of 5-ethenyl-2-(1H-tetrazol-1-yl)pyridine (0.664 g, 3.83 mmol) in a 2:1 ratio of $H_2O$:t-BuOH (30 mL) was added N-bromosuccinimide (0.751 g, 4.22 mmol) in portions over 5 min. The mixture was heated at 40° C. for 1 h, cooled to 5° C., made basic with sodium hydroxide aqueous solution (0.46 g in 5 mL of $H_2O$, 11.50 mmol), stirred for another 1 h at the same temperature, and poured into $H_2O$ (10 mL). The product precipitated out. The solid was collected by filtration, washed with water, and dried in vacuo. $^1H$ NMR (500 MHz, DMSO-$d_6$), δ 10.17 (s, 1H), 8.60 (d, J=1.4 Hz, 1H), 8.04-7.99 (m, 2H), 4.14 (dd, J=2.7 Hz, J=2.8 Hz, 1H), 3.23 (t, J=4.6 Hz, 1H), 3.02 (dd, J=25 Hz, 1H); LCMS $[M+1]^+=190$. Further chiral separation (AD-H 30×250 mm, 50% MeOH/$CO_2$, 70 mL/min, 100 bar, 46 mg in MeOH/DCM) afforded faster eluted 3A (S)-5-(oxiran-2-yl)-2-1H-tetrazol-1-yl)pyridine and slower eluted 3B (R)-5-(oxiran-2-yl)-2-(1H-tetrazol-1-yl)pyridine The following epoxide intermediates in Table 1 were prepared employing a similar synthetic method as that described for Intermediates 3A and 3B. In some cases a different chiral HPLC column was used for separation of the enantiomeric epoxides. The absolute stereochemistry of the compounds in Table 1 was not unambiguously established; however, both isomeric intermediates were useful for making potent ROMK inhibitors.

TABLE 1

Epoxides prepared in a similar fashion as described for 3A and 3B.

| No. | Starting material | Structure and name | Structure and name | LC-MS $[M + 1]^+$ |
|---|---|---|---|---|
| 4 | (structure with $NH_2$, N, Br) | Fast eluted 4A | Slow eluted 4B | 190.10 |
| 5 | (structure with Br, N, $NH_2$) | Fast eluted 5A | Slow eluted 5B | 188.10 ($[M + 1 - 28]^+$) |
| 6 | (structure with Cl, N, N, $NH_2$) | Fast eluted 6A | Slow eluted 6B | 191.16 |
| 7 | (structure with Br, N, F, $NH_2$) | Fast eluted 7A | Slow eluted 7B | 208.12 |

TABLE 1-continued

Epoxides prepared in a similar fashion as described for 3A and 3B.

| No. | Starting material | Structure and name | Structure and name | LC-MS [M + 1]+ |
|---|---|---|---|---|
| 8 | (NH2, pyridine with Me, Br) | Fast eluted 8A | Slow eluted 8B | 204.12 |
| 9 | (Br, Me, NH2 benzene) | Fast eluted 9A | Slow eluted 9B | 203.1 |
| 10 | (Br, F, NH2 benzene) | Fast eluted 10A | Slow eluted 10B | 207.3 |

Intermediate 11

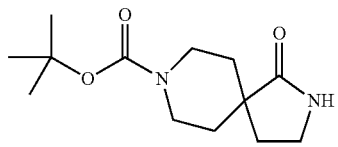 [SMILES: CC(C)(C)OC(=O)N1CCC2(CCNC2=O)CC1]

tert-Butyl 1-oxo-2,8-diazaspiro[4.5]decane-8-carboxylate

Step A: Methyl piperidine-4-carboxylate

To a solution of piperidine-4-carboxylic acid (1000 g, 7.75 mol) in MeOH (8000 mL) was added SOCl₂ (1000 mL) at 0° C. The mixture was stirred at rt for 18 h and concentrated to give the title compound. ¹H-NMR (400 MHz, CD₃OD) δ 3.74 (s, 3H), 3.43-3.35 (m, 2H), 3.12-3.06 (m, 2H), 2.81-2.74 (m, 1H), 2.20-2.15 (m, 2H), 1.95-1.85 (m, 2H).

Step B: 1-tert-Butyl 4-methyl piperidine-1,4-dicarboxylate

To a solution of methyl piperidine-4-carboxylate (1400 g, 7.75 mol) in DCM (8000 mL) was added NaHCO₃ (1953 g, 23.21 mol) and Boc₂O (2030 g, 9.3 mol) dropwise at 0° C. The mixture was stirred at rt for 18 h, and was filtered. The filtrate was concentrated in vacuo to give the title compound. ¹H-NMR (400 MHz, CDCl₃) δ 4.100-3.90 (m, 2H), 3.68 (s, 3H), 2.85-2.79 (m, 2H), 2.47-2.41 (m, 1H), 1.88-1.80 (m, 2H), 1.66-1.52 (m, 2H), 1.47 (s, 9H).

Step C: 1-tert-Butyl 4-methyl 4-(cyanomethyl)piperidine-1,4-dicarboxylate

LDA [prepared from n-BuLi (2.5 M, 420 mL) and diisopropylamine (128 g, 1.07 mol) in THF (300 mL)] was added dropwise to a solution of 1-tert-butyl 4-methyl piperidine-1,4-dicarboxylate (185 g, 761.3 mmol) in THF (1200 mL) at −70° C. under N₂. The mixture was stirred at −70° C. for 1.5 h, and to this mixture was added a solution of bromoacetonitrile (128 g, 1.12 mol) in THF (300 mL) at −70° C. Stirring continued at −70° C. for 1 h and at 20° C. for 18 h. The resulting mixture was quenched with H₂O. The organic layer was separated, and the aqueous layer was extracted with EtOAc (500 mL×3). The combined organic extracts were dried over Na₂SO₄ and concentrated. The residue was purified by silica gel chromatography eluted with PE/EA (5:1) to give the title compound. ¹H-NMR (400 MHz, CDCl₃) δ 3.90-3.75 (m, 5H), 3.12-3.00 (m, 2H), 2.61-2.56 (m, 2H), 2.19-2.1 (m, 2H), 1.59-1.50 (m, 2H), 1.40 (s, 9H).

Step D: tert-Butyl 1-oxo-2,8-diazaspiro[4.5]decane-8-carboxylate

To a solution of 1-tert-butyl 4-methyl 4-(cyanomethyl) piperidine-1,4-dicarboxylate (350 g, 1.2 mol) in MeOH (6000 mL) were added NH₃·H₂O (400 mL) and Raney-Ni (300 g) at rt. The mixture was stirred under 2 MPa of hydrogen at 50° C. for 18 h, and filtered. The filtrate was concentrated. The crude product was washed with EtOAc to give the title compound. ¹H-NMR (400 MHz, CDCl₃) δ 6.30 (s, 1H), 4.08-3.92 (m, 2H), 3.38-3.30 (m, 2H), 3.01-2.91 (m, 2H), 2.10-2.00 (m, 2H), 1.88-1.78 (m, 2H), 1.49-1.32 (m, 11H).

Intermediate 12

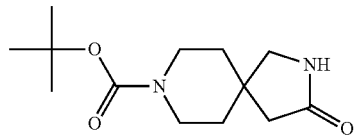 [SMILES: CC(C)(C)OC(=O)N1CCC2(CC1)CNC(=O)C2]

3-oxo-2,8-diaza-spiro[4,5]decane-8-carboxylic acid tert-butyl ester

Step A: tert-butyl 4-(2-ethoxy-2-oxoethylidene)piperidine-1-carboxylate

Into a 10-L 4-necked round-bottom flask purged and maintained with an inert atmosphere of nitrogen was placed a suspension of NaH (74.0 g, 2.16 mol 1.05 equiv, 70%) in tetrahydrofuran (2000 mL) at 0° C., then ethyl 2-(diethoxyphosphoryl)acetate (514 g, 2.06 mol, 1.05 equiv, 98%) was added dropwise with stirring at 0° C. This was followed by the addition of a solution of tert-butyl 4-oxopiperidine-1-carboxylate (400 g, 1.97 mol, 1.00 equiv, 98%) in tetrahydrofuran (1200 mL) dropwise with stirring at 0° C. The resulting solution was stirred for 60 min at room temperature, then was quenched by the addition of 2000 mL of water. The resulting solution was extracted with 2×1000 mL of ethyl acetate. The organic layers were combined, dried over anhydrous magnesium sulfate and concentrated under vacuum. The residue was washed with 1×1000 mL of hexane and dried to afford tert-butyl 4-(2-ethoxy-2-oxoethylidene)piperidine-1-carboxylate.

Step B: tert-butyl 4-(2-ethoxy-2-oxoethyl)-4-(nitromethyl)piperidine-1-carboxylate Into a 3000-mL 4-necked round-bottom flask was placed potassium carbonate (93.2 g, 662 mmol, 0.50 equiv) and DMSO (2000 mL). The resulting solution was heated to 80° C. This was followed by the addition of tert-butyl 4-(2-ethoxy-2-oxoethylidene)piperidine-1-carboxylate (368 g, 1.30 mol, 1.00 equiv, 95%) and CH₃NO₂ (417 g, 6.70 mol, 5.00 equiv, 98%) slowly. The resulting solution was stirred for 120 min at 90° C. After being cooled to room temperature, the reaction mixture was adjusted to ph 5 with HCl (0.5 mol/L) and diluted with 2000 mL of water. The resulting solution was extracted with 3×1500 mL of ether. The organic layers were combined, washed with 1×2000 mL of water and 1×2000 mL of saturated brine, dried and concentrated under vacuum. The residue was applied onto a silica gel column and eluted with ethyl acetate/petroleum ether (1:20-1:15-1:10) to afford the title compound.

Step C: 3-oxo-2,8-diaza-spiro[4,5]decane-8-carboxylic acid tert-butylester

A mixture of tert-butyl 4-(2-ethoxy-2-oxoethyl)-4-(nitromethyl)piperidine-1-carboxylate (330 g, 990 mmol, 1.00 equiv, 99%) and Ni (40 g, 0.15 equiv) in ethanol (1200 mL) was stirred for 24 h under a hydrogen atmosphere at room temperature. The solid was filtered out. The filtrate was concentrated under vacuum. The crude product was purified by re-crystallization from ether to afford the title compound. LC-MS (ES, m/z): 199 [M+H]⁺; H-NMR (400 MHz, CDCl₃, ppm): 1.447-1.476 (9H, s), 1.597-1.673 (4H, m, J=30.4 Hz), 2.235 (2H, s), 3.226 (2H, s), 3.284-3.348 (2H, m, J=25.6 Hz), 3.507-3.567 (2H, m, J=24 Hz), 6.048 (1H, s).

Intermediate 13

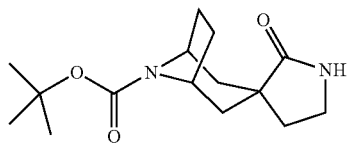 [SMILES: CC(C)(C)OC(=O)N1C2CCC1CC1(CCNC1=O)C2]

(1R,3r,5S)-tert-Butyl 2'-oxo-8-azaspiro[bicyclo [3.2.1]octane-3,3'-pyrrolidine]-8-carboxylate Step A: (1R,3s,5S)-8-tert-butyl 3-methyl 8-azabicyclo[3.2.1]octane-3,8-dicarboxylate To a solution of (1R,3s,5S)-8-(tert-butoxycarbonyl)-8-azabicyclo[3.2.1]octane-3-carboxylic acid (5.0 g, 19.58 mmol) in a solvent mixture of dry MeOH (60 ml) and DCM (60.0 ml) was added (trimethylsilyl)diazomethane (19.58 ml, 39.2 mmol). The mixture was stirred for 0.5 hr, and AcOH (5 ml) was added. Volatiles were removed under reduced pressure. The residue was dissolved in EtOAc, and the solution was washed with saturated NaHCO₃ and brine, and dried over MgSO₄. The solvent was removed to give a solid which was used in the next step without further purification. LCMS [M+1-56]⁺=214.1

Step B: (1R,3r,5S)-8-tert-Butyl 3-methyl 3-(cyanomethyl)-8-azabicyclo[3.2.1]octane-3,8-dicarboxylate To a solution of (1R,3r,5S)-8-tert-butyl 3-methyl 8-azabicyclo[3.2.1]octane-3,8-dicarboxylate (5 g, 18.6 mmol) in THF (100 mL) was added LDA (13.9 mL, 27.8 mmol) at −78° C. The mixture was stirred at the same temperature for 30 min, then to this mixture was added bromoacetonitrile (1.94 mL, 27.8 mmol) in THF (15 ml) by injection. The resulting mixture was stirred at −78° C. for 15 min, quenched with saturated KHSO₄ at −78° C., warmed up to rt and diluted with ether (100 mL). The organic layer was separated, and the aqueous layer was extracted with ether (50 mL). The combined organic layers were washed with brine, dried (MgSO₄), and concentrated. The residue was purified by column (silica gel 120 g, EtOAc-Hexane-0-50% gradient, then 50% EtOAc. ¹H-NMR (500 MHz, CDCl₃): δ ppm 4.18 (1H, m), 4.27 (1H, m), 3.83 (3H, s), 2.58 (2H, m), 2.43 (2H, m), 1.55-1.95 (6H, m), 1.50 (9H, s). LCMS [M+1-100]⁺=209.2.

Step C: (1R,3r,5S)-8-tert-Butyl3-methyl 3-(2-aminoethyl)-8-azabicyclo[3.2.1]octane-3,8-dicarboxylate To a solution of (1R,3r,5S)-8-tert-butyl 3-methyl 3-(cyanomethyl)-8-azabicyclo[3.2.1]octane-3,8-dicarboxylate (4.0 g, 12.97 mmol) in ethanol (20 ml) and AcOH (20 ml) was added platinum(IV) oxide (0.295 g, 1.30 mmol). The mixture was hydrogenated on a shaker (45 psi hydrogen) at rt for 24 hr. The catalyst was filtered off through a CELITE pad, and the filtrate was concentrated. The crude material was used in the next step without further purification. LCMS [M+1]$^+$=313.20; [M+1-56]$^+$=257.1.

Step D: (1R,3r,5S)-tert-Butyl 2'-oxo-8-azaspiro[bicyclo[3.2.1]octane-3,3'-pyrrolidine]-8-carboxylate A mixture of (1R,3r,5S)-8-tert-butyl 3-methyl 3-(2-aminoethyl)-8-azabicyclo[3.2.1]octane-3,8-dicarboxylate (4.2 g, 13.44 mmol) and potassium carbonate (9.29 g, 67.2 mmol) in MeOH (50 ml) was heated at 60° C. for 1 hr. The resulting mixture was concentrated, and diluted with DCM (50 ml). The suspension was filtered through a silica gel pad. The filtrate was concentrated to give the title compound. $^1$H-NMR (500 MHz, CDCl$_3$): δ ppm 5.95 (1H, bs), 4.30 (1H, m), 4.20 (1H, m), 3.26 (2H, t, J=7.0 Hz), 1.75-2.15 (6H, m), 1.47 (9H, s). LCMS [M+1]$^+$=281.15; [M+1-56]$^+$=225.1.

Intermediate 14

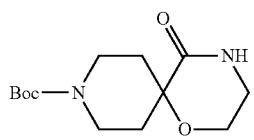

tert-butyl 5-oxo-1-oxa-4,9-diazaspiro[5.5]undecane-9-carboxylate

Step A: 1-tert-butyl 4-methyl 4-(allyloxy)piperidine-1,4-dicarboxylate

NaH (0.92 g, 15.4 mol, 60% dispersion in mineral oil) was added the five portions to a stirred solution of compound 1-tert-butyl 4-methyl 4-hydroxypiperidine-1,4-dicarboxylate (2 g, 7.7 mmol) being cooled to 0° C. in DMF (20 mL). After the mixture was stirred at 0° C., the 3-allyl bromide (1.2 g, 10 mmol) was added, dropwise. The mixture was stirred at rt for 16 h. The reaction mixture was quenched by the addition of the saturated aqueous NH$_4$Cl and evaporated to afford the crude product. The crude product was purified by column chromatography on silica gel eluted with (PE/EA 50:1→30:1→15:1) to give the title compound.

Step B: 1-tert-butyl 4-methyl 4-(2-oxoethoxy)piperidine-1,4-dicarboxylate

To a solution of 1-tert-butyl 4-methyl 4-(allyloxy)piperidine-1,4-dicarboxylate (1.2 g, 4 mmol) in MeOH (30 mL) was added osmium tetroxide (30 uL, 0.006 mmol, 0.81 g/mL H$_2$O) and sodium periodate (16 ml, 16 mmol, 1M). The mixture was allowed to stir at rt for 16 hours. The mixture was quenched with Na$_2$S$_2$O$_3$ (50 mg), extracted with ethyl acetate (20 mL×3), dried over Na$_2$SO$_4$ and concentrated to afford the crude product, which was further purified by column chromatography on silica gel eluted with (PE/EA 20:1→10:1→5:1→1:1) to give the title compound.

Step C: 1-tert-butyl 4-methyl 4-(2-(dibenzylamino)ethoxy)piperidine-1,4-dicarboxylate To a stirred solution of 1-tert-butyl 4-methyl 4-(2-oxoethoxy)piperidine-1,4-dicarboxylate (0.3 g, 1 mmol) in DCE (5 mL) was added dibenzyl amine (0.3 g, 1.5 mmol), the resultant mixture was stirred at room temperature for 1 h. Then sodium triacetoxyborohydride (0.42 g, 2 mmol) was added to the reaction mixture, the reaction mixture was stirred for further 4 h at room temperature. The mixture was quenched with water (5 mL), extracted with DCM (5 mL×3), the combined organic portions were concentrated and purified by column chromatography gel eluted with (PE/EA 5:1→2:1→1:1) to give the title compound.

Step D: tert-butyl 5-oxo-1-oxa-4,9-diazaspiro[5.5]undecane-9-carboxylate

A mixture of 1-tert-butyl 4-methyl 4-(2-(dibenzylamino)ethoxy)piperidine-1,4-dicarboxylate (290 mg, 0.6 mmol) and 10% palladium hydroxide on carbon (20%, w/w, 30 mg) in MeOH (10 mL) was hydrogenated under 40 psi of Hydrogen at 30° C. overnight. Then the mixture was cooled to room temperature and the catalyst was filtered off. The filtrate was concentrated in vacuo to give title compound.

Intermediate 15

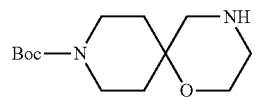

tert-Butyl 1-oxa-4,9-diazaspiro[5.5]undecane-9-carboxylate

Step A: tert-Butyl 4-oxopiperidine-1-carboxylate

To a solution of piperidin-4-one (1.0 mol, 100.0 g) and NaHCO$_3$ (1.6 mmol, 100 g) in H$_2$O (1000 mL) was added (BOC)$_2$O (1.2 mol, 191.6 g), the reaction was stirred at 50° C. overnight. The residue was extracted with EtOAc (3×400 mL) and the combined organic layers were washed with brine, dried over Na$_2$SO$_4$, filtered and concentrated to give tert-butyl 4-oxopiperidine-1-carboxylate. $^1$H NMR (300 MHz, CDCl$_3$) δ: 1.49 (s, 9H), 2.43 (t, J$_1$=6.0 Hz, J$_2$=6.0 Hz, 4H), 3.71 (t, J$_1$=6.0 Hz, J$_2$=6.0 Hz, 4H).

Step B: tert-Butyl 4-hydroxy-4-(nitromethyl)piperidine-1-carboxylate

To a mixture of tert-butyl 4-oxopiperidine-1-carboxylate (0.1 mol) and nitro-methane (0.1 mol) in methanol (200 mL) was added sodium methanolate (0.11 mol) at rt and the reaction was stirred for 1 h at room temperature. The solvent was evaporated. The residue was taken up into water, neutralized with acetic acid, extracted twice with EtOAc. The separated organic layer was washed with water, dried, filtered and evaporated to get tert-butyl 4-hydroxy-4-(nitromethyl)piperidine-1-carboxylate. $^1$H NMR (300 MHz, CDCl$_3$) δ: 1.46 (s, 9H), 1.61 (t, J$_1$=5.4 Hz, J$_2$=5.4 Hz, 4H), 2.92 (s, 1H) 3.19 (t, J$_1$=12.0 Hz, J$_2$=12.0 Hz, 2H) 3.94 (t, J$_1$=6.9 Hz, J$_2$=6.9 Hz, 2H) 4.43 (s, 2H).

Step C: tert-Butyl 4-(aminomethyl)-4-hydroxypiperidine-1-carboxylate

The mixture of tert-butyl 4-hydroxy-4-(nitromethyl)piperidine-1-carboxylate (15.0 g, 0.058 mol) and acetic acid (12 mL) in methanol (180 mL) was hydrogenated at rt with palladium-on-carbon (10%, 1.5 g) as a catalyst. After uptake of hydrogen, the catalyst was filtered off and the filtrate was evaporated. The residue was taken up into ice water, alkalized with potassium hydroxide, extracted twice with EtOAc, dried over $Na_2SO_4$, filtered and concentrated to give tert-butyl 4-(aminomethyl)-4-hydroxypiperidine-1-carboxylate.

Step D: tert-Butyl 4-((2-chloroacetamido)methyl)-4-hydroxypiperidine-1-carboxylate The mixture of tert-butyl 4-(aminomethyl)-4-hydroxypiperidine-1-carboxylate (10.0 g, 45 mmol), chloroacetyl chloride (6 mL, 64 mmol) and $K_2CO_3$ (14.0 g, 95 mmol) in $EtOAc/H_2O$ (100 mL/100 mL) was stirred for 1 h at 0° C. The crude mixture was extracted with EtOAc (2×300 mL). The combined organics were dried over $Na_2SO_4$, filtered and concentrated in vacuo to give tert-butyl 4-((2-chloroacetamido)methyl)-4-hydroxypiperidine-1-carboxylate. $^1$H NMR (300 MHz, $CDCl_3$) δ: 1.45 (s, 9H), 1.53 (d, 4H), 2.59 (s, 1H) 3.21 (s, 2H) 3.35 (s, 2H), 3.78 (d, J=18.0 Hz, 2H) 4.13 (s, 2H), 6.99 (s, 1H).

Step E: tert-Butyl 3-oxo-1-oxa-4,9-diazaspiro[5.5]undecane-9-carboxylate

To a mixture of potassium tert-butoxide (31.8 g, 283 mmol) and tert-butanol (500 mL) was added tert-butyl 4-((2-chloroacetamido)methyl)-4-hydroxypiperidine-1-carboxylate (41.9 g, 141 mmol) in THF (300 mL) over 40 minutes and the resulting mixture was continued to stir for 1 h at room temperature before it was concentrated. The residue was diluted with EtOAc and water, the organic layer was separated, washed with brine, and concentrated to provide tert-butyl 3-oxo-1-oxa-4,9-diazaspiro[5.5]undecane-9-carboxylate. $^1$H NMR (300 MHz, $CDCl_3$) δ: 1.41 (s, 9H), 1.52 (s, 2H), 1.90 (d, J=12.0 Hz, 2H), 2.59 (s, 1H). 12 (m, 2H), 3.25 (s, 2H) 3.84 (d, J=6.4 Hz, 2H) 4.17 (s, 2H), 6.12 (s, 1H)

Step F: tert-Butyl 1-oxa-4,9-diazaspiro[5.5]undecane-9-carboxylate

To a solution of tert-butyl 3-oxo-1-oxa-4,9-diazaspiro[5.5]undecane-9-carboxylate (16.0 g, 60 mmol) in THF (70 mL) was added tetrahydrofuran-borane (250 mL, 250 mmol) at room temperature. The reaction mixture was refluxed for 2 h and the solvent was removed under the reduced pressure. To the resulting mixture was added MeOH and $N_1,N_1,N_2,N_2$-tetramethylethane-1,2-diamine and the reaction was stirred at 78° C. overnight. The reaction was concentrated and the residue was diluted with EtOAc and water. The organic layer was separated, washed with brine, and concentrated in vacuo to give tert-butyl 1-oxa-4,9-diazaspiro[5.5]undecane-9-carboxylate. $^1$H NMR (300 MHz, $CDCl_3$) δ: 1.45 (s, 9H), 1.61 (s, 2H), 1.93 (d, J=12.0 Hz, 2H), 2.67 (s, 2H) 2.83 (m, 2H), 3.16 (t, $J_1$=9.0 Hz, $J_2$=12.0 Hz, 2H) 3.65 (m, 4H).

Intermediate 16

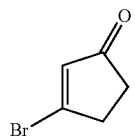

3-bromocyclopent-2-enone

Dibromotriphenyl-phosphorane (25.8 g, 61.2 mmol) was stirred in benzene (150 mL) for 20 mins under nitrogen before adding TEA (8.67 mL, 62.2 mmol) and 1,3 cyclopentadione (5.0 g, 51 mmol). The mixture was stirred at rt for 16 hrs. The reaction was filtered then concentrated and chromatographed through 330 g ISCO Redi-sep column using ethyl acetate:hexane (50:50) to yield 3-bromocyclopent-2-enone. LC-MS (IE, m/z): 162[M+1]$^+$; $^1$H-NMR (600 MHz, $CDCl_3$) δ ppm 6.414 (s, 1H), 2.989 (t, J=1.8 Hz, 1H), 2.976 (t, J=1.8 Hz, 1H), 2.538-2.555 (m, 2H).

Intermediate 17

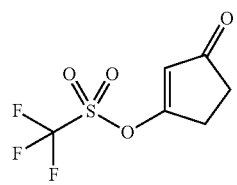

3-Oxocyclopent-1-enyl trifluoromethanesulfonate

To a solution of 1,3 cyclopentadione (2.5 g, 25.5 mmol) in DCM (50 mL) at −78° C. was added 2,6-lutidine (4.45 ml, 38 mmol), followed by triflic anhydride (5.14 mL, 30.6 mmol) dropwise. The reaction temperature was maintained at −78° C. for 0.5 h before warmed to rt for 1 h. The mixture was washed with 1 N HCl (10 mL), and NaHCO3 (5 mL—diluted solution), dried over $Na_2SO_4$, concentrated to give the title compound. LC-MS (IE, m/z): 231 [M+1]$^+$.

Intermediate 18

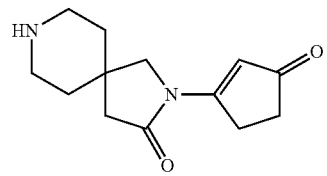 [SMILES: O=C1C=C(N2CC3(CCNCC3)CC2=O)CC1]

2-(3-Oxocyclopent-1-enyl)-2,8-diazaspiro[4.5]decan-3-one

Step A: tert-butyl 3-oxo-2-(3-oxocyclopent-1-en-1-yl)-2,8-diazaspiro[4.5]decane-8-carboxylate To tert-butyl 3-oxo-2,8-diazaspiro[4.5]decane-8-carboxylate (300 mg, 1.18 mmol) in toluene (5 ml) was added 3-bromocyclopent-2-enone (228 mg, 1.42 mmol), XANTPHOS (68.3 mg, 0.118 mmol), palladium(II) acetate (13 mg, 0.059 mmol), $K_2CO_3$ (326 mg, 2.36 mmol) and water (0.0638 mL, 3.54 mmol). The reaction was heated at 60° C. for 4 hrs then filtered thru CELITE and concentrated. The residue was chromatographed through 40 g ISCO Redi-sep column and eluted with 50%-100% ETOAc: in hexane to yield the title compound. $^1$H-NMR (500 MHz, $CDCl_3$) δ ppm 5.574 (s, 1H), 3.624-3651 (m, 2H), 3.520 (s, 2H), 3.328

(t, J=6.0 Hz, 1H), 3.300 (t, J=6.0 Hz, 1H), 3.235-3.255 (m, 2H), 2.543 (s, 2H), 2.472-2.492 (m, 2H), 1.671 (t, J=5.5 Hz, 4H), 1.495 (s, 9H).

Step B: 2-(3-oxocyclopent-1-en-1-yl)-2,8-diazaspiro[4.5]decan-3-one tert-Butyl 3-oxo-2-(3-oxocyclopent-1-en-1-yl)-2,8-diazaspiro[4.5]decane-8-carboxylate (380 mg, 1.14 mmol) was stirred at rt in TFA (4 mL, 52 mmol) for 1 hr. Excess TFA was removed under vacuum. Ethanol was added and the product precipitated out. Filtered to get 2-(3-oxocyclopent-1-en-1-yl)-2,8-diazaspiro[4.5]decan-3-one trifluoroacetate salt. LC-MS (IE, m/z): 235[M+1]$^+$.

Intermediate 19

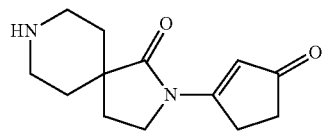

2-(3-oxocyclopent-1-enyl)-2,8-diazaspiro[4.5]decan-1-one

The intermediate was prepared following the same procedure as Intermediate 18 (above) from 3-bromocyclopent-2-enone and tert-butyl 1-oxo-2,8-diazaspiro[4.5]decane-8-carboxylate. LC-MS (IE, m/z): 235 [M+1]$^+$.

Intermediate 20

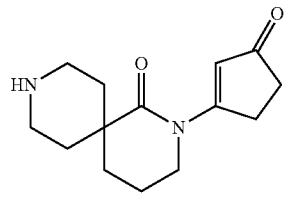 [SMILES: O=C1C=C(N2CCCC3(CCNCC3)C2=O)CC1]

2-(3-Oxocyclopent-1-enyl)-2,9-diazaspiro[5.5]undecan-1-one

The title compound was prepared following the same procedure as Intermediate 18 (above) from 3-Oxocyclopent-1-enyl trifluoromethanesulfonate and tert-butyl 1-oxo-2,9-diazaspiro[5.5]undecane-9-carboxylate. LC-MS (IE, m/z): 264 [M+1]$^+$ Intermediate 21

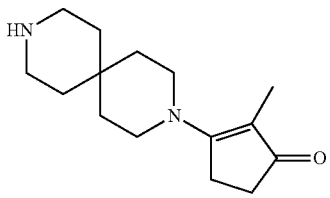 [SMILES: CC1=C(N2CCC3(CCNCC3)CC2)CCC1=O]

2-methyl-3-(3,9-diazaspiro[5.5]undecan-3-yl)cyclopent-2-enone

Step A: tert-butyl 9-(2-methyl-3-oxocyclopent-1-enyl)-3,9-diazaspiro[5.5]undecane-3-carboxylate To tert-butyl 3,9-diazaspiro[5.5]undecane-3-carboxylate (119 mg, 0.468 mmol) in a microwave tube was added 2-propanol (7 ml) followed by 2-methyl-1,3-cyclopentadione (62.9 mg, 0.561 mmol). The tube was sealed and heated at 120° C. for 16 hrs. The reaction was concentrated and taken up with ethyl acetate then washed with saturated NaHCO$_3$. The organic layer was dried over Na$_2$SO$_4$ filtered and concentrated to yield title compound. LC-MS (IE, m/z): 349 [M+1]$^+$ Step B: 2-methyl-3-(3,9-diazaspiro[5.5]undecan-3-yl)cyclopent-2-enone tert-Butyl 9-(2-methyl-3-oxocyclopent-1-enyl)-3,9-diazaspiro [5.5] undecane-3-carboxylate (275 mg, 0.789 mmol) was stirred in TFA (2 ml) for 1 hr. LC-MS showed only unprotected product. Concentrated then took up the residue in 1 ml MeOH and passed thru a Agilent bond elut 10 g/60 ml column. Washed with MeOH (1 CV) then eluted with 10% NH$_4$OH/MeOH (2 CV) to yield the title compound (80 mg, 0.322 mmol). LC-MS (IE, m/z): 249 [M+1]$^+$; $^1$H-NMR (500 MHz, CD$_3$OD) δ ppm 3.641 (t, J=5.4 Hz, 4H), 2.982 (t, J=5.6 Hz, 4H), 2.609 (m, 2H), 2.319 (m, 2H), 1.847 (s, 3H), 1.649 (t, J=5.7 Hz, 4H), 1.611 (t, J=5.6 Hz, 4H).

Intermediate 22

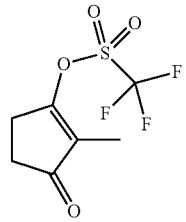

2-methyl-3-oxocyclopent-1-en-1-yl trifluoromethanesulfonate

To a solution of 2-methyl-1,3-cyclopentanedione (1000 mg, 8.92 mmol) in DCM (40 mL) at −78° C. was added 2,6-lutidine (1.558 mL, 13.38 mmol) followed by triflic anhydride (1.80 mL, 10.7 mmol) dropwise. The reaction temperature was maintained at −78° C. for 0.5 h before warming to room temperature for 1 h. The reaction mixture was washed with 1N HCl (10 mL), and dilute aqueous NaHCO$_3$ (5 mL), dried over Na$_2$SO$_4$, concentrated to give the title compound. LC-MS (IE, m/z): 245 [M+1]$^+$ Intermediate 23

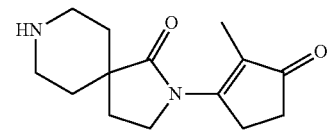 [SMILES: CC1=C(N2CCC3(CCNCC3)C2=O)CCC1=O]

2-(2-methyl-3-oxocyclopent-1-en-1-yl)-2,8-diazaspiro[4.5]decan-1-one tert-Butyl 1-oxo-2,8-diazaspiro[4.5]decane-8-carboxylate (1042 mg, 4.10 mmol) was dissolved in toluene (11.9 mL) with water (0.221 mL, 12.29 mmol) then added 2-methyl-3-oxocyclopent-1-en-1-yl trifluoromethanesulfonate (1000 mg, 4.10 mmol), XANTPHOS (237 mg, 0.410 mmol), palladium(II) acetate (46.0 mg, 0.205 mmol), and $K_2CO_3$ (1132 mg, 8.19 mmol). The mixture was heated at 60° C. for 16 hrs. The reaction was filtered through a CELITE and washed with ETOAc then purified by MPLC using 120 g ISCO Redi-sep column and 5% MeOH/DCM to yield tert-butyl 2-(2-methyl-3-oxocyclopent-1-en-1-yl)-1-oxo-2,8-diazaspiro[4.5]decane-8-carboxylate. It was then stirred at rt in TFA (6 mL, 78 mmol) for 1 hr. The reaction mixture was concentrated and loaded on an Agilent Bond elut 10 g SCX cartridge. The cartridge was washed first with MeOH (1 CV) then eluted with 7N $NH_3$ in methanol (3 CV). The eluent was concentrated to yield the title compound. LC-MS (IE, m/z): 249 $[M+1]^+$ Intermediate 24

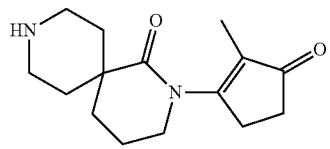

2-(2-Methyl-3-oxocyclopent-1-enyl)-2,9-diazaspiro[5.5]undecan-1-one

Step A: tert-butyl 2-(2-methyl-3-oxocyclopent-1-en-1-yl)-1-oxo-2,9-diazaspiro[5.5]undecane-9-carboxylate tert-butyl 2-(2-methyl-3-oxocyclopent-1-en-1-yl)-1-oxo-2,9-diazaspiro[5.5]undecane-9-carboxylate (110 mg, 0.410 mmol) was dissolved in toluene (3 ml) with water (0.022 ml, 1.229 mmol) then added 2-methyl-3-oxocyclopent-1-en-1-yl trifluoromethanesulfonate (100 mg, 0.41 mmol), XANTPHOS (24 mg, 0.041 mmol), palladium(II) acetate (4.60 mg, 0.020 mmol), and $K_2CO_3$ (113 mg, 0.82 mmol). The mixture was heated at 60° C. for 16 hrs. The reaction was filtered through a CELITE pad and washed with ETOAc then purified by MPLC using 40 g ISCO Redi-sep column and 5% MeOH/DCM to yield the title compound. $^1$H-NMR (500 MHz, $CDCl_3$) δ ppm 3.776 (b, 2H), 3.536 (t, J=6.0 Hz, 2H), 3.217-3.27 (m, 2H), 2.6915 (b, 2H), 2.468 (m, 2H), 2.061-2.116 (m, 2H), 1.971 (b, 2H), 1.889 (b, 2H), 1.560 (s, 3H), 1.501 (b, 2H), 1.445 (s, 9H).

Step B: 2-(2-Methyl-3-oxocyclopent-1-enyl)-2,9-diazaspiro[5.5]undecan-1-one tert-Butyl 2-(2-methyl-3-oxocyclopent-1-en-1-yl)-1-oxo-2,9-diazaspiro[5.5]undecane-9-carboxylate (150 mg, 0.397 mmol) was stirred at rt in TFA (4 ml). After ½ hr, the reaction mixture was concentrated then taken up with methanol and loaded into Elut SCX cartridge. The cartridge was washed with MeOH (1 CV) then eluted out with 2N $NH_3$ in MeOH (2 CV) then with 7N $NH_3$ in MeOH. Eluent was concentrated to yield the title compound. $^1$H-NMR (500 MHz, $CD_3OD$) δ ppm 3.598 (t, J=5.5 Hz, 2H), 3.117-3.143 (m, 2H), 2.957 (t, J=9.5 Hz, 2H), 2.735 (b, 2H), 2.471-2.490 (m, 2H), 2.119-2.174 (m, 2H), 1.946-2.009 (b, 4H), 1.632-1.660 (m, 2H), 1.53 (s, 3H).

Intermediate 25

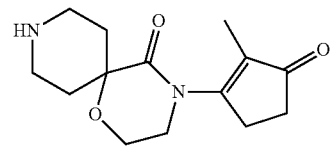 [SMILES: CC1=C(N2CCOC3(CCNCC3)C2=O)CCC1=O]

4-(2-methyl-3-oxocyclopent-1-en-1-yl)-1-oxa-4,9-diazaspiro[5.5]undecan-5-one

The title compounds was prepared in an analogous fashion to that described for 2-(2-Methyl-3-oxocyclopent-1-enyl)-2,9-diazaspiro[5.5]undecan-1-one (Intermediate 24), starting from 2-methyl-3-oxocyclopent-1-en-1-yl trifluoromethanesulfonate and tert-butyl 5-oxo-1-oxa-4,9-diazaspiro[5.5]undecane-9-carboxylate; LC-MS (IE, m/z): 265 $[M+1]^+$.

Intermediate 26 and enantiomers 29A (fast eluting) and 29B (slow eluting)

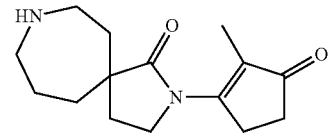 [SMILES: CC1=C(N2CCC3(CCCNCC3)C2=O)CCC1=O]

2-(2-Methyl-3-oxocyclopent-1-enyl)-2,8-diazaspiro[4.6]undecan-1-one

Step A: 1-tert-butyl 4-methyl 4-(cyanomethyl)azepane-1,4-dicarboxylate

Methyl azepane-4-carboxylate (2.05 g, 10.6 mmol) was stirred in a mixture of DCM (10 mL) and sat'd $NaHCO_3$ (20 mL) then added $BOC_2O$ (2.96 mL, 12.8 mmol). The mixture was stirred at rt for 2 hrs. Separated the DCM layer and washed with brine, dried over $Na_2SO_4$, filtered and concentrated to yield the title compound. $^1$H-NMR (600 MHz, $CDCl_3$) δ ppm 3.669 (d, J=5.3 Hz, 3H), 3.526-3.557 (m, 1H), 3.450-3.519 (m, 1H), 3.358-3.389 (m, 1H), 3.196-3.319 (m, 2H), 2.420-2.472 (m, 1H), 1.96-2.087 (m, 2H), 1.76-1.899 (m, 2H), 1.578-1.689 (m, 2H), 1.455 (s, 9H).

Step B: 1-tert-butyl 4-methyl 4-(cyanomethyl)azepane-1,4-dicarboxylate 1-tert-Butyl 4-methyl azepane-1,4-dicarboxylate (1.0 g, 3.89 mmol) was dissolved in THF (20 ml) and cooled to −78° C. then added LDA (2.91 ml, 5.83 mmol). Stirred for 30 mins, then added bromoacetonitrile (0.406 ml, 5.83 mmol) and kept at same temperature for 15 mins. Quenched with saturated $KHSO_4$ at −78° C. then warmed up to rt and diluted with ether. The organic layer was separated and the aqueous layer was extracted with more ether. The combined organic layers were dried over MgSO₄, and concentrated. The residue was chromatographed thru 120 g ISCO Redi-sep column using a solvent system of ETOAc:hexane (1:1) to yield the title compound. ¹H-NMR (500 MHz, CDCl₃) δ ppm 3.800 (s, 3H), 3.622-3.60 (m, 2H), 3.405-3.469 (m, 1H), 3.299-3.347 (m, 1H), 3.223-3.261 (m, 1H), 2.552-2.676 (m, 2H), 2.318 (m, 1H), 2.110-2.205 (m, 1H), 1.609-1.854 (m, 4H), 2.068 (s, 9H).

Step C: 1-tert-butyl 4-methyl 4-(2-aminoethyl)azepane-1,4-dicarboxylate 1-tert-Butyl 4-methyl 4-(cyanomethyl)azepane-1,4-dicarboxylate (3.6 g, 12.1 mmol) was dissolved in MeOH:Acetic Acid (50 ml:50 ml) and added platinum(IV) oxide (0.5 g, 2.2 mmol) then hydrogenated at 50 psi for 16 hrs. The catalyst was filtered off and the residue was concentrated to yield the title compound. LC-MS (IE, m/z): 301[M+1]⁺

Step D: tert-butyl 1-oxo-2,8-diazaspiro[4.6]undecane-8-carboxylate 1-tert-Butyl 4-methyl 4-(2-aminoethyl)azepane-1,4-dicarboxylate (3.65 g, 12.2 mmol) was dissolved in EtOH (200 mL) and added K₂CO₃ (6.72 g, 48.6 mmol) and heated at 90° C. for 16 hrs. The catalyst was filtered off and the ethanol was evaporated off. The reaction was taken up with brine and extracted with EtOAc (2×), dried over Na₂SO₄, filtered and then concentrated. The residue was purified by chromatography using 120 g ISCO Redi-sep column and eluted with 5% MeOH in DCM to yield title compound. LC-MS (IE, m/z): 291[M+23]⁺

Step E: 2-(2-Methyl-3-oxocyclopent-1-enyl)-2,8-diazaspiro[4.6]undecan-1-one (Isomer A and B)

To tert-butyl 1-oxo-2,8-diazaspiro[4.6]undecane-8-carboxylate (549 mg, 2.05 mmol) in Toluene (20 mL) was added 2-methyl-3-oxocyclopent-1-en-1-yl trifluoromethanesulfonate (500 mg, 2.05 mmol), XANTPHOS (18.1 mg, 0.031 mmol), Pd2(dba)3 (9.53 mg, 10.4 μmol), and cesium carbonate (270 mg, 0.83 mmol). The reaction mixture was heated at 60° C. overnight. The reaction was filtered through a CELITE and washed with EtOAc, and purified by MPLC using 120 g Redi-sep column and 5% MeOH/DCM to furnish tert-butyl 2-(2-methyl-3-oxocyclopent-1-en-1-yl)-1-oxo-2,8-diazaspiro[4.6]undecane-8-carboxylate. The material was separated under SFC conditions: Chiralpak Iowa, 30 mm×250 mm, 10μ, 25% 2:1 MeOH:MeCN/CO2, 70 ml/min, 100 bar, 35° C., 220 nm, 180 mg/ml in MeCN Peak A @ 3.39 min, and Peak B @ 3.87 min. The two isomers were further treated separately with TFA to deliver 2-(2-Methyl-3-oxocyclopent-1-enyl)-2,8-diazaspiro[4.6]undecan-1-one (Isomer A and B). LC-MS (IE, m/z): 263 [M+1]⁻. Alternatively, the mixture of enantiomers (prior to chiral HPLC separation) could be treated with TFA to afford the title compound as a mixture of two enantiomers.

Intermediate 27

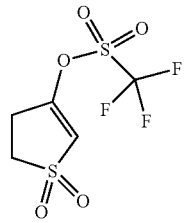 [SMILES: O=S1(=O)C=C(OS(=O)(=O)C(F)(F)F)CC1]

1,1-dioxido-4,5-dihydrothiophen-3-yl trifluoromethanesulfonate

To a solution of dihydro-3(2H)-thiophenone 1,1-dioxide (300 mg, 2.24 mmol) in DCM (15 mL) at −78° C. was added 2,6 lutidine (0.391 mL, 3.35 mmol) followed by triflic anhydride (0.45 mL, 2.7 mmol) dropwise. The reaction temperature was maintained at −78° C. for 0.5 h before warming to rt for 1 h. The mixture was washed with 1 N HCl (10 mL), then with dilute aqueous solution of NaHCO₃ (5 mL). The organic layer was dried over Na₂SO₄ and concentrated to give the title compound. LC-MS (IE, m/z): 267 [M+1]⁺

Intermediate 28

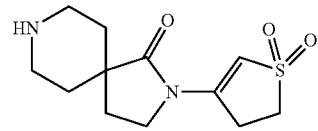 [SMILES: O=C1N(C2=CS(=O)(=O)CC2)CCC12CCNCC2]

2-(1,1-dioxido-4,5-dihydrothiophen-3-yl)-2,8-diazaspiro[4.5]decan-1-one

Step A: tert-Butyl 2-(1,1-dioxido-4,5-dihydrothiophen-3-yl)-1-oxo-2,8-diazaspiro[4.5]decane-8-carboxylate To tert-butyl 1-oxo-2,8-diazaspiro[4.5]decane-8-carboxylate (955 mg, 3.76 mmol) in toluene (50 ml) with water (0.203 ml, 11.27 mmol) was added 1,1-dioxido-4,5-dihydrothiophen-3-yl trifluoromethanesulfonate (1000 mg, 3.76 mmol), XANTPHOS (217, 0.376 mmol), palladium acetate (42.2 mg, 0.188 mmol), and K₂CO₃ (1038 mg, 7.51 mmol). The mixture was heated to 60° C. for 16 hrs. The reaction was filtered through CELITE and washed with ETOAc then concentrated. The residue was purified by MPLC using ISCO 40 g Redi-sep column with solvent system of 5% MeOH/DCM to yield the title compound. LC-MS (IE, m/z): 393 [M+23]⁺

Step B: 2-(1,1-dioxido-4,5-dihydrothiophen-3-yl)-2,8-diazaspiro[4.5]decan-1-one tert-Butyl2-(1,1-dioxido-4,5-dihydrothiophen-3-yl)-1-oxo-2,8-diazaspiro[4.5]decane-8-carboxylate (370 mg, 1.0 mmol) was stirred at rt in TFA (4 mL, 52 mmol) for 1 hr. Excess TFA was evaporated off. The residue was taken up with 4 mL MeOH/1 mL H₂O and loaded on Agilent Elut Bond SCX cartridge then washed with MeOH (1.5 column volumes), then eluted with 2 M methanolic NH₃ (3 CV) to yield the title compound. LC-MS (IE, m/z): 271 [M+1]⁺; ¹H-NMR (500 MHz, CD₃OD) δ ppm 6.605 (s, 1H), 3.707 (t, J=7.0 Hz, 2H), 3.410-3.437 (m, 2H), 3.374-3.348 (m, 2H), 3.138 (t, J=4.5 Hz, 2H), 3.112 (t, J=4.5 Hz, 2H), 2.822-2.849 (m, 2H), 2.154 (t, J=7.0 Hz, 2H), 1.84-1.900 (m, 2H), 1.58 (d, J=13.5 Hz, 2H).

Intermediate 29

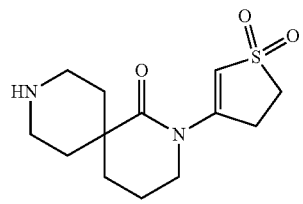 [SMILES: O=C1N(C2=CS(=O)(=O)CC2)CCCC12CCNCC2]

2-(1,1-dioxido-4,5-dihydrothiophen-3-yl)-2,9-diazaspiro[5.5]undecan-1-one

The intermediate was prepared via the same procedure as Intermediate 28 (immediately above) from 1,1-dioxido-4,5-dihydrothiophen-3-yl trifluoromethanesulfonate and tert-butyl 1-oxo-2,9-diazaspiro[5.5]undecane-9-carboxylate. LC-MS (IE, m/z): 285 [M+1]⁺

Intermediate 30

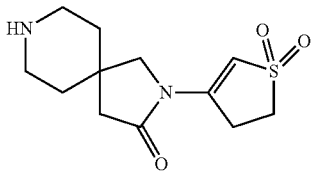 [SMILES: O=C1CC2(CCNCC2)CN1C1=CS(=O)(=O)CC1]

2-(1,1-dioxido-4,5-dihydrothiophen-3-yl)-2,8-diazaspiro[4.5]decan-3-one

The intermediate was prepared via the same procedure as Intermediate 28 from 1,1-dioxido-4,5-dihydrothiophen-3-yl trifluoromethanesulfonate and tert-butyl 3-oxo-2,8-diazaspiro[4.5]decane-8-carboxylate. LC-MS (IE, m/z): 271 [M+1]⁺

Intermediate 31

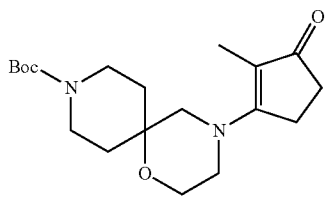 [SMILES: CC1=C(N2CCOC3(CCN(C(=O)OC(C)(C)C)CC3)C2)CCC1=O]

tert-Butyl 4-(2-methyl-3-oxocyclopent-1-en-1-yl)-1-oxa-4,9-diazaspiro[5.5]undecane-9-carboxylate In a 100 mL round bottom flask, tert-butyl 1-oxa-4,9-diazaspiro[5.5]undecane-9-carboxylate (500 mg, 1.95 mmol) was mixed with 2-methylcyclopentane-1,3-dione (284 mg, 2.54 mmol), ammonium acetate (30.1 mg, 0.390 mmol) and acetic acid (0.447 mL, 7.80 mmol) in toluene (20 mL) and heated at 130° C. for 12 hours. A Dean-Stark trap was applied to remove generated water during the reaction. After the reaction was cooled to room temperature, the solvent was removed and residue was dissolved in ethyl acetate (40 mL) and washed with 1N NaOH (aqueous) (20 mL), brine (20 mL) and dried over anhydrous sodium sulfate. Concentration on rotavapor gave crude product that was used without further purification. LC-MS (IE, m/z): 351.3 [M+1]⁺.

Intermediate 32

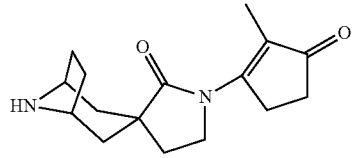 [SMILES: CC1=C(N2CCC3(CC4CCC(C3)N4)C2=O)CCC1=O]

1'-(2-Methyl-3-oxocyclopent-1-enyl)-8-azaspiro[bicyclo[3.2.1]octane-3,3'-pyrrolidin]-2'-one Step A: (1R,3r,5S)-8-tert-butyl 3-ethyl 3-(cyanomethyl)-8-azabicyclo[3.2.1]octane-3,8-dicarboxylate To a solution of (1R,3s,5S)-8-tert-butyl 3-ethyl 8-azabicyclo[3.2.1]octane-3,8-dicarboxylate (2 g, 7 mmol) in THF (50 mL) was added LDA (5.29 mL, 10.6 mmol) at -78° C. After the mixture was stirred at the same temperature for 30 min, bromoacetonitrile (0.737 mL, 10.6 mmol) in THF (15 mL) was added by injection. The mixture was stirred at -78° C. for 15 min, quenched with saturated KHSO₄ at -78° C., warmed up to rt and diluted with ether (100 mL). The organic layer was separated, and the aqueous was extracted with ether (50 mL). The combined organic layers were washed with brine, dried (MgSO₄), and concentrated. The crude material was purified by column chromatography (silica gel, 0-60% ethyl acetate in hexane). LC-MS (IE, m/z): 223 [M+1-100]⁺.

Step B: 8-tert-butyl 3-ethyl 3-(2-aminoethyl)-8-azabicyclo[3.2.1]octane-3,8-dicarboxylate To a solution of (1R,3r,5S)-8-tert-Butyl 3-ethyl 3-(cyanomethyl)-8-azabicyclo[3.2.1]octane-3,8-dicarboxylate (0.5 g, 1.6 mmol) in a mixture solvent of ethanol (20 mL) and AcOH (20 mL) was added platinum(iv) oxide (0.035 g, 0.16 mmol). The mixture was hydrogenated (45 psi hydrogen) for 24 hr. The catalyst was filtered off through a CELITE pad. The filtration was concentrated. The crude material was used for the next step without further purification. LC-MS (IE, m/z): 327 [M+1]⁺.

Step C: tert-butyl 2'-oxo-8-azaspiro[bicyclo[3.2.1]octane-3,3'-pyrrolidine]-8-carboxylate A mixture of 1R,3r,5S)-8-tert-butyl 3-ethyl 3-(2-8-azabicyclo[3.2.1]octane-3,8-dicarboxylate (0.5 g, 1.5 mmol) and potassium carbonate powder (1.06 g, 7.66 mmol) in MeOH (50 mL) was heated at 60° C. for 3 hr. The mixture was concentrated, and DCM (50 mL) was added. The suspension was filtered through a CELITE pad. The filtrate was concentrated to give a solid which was directly used in the next step. LC-MS (IE, m/z): 281 [M+1]+.

Step D: 1'-(2-Methyl-3-oxocyclopent-1-enyl)-8-azaspiro[bicyclo[3.2.1]octane-3,3'-pyrrolidin]-2'-one A mixture of 2-methyl-3-oxocyclopent-1-en-1-yl trifluoromethanesulfonate (0.479 g, 1.96 mmol), (1R,3r,5S)-tert-butyl 2'-[3.2.1]octane-3,3'-pyrrolidine]-8-carboxylate (0.5 g, 1.8 mmol), palladium(ii) acetate (0.020 g, 0.089 mmol), 4,5-bis(diphenylphosphino)-9,9-dimethylxanthene (0.103 g, 0.178 mmol), potassium carbonate (0.739 g, 5.35 mmol) and water (0.096 mL, 5.35 mmol) in toluene (100 mL) was heated at 60° C. under $N_2$ for 4 hr. The mixture was diluted with ethyl acetate (50 mL). Solid was filtered off through a CELITE pad, and the filtrate was concentrated. The residue was purified by column (silica gel, 0-100% of EtOAc in hexane). LC-MS (IE, m/z): 375 [M+1]+. The purified material (0.6 g, 2.4 mmol) was dissolved in DCM (20 mL). The solution was stirred with TFA (2.75 ml, 35.7 mmol) at rt for 1 h. Volatiles were removed. The residue was dissolved in methanol, and was loaded on Bond Elut SCX column. The column with the desired compound was eluted with methanol (~20 mL) to remove TFA. The free base of the desired compound was eluted out with 2 N $NH_3$ in methanol (~20 mL). The solution was concentrated to give a free base (solid). LC-MS (IE, m/z): 275 [M+1]+.

Intermediate 33

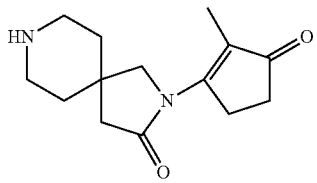 [SMILES: CC1=C(N2CC3(CCNCC3)CC2=O)CCC1=O]

2-(2-methyl-3-oxocyclopent-1-en-1-yl)-2,8-diazaspiro[4.5]decan-3-one

The title compound was prepared in two steps in an analogous fashion as described for the synthesis of Intermediates 26 and 27 starting from 2-methyl-3-oxocyclopent-1-en-1-yl trifluoromethanesulfonate and 3-oxo-2,8-diazaspiro[4,5]decane-8-carboxylic acid tert-butyl ester. LC-MS (IE, m/z): 249 [M+1]+.

Example 1

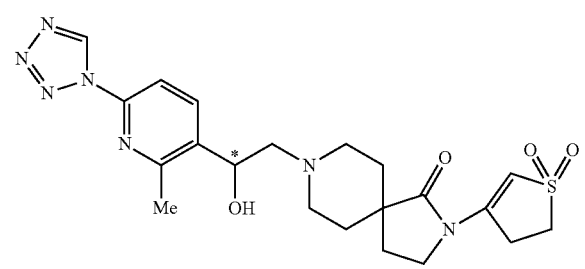 [SMILES: Cc1nc(-n2cnnn2)ccc1C(O)CN1CCC2(CC1)CCN(C1=CS(=O)(=O)CC1)C2=O]

2-(1,1-dioxido-4,5-dihydrothiophen-3-yl)-8-(2-hydroxy-2-(2-methyl-6-(1H-tetrazol-1-yl)pyridin-3-yl) ethyl)-2,8-diazaspiro[4.5]decan-1-one In a microwave tube 2-(1,1-dioxido-4,5-dihydrothiophen-3-yl)-2,8-diazaspiro[4.5]decan-1-one was dissolved in ethanol (6 mL) then 2-methyl-3-(oxiran-2-yl)-6-(1H-tetrazol-1-yl)pyridine (slower eluting, 1-5B) (60.7 mg, 0.299 mmol) was added. The tube was sealed and heated at 100° C. overnight. The reaction was concentrated and purified by preparative TLC using 1000 μm plates with a solvent system of MeOH:ETOAc (30:70) to yield the title compound as a single enantiomer. LC-MS (IE, m/z): 474 [M+1]+; 1H-NMR 600 MHz, $CD_3OD$) δ ppm 9.876 (s, 1H), 8.176 (d, J=8.4 Hz, 1H), 7.914 (d, J=8.4 Hz, 1H), 6.569 (s, 1H), 5.143 (dd, J=8.7, 4.2 Hz, 1H), 3.673 (t, J=7.2 Hz, 2H), 3.387-3.416 (m, 2H), 3.326-3.354 (m, 2H), 2.944-3.016 (m, 2H), 3.634 (s, 3H), 2.557-2.616 (m, 2H), 2.405 (t, J=9.0 Hz, 1H), 2.33 (t, J=9.6 Hz, 1H), 2.100 (t, J=7.2 Hz, 2H), 1.897-1.975 (m, 2H), 1.5867 (d, J=13.2 Hz, 2H).

Example 2

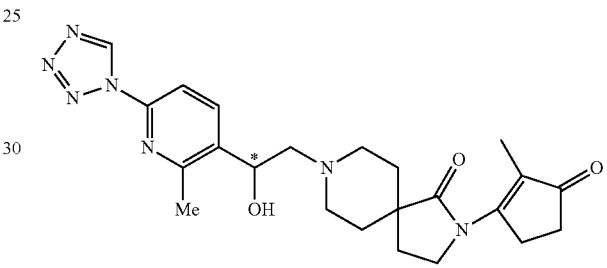

8-(2-hydroxy-2-(2-methyl-6-(1H-tetrazol-1-yl)pyridin-3-yl)ethyl)-2-(2-methyl-3-oxocyclopent-1-en-1-yl)-2,8-diazaspiro[4.5]decan-1-one 2-(2-methyl-3-oxocyclopent-1-en-1-yl)-2,8-diazaspiro[4.5]decan-1-one (0.056 g, 0.226 mmol) and 2-methyl-3-(oxiran-2-yl)-6-(1H-tetrazol-1-yl)pyridine (slower eluting, Intermediate 5B) (0.060 g, 0.295 mmol) were added to EtOH (5 mL) in a microwave tube. The tube was sealed and heated to 100° C. for 16 hrs. The reaction was concentrated and purified by preparative TLC using 1000 μm plates with solvent system of MeOH:ETOAc (30:70) to afford the title compound as a single enantiomer. LC-MS (IE, m/z): 451 [M+1]+.

Example 3A and 3B

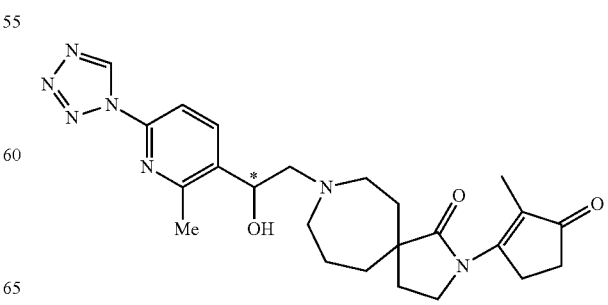

8-(2-hydroxy-2-(2-methyl-6-(1H-tetrazol-1-yl)pyridin-3-yl)ethyl)-2-(2-methyl-3-oxocyclopent-1-en-1-yl)-2,8-diazaspiro[4.6]undecan-1-one In a microwave tube 2-(2-methyl-3-oxocyclopent-1-en-1-yl)-2,8-diazaspiro[4.6]undecan-1-one (82 mg, 0.313 mmol) was stirred in EtOH (5 mL) then 2-methyl-3-(oxiran-2-yl)-6-(1H-tetrazol-1-yl)pyridine (faster eluting, I-5A) (76 mg, 0.375 mmol) was added. The tube was sealed and heated to 100° C. for 16 hrs. The reaction mixture was concentrated and purified by preparative TLC using 1×2000 µm with MeOH:ETOAc. (30:70) solvent system then again with another 1000 µm silica plate with MeOH:DCM (10:90) to yield the title compound as a mixture of two diastereomers. LC-MS (IE, m/z): 466[M+1]$^+$ $^1$H-NMR (500 MHz, CDCl$_3$) δ ppm 9.536 (s, 1H), 8.1509 (d, J=8.5 Hz, 1H), 7.938 (d, J=8.5 Hz, 1H), 4.945 (dd, J=10.25, 2.5 Hz, 1H), 3.866-3.899 (m, 2H), 2.74-3.098 (m, 7H), 2.59 (d, J=4 Hz, 3H), 2.446-2.472 (m, 2H), 2.389 (t, J=11 Hz, 1H), 1.960-2.229 (m, 6H), 1.851 (d, J=2 Hz, 3H), 1.768-1.812 (m, 2H).

The diastereomers were separated in a Chiralpak AS 21×250 mm column with the following conditions: 35% MeOH+0.2% DEA/CO$_2$, 50 ml/min, 100 bar, 35° C., 10 mg/ml in MeOH, 220 nM).

Isomer 4A–T$_R$=7.23 min. LC-MS (IE, m/z): 466[M+1]$^{30}$
Isomer 4B–T$_R$=8.76 min. LC-MS (IE, m/z): 466[M+1]$^+$ Example 4

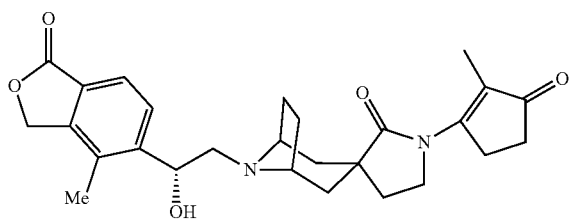 [SMILES: CC1=C(N2CCC3(CC4CCC(C3)N4C[C@H](O)c3ccc4c(c3C)COC4=O)C2=O)CCC1=O]

(1R,3R,5S)-8-((R)-2-hydroxy-2-(4-methyl-1-oxo-1,3-dihydroisobenzofuran-5-yl)ethyl)-1'-(2-methyl-3-oxocyclopent-1-en-1-yl)-8-azaspiro[bicyclo[3.2.1]octane-3,3'-pyrrolidin]-2'-one (1R,3r,5S)-1'-(2-methyl-3-oxocyclopent-1-en-1-yl)-8-azaspiro[bicyclo[3.2.1]octane-3,3'-pyrrolidin]-2'-one (0.031 g, 0.113 mmol) and (R)-4-methyl-5-(oxiran-2-yl) isobenzofuran-1(3H)-one (0.023 g, 0.113 mmol) in EtOH (5 mL) was microwaved at 145° C. for 4.5 hr. The solvent was removed, and the crude product was purified by preparative TLC (30% methanol in EtOAc) to afford the title compound. LC-MS: 478.27(+1), 450.2 (+1-28).

Example 5

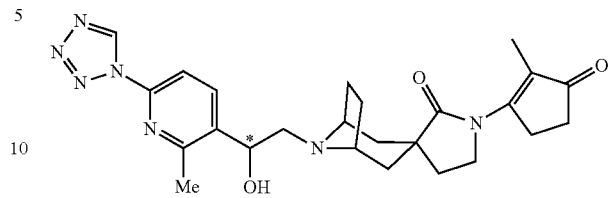

8(1R,3r,5S)-8-(2-hydroxy-2-(2-methyl-6-(1H-tetrazol-1-yl)6 0icycle6 0-3-yl)ethyl)-1'-(2-methyl-3-oxocyclopent-1-en-1-yl)-8-azaspiro[bicyclo[3.2.1]octane-3,3'-pyrrolidin]-2'-one (1R,3r,5S)-1'-(4-methyl-5-oxo-2,5-dihydrofuran-3-yl)-8-azaspiro[bicyclo[3.2.1]octane-3,3'-pyrrolidin]-2'-one (0.051 g, 0.185 mmol) and 2-methyl-3-(oxiran-2-yl)-6-(1H-tetrazol-1-yl)pyridine (faster eluting, I-5A) (0.039 g, 0.203 mmol) in EtOH (3 mL) was heated at 90° C. for 2 hr. The solvent was removed, and the crude material was purified by preparative TLC (30% methanol in EtOAc). LC-MS: 485.24 (+23) and 439.17 (+1-28).

Example 6

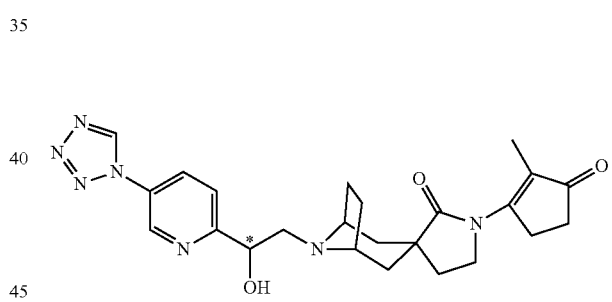

(1R,3r,5S)-8-(2-(5-(1H-tetrazol-1-yl)pyridin-2-yl)-2-hydroxyethyl)-1'-(2-methyl-3-oxocyclopent-1-en-1-yl)-8-azaspiro[bicyclo[3.2.1]octane-3,3'-pyrrolidin]-2'-one (1R,3r,5S)-1'-(4-methyl-5-oxo-2,5-dihydrofuran-3-yl)-8-azaspiro[bicyclo[3.2.1]octane-3,3'-pyrrolidin]-2'-one (0.051 g, 0.185 mmol) and 2-(oxiran-2-yl)-5-(1H-tetrazol-1-yl) pyridine (I-4A faster eluting) (0.038 g, 0.203 mmol) in EtOH (3 mL) was heated at 90° C. for 2 hr. The solvent was removed, and the crude material was purified by preparative TLC (30% methanol in EtOAc). LCMS: 464.20(+1) and 436.16 (+1-28).

The following Examples were prepared by following the standard epoxide opening procedure as described in Examples 1-6. The starting epoxides and amines are indicated.

TABLE 2

Compounds prepared following a similar procedure as for EXAMPLES 1-6

| EXAMPLE | Epoxide Intermediate | Amine Intermediate | Structure, name and characterization |
|---|---|---|---|
| 7 | 2A | 31 | 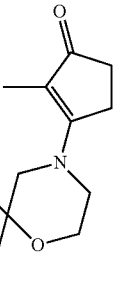<br>(R)-5-(1-hydroxy-2-(4-(2-methyl-3-oxocyclopent-1-en-1-yl)-1-oxa-4,9-diazaspiro[5.5]undecan-9-yl)ethyl)-4-methylisobenzofuran-1(3H)-one<br>LC-MS (IE, m/z): 441.3 (M + 1)⁺. |
| 8 | 3A | 31 | 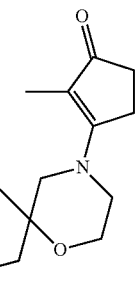<br>(R)-3-(9-(2-(6-(1H-tetrazol-1-yl)pyridin-3-yl)-2-hydroxyethyl)-1-oxa-4,9-diazaspiro[5.5]undecan-4-yl)-2-methylcyclopent-2-enone<br>LC-MS (IE, m/z): 440.4 (M + 1)⁺. |
| 9 | 5A | 31 | 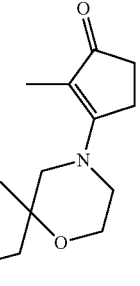<br>3-(9-(2-hydroxy-2-(2-methyl-6-(1H-tetrazol-1-yl)pyridin-3-yl)ethyl)-1-oxa-4,9-diazaspiro[5.5]undecan-4-yl)-2-methylcyclopent-2-enone<br>LC-MS (IE, m/z): 454.3 (M + 1)⁺. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 10 | 9A | 31 | 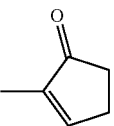<br>3-(9-(2-hydroxy-2-(2-methyl-4-(1H-tetrazol-1-yl)phenyl)ethyl)-1-oxa-4,9-diazaspiro[5.5]undecan-4-yl)-2-methylcyclopent-2-enone<br>LC-MS (IE, m/z): 453.4 (M + 1)⁺. |
| 11 | 2A | 19 | 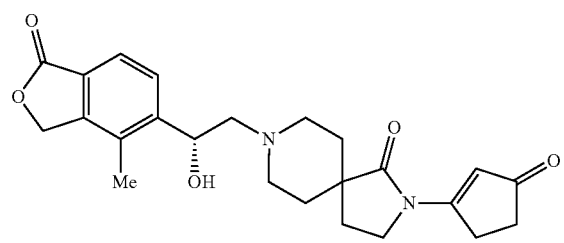<br>(R)-8-(2-hydroxy-2-(4-methyl-1-oxo-1,3-dihydroisobenzofuran-5-yl)ethyl)-2-(3-oxocyclopent-1-en-1-yl)-2,8-diazaspiro[4.5]decan-1-one<br>LC-MS (IE, m/z): 425 (M + 1)⁺. |
| 12 | 2A | 18 | 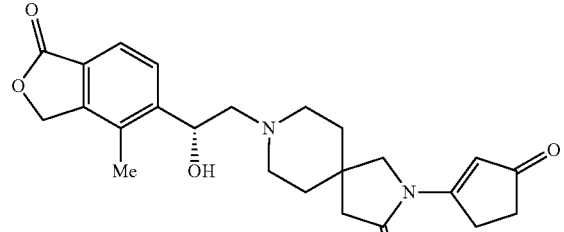<br>(R)-8-(2-hydroxy-2-(4-methyl-1-oxo-1,3-dihydroisobenzofuran-5-yl)ethyl)-2-(3-oxocyclopent-1-en-1-yl)-2,8-diazaspiro[4.5]decan-3-one<br>LC-MS (IE, m/z): 425 (M + 1)⁺. |
| 13 | 5A | 18 | 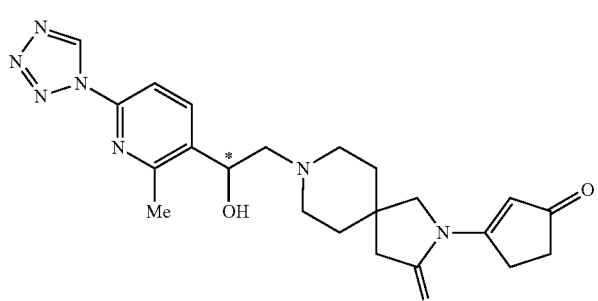<br>8-(2-hydroxy-2-(2-methyl-6-(1H-tetrazol-1-yl)pyridin-3-yl)ethyl)-2-(3-oxocyclopent-1-en-1-yl)-2,8-diazaspiro[4.5]decan-3-one<br>LC-MS (IE, m/z): 438 (M + 1)⁺. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 14 | 5A | 19 | 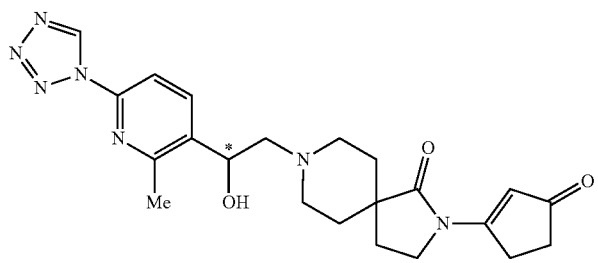<br>8-(2-hydroxy-2-(2-methyl-6-(1H-tetrazol-1-yl)pyridin-3-yl)ethyl)-2-(3-oxocyclopent-1-en-1-yl)-2,8-diazaspiro[4.5]decan-1-one<br>LC-MS (IE, m/z): 438 (M + 1)⁺. |
| 15 | 5A | 28 | 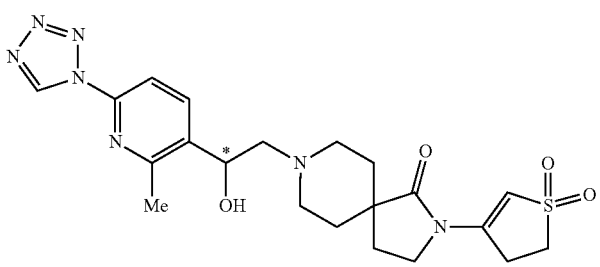<br>2-(1,1-dioxido-4,5-dihydrothiophen-3-yl)-8-(2-hydroxy-2-(2-methyl-6-(1H-tetrazol-1-yl)pyridin-3-yl)ethyl)-2,8-diazaspiro[4.5]decan-1-one<br>LC-MS (IE, m/z): 474 (M + 1)⁺. |
| 16 | 2A | 28 | 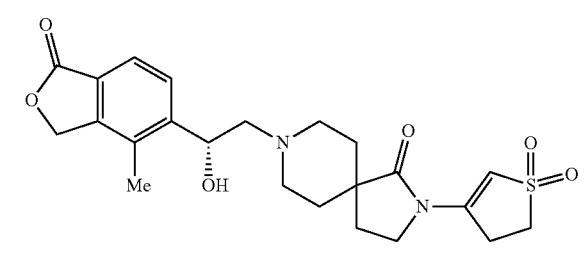<br>(R)-2-(1,1-dioxido-4,5-dihydrothiophen-3-yl)-8-(2-hydroxy-2-(4-methyl-1-oxo-1,3-dihydroisobenzofuran-5-yl)ethyl)-2,8-diazaspiro[4.5]decan-1-one<br>LC-MS (IE, m/z): 461 (M + 1)⁺. |
| 17 | 5A | 30 | 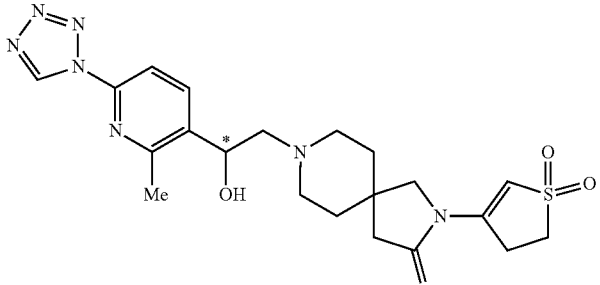<br>2-(1,1-dioxido-4,5-dihydrothiophen-3-yl)-8-(2-hydroxy-2-(2-methyl-6-(1H-tetrazol-1-yl)pyridin-3-yl)ethyl)-2,8-diazaspiro[4.5]decan-3-one<br>LC-MS (IE, m/z): 474 (M + 1)⁺. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 18 | 5A | 23 | 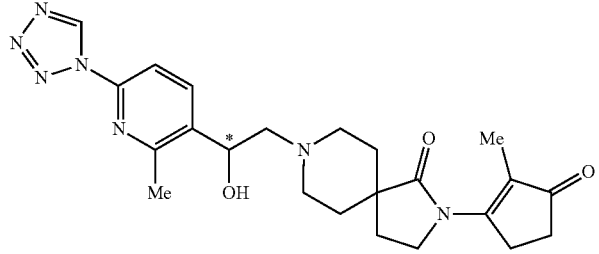 8-(2-hydroxy-2-(2-methyl-6-(1H-tetrazol-1-yl)pyridin-3-yl)ethyl)-2-(2-methyl-3-oxocyclopent-1-en-1-yl)-2,8-diazaspiro[4.5]decan-1-one LC-MS (IE, m/z): 452 (M + 1)$^+$. |
| 19 | 2A | 23 | 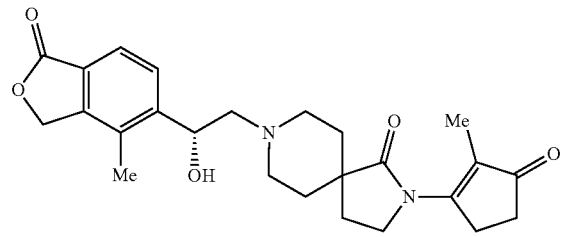 (R)-8-(2-hydroxy-2-(4-methyl-1-oxo-1,3-dihydroisobenzofuran-5-yl)ethyl)-2-(2-methyl-3-oxocyclopent-1-en-1-yl)-2,8-diazaspiro[4.5]decan-1-one LC-MS (IE, m/z): 439 (M + 1)$^+$. |
| 20 | 2A | 33 | 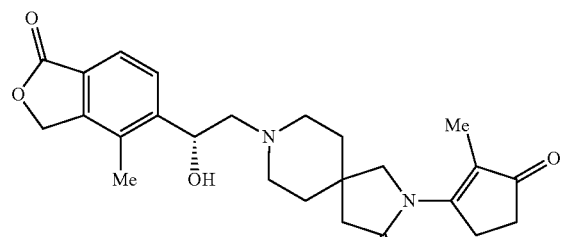 (R)-8-(2-hydroxy-2-(4-methyl-1-oxo-1,3-dihydroisobenzofuran-5-yl)ethyl)-2-(2-methyl-3-oxocyclopent-1-en-1-yl)-2,8-diazaspiro[4.5]decan-3-one LC-MS (IE, m/z): 439 (M + 1)$^+$. |
| 21 | 3A | 23 | 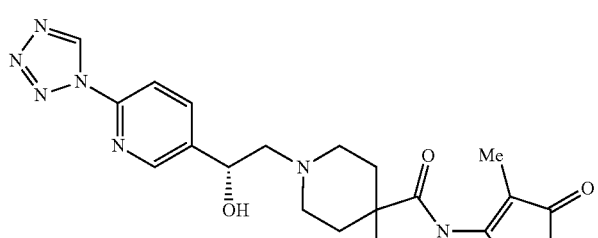 (R)-8-(2-(6-(1H-tetrazol-1-yl)pyridin-3-yl)-2-hydroxyethyl)-2-(2-methyl-3-oxocyclopent-1-en-1-yl)-2,8-diazaspiro[4.5]decan-1-one LC-MS (IE, m/z): 438 (M + 1)$^+$. |

TABLE 2-continued

| | Compounds prepared following a similar procedure as for EXAMPLES 1-6 | | |
|---|---|---|---|
| EXAMPLE | Epoxide Intermediate | Amine Intermediate | Structure, name and characterization |
| 22 | 3A | 28 | 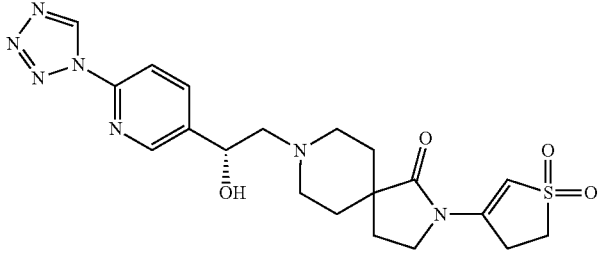<br>(R)-8-(2-(6-(1H-tetrazol-1-yl)pyridin-3-yl)-2-hydroxyethyl)-2-(1,1-dioxido-4,5-dihydrothiophen-3-yl)-2,8-diazaspiro[4.5]decan-1-one<br>LC-MS (IE, m/z): 460 (M + 1)⁺. |
| 23 | 3A | 19 | 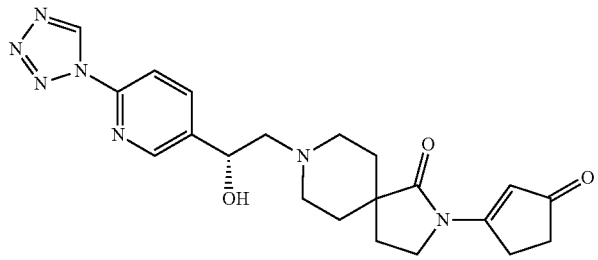<br>(R)-8-(2-(6-(1H-tetrazol-1-yl)pyridin-3-yl)-2-hydroxyethyl)-2-(3-oxocyclopent-1-en-1-yl)-2,8-diazaspiro[4.5]decan-1-one<br>LC-MS (IE, m/z): 424 (M + 1)⁺. |
| 24 | 8A | 23 | 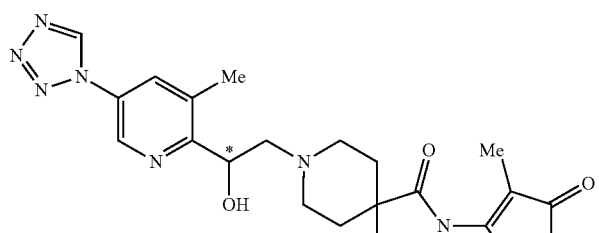<br>8-(2-hydroxy-2-(3-methyl-5-(1H-tetrazol-1-yl)pyridin-2-yl)ethyl)-2-(2-methyl-3-oxocyclopent-1-en-1-yl)-2,8-diazaspiro[4.5]decan-1-one<br>LC-MS (IE, m/z): 452 (M + 1)⁺. |
| 25 | 8B | 23 | 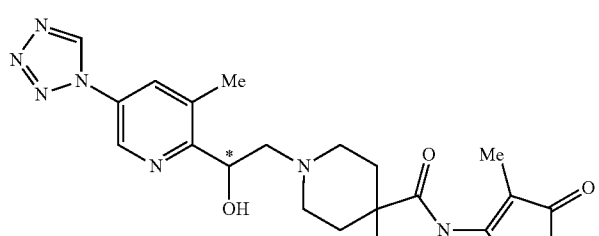<br>8-(2-hydroxy-2-(3-methyl-5-(1H-tetrazol-1-yl)pyridin-2-yl)ethyl)-2-(2-methyl-3-oxocyclopent-1-en-1-yl)-2,8-diazaspiro[4.5]decan-1-one<br>LC-MS (IE, m/z): 452 (M + 1)⁺. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 26 | 9A | 23 | 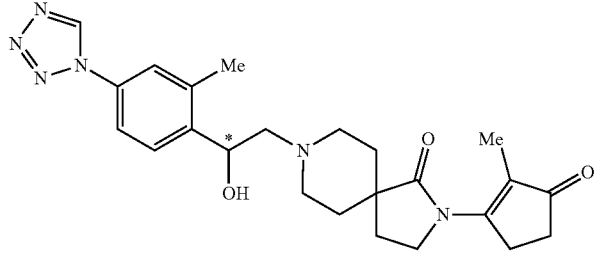 8-(2-hydroxy-2-(2-methyl-4-(1H-tetrazol-1-yl)phenyl)ethyl)-2-(2-methyl-3-oxocyclopent-1-en-1-yl)-2,8-diazaspiro[4.5]decan-1-one LC-MS (IE, m/z): 451 (M + 1)$^+$. |
| 27 | 9B | 23 | 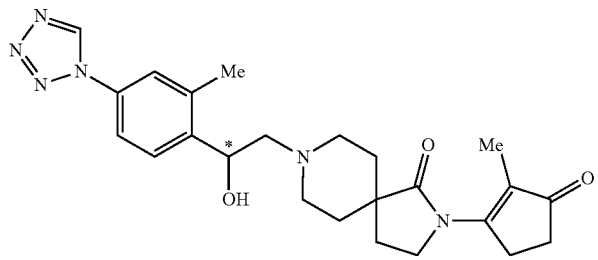 8-(2-hydroxy-2-(2-methyl-4-(1H-tetrazol-1-yl)phenyl)ethyl)-2-(2-methyl-3-oxocyclopent-1-en-1-yl)-2,8-diazaspiro[4.5]decan-1-one LC-MS (IE, m/z): 451 (M + 1)$^+$. |
| 28 | 7A | 23 | 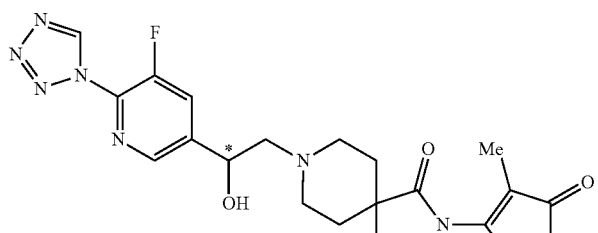 8-(2-(5-fluoro-6-(1H-tetrazol-1-yl)pyridin-3-yl)-2-hydroxyethyl)-2-(2-methyl-3-oxocyclopent-1-en-1-yl)-2,8-diazaspiro[4.5]decan-1-one LC-MS (IE, m/z): 456 (M + 1)$^+$. |
| 29 | 7B | 23 | 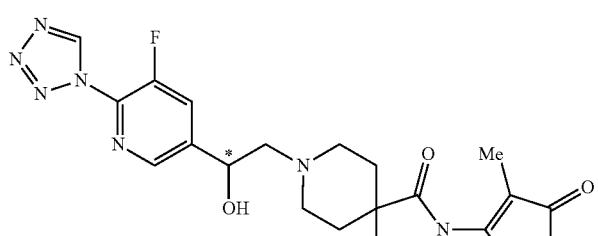 8-(2-(5-fluoro-6-(1H-tetrazol-1-yl)pyridin-3-yl)-2-hydroxyethyl)-2-(2-methyl-3-oxocyclopent-1-en-1-yl)-2,8-diazaspiro[4.5]decan-1-one LC-MS (IE, m/z): 456 (M + 1)$^+$. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 30 | 7A | 19 | 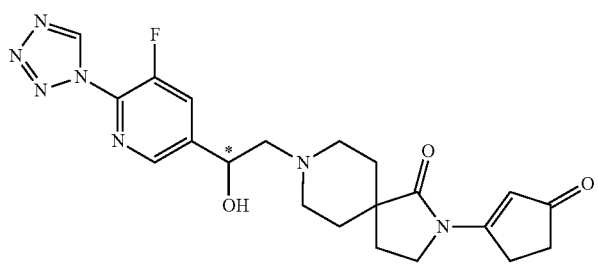<br>8-(2-(5-fluoro-6-(1H-tetrazol-1-yl)pyridin-3-yl)-2-hydroxyethyl)-2-(3-oxocyclopent-1-en-1-yl)-2,8-diazaspiro[4.5]decan-1-one<br>LC-MS (IE, m/z): 442 (M + 1)$^+$. |
| 31 | 7B | 19 | 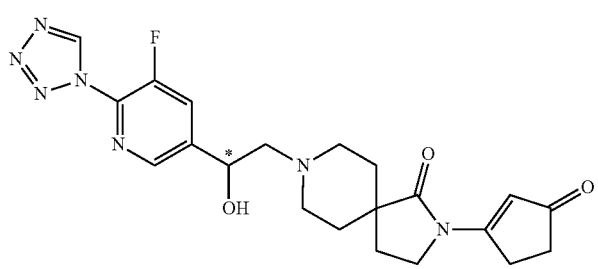<br>8-(2-(5-fluoro-6-(1H-tetrazol-1-yl)pyridin-3-yl)-2-hydroxyethyl)-2-(3-oxocyclopent-1-en-1-yl)-2,8-diazaspiro[4.5]decan-1-one<br>LC-MS (IE, m/z): 442 (M + 1)$^+$. |
| 32 | 5A | 24 | 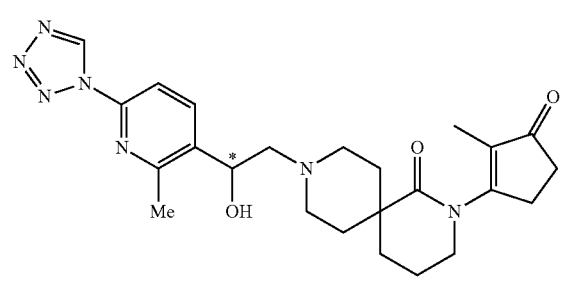<br>9-(2-hydroxy-2-(2-methyl-6-(1H-tetrazol-1-yl)pyridin-3-yl)ethyl)-2-(2-methyl-3-oxocyclopent-1-en-1-yl)-2,9-diazaspiro[5.5]undecan-1-one<br>LC-MS (IE, m/z): 466 (M + 1)$^+$. |
| 33 | 5A | 20 | 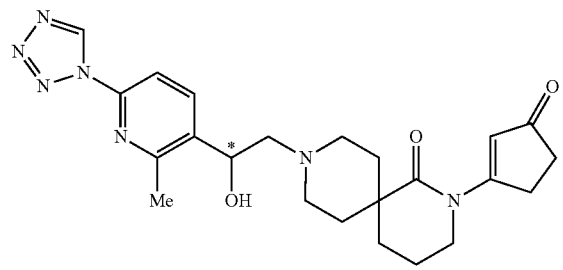<br>9-(2-hydroxy-2-(2-methyl-6-(1H-tetrazol-1-yl)pyridin-3-yl)ethyl)-2-(3-oxocyclopent-1-en-1-yl)-2,9-diazaspiro[5.5]undecan-1-one<br>LC-MS (IE, m/z): 452 (M + 1)$^+$. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 34 | 2A | 20 | (R)-9-(2-hydroxy-2-(4-methyl-1-oxo-1,3-dihydroisobenzofuran-5-yl)ethyl)-2-(3-oxocyclopent-1-en-1-yl)-2,9-diazaspiro[5.5]undecan-1-one<br>LC-MS (IE, m/z): 439 (M + 1)$^+$. |
| 35 | 9A | 19 | 8-(2-hydroxy-2-(2-methyl-4-(1H-tetrazol-1-yl)phenyl)ethyl)-2-(3-oxocyclopent-1-en-1-yl)-2,8-diazaspiro[4.5]decan-1-one<br>LC-MS (IE, m/z): 437 (M + 1)$^+$. |
| 36 | 10A | 23 | 8-(2-(2-fluoro-4-(1H-tetrazol-1-yl)phenyl)-2-hydroxyethyl)-2-(2-methyl-3-oxocyclopent-1-en-1-yl)-2,8-diazaspiro[4.5]decan-1-one<br>LC-MS (IE, m/z): 455 (M + 1)$^+$. |
| 37 | 10A | 19 | 8-(2-(2-fluoro-4-(1H-tetrazol-1-yl)phenyl)-2-hydroxyethyl)-2-(3-oxocyclopent-1-en-1-yl)-2,8-diazaspiro[4.5]decan-1-one<br>LC-MS (IE, m/z): 441 (M + 1)$^+$. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 38 | 5A | 29 | 2-(1,1-dioxido-4,5-dihydrothiophen-3-yl)-9-(2-hydroxy-2-(2-methyl-6-(1H-tetrazol-1-yl)pyridin-3-yl)ethyl)-2,9-diazaspiro[5.5]undecan-1-one<br>LC-MS (IE, m/z): 441 (M + 1)+. |
| 39 | 2A | 26A | 8-((R)-2-hydroxy-2-(4-methyl-1-oxo-1,3-dihydroisobenzofuran-5-yl)ethyl)-2-(2-methyl-3-oxocyclopent-1-en-1-yl)-2,8-diazaspiro[4.6]undecan-1-one<br>LC-MS (IE, m/z): 453 (M + 1)+. |
| 40 | 2A | 26B | 8-((R)-2-hydroxy-2-(4-methyl-1-oxo-1,3-dihydroisobenzofuran-5-yl)ethyl)-2-(2-methyl-3-oxocyclopent-1-en-1-yl)-2,8-diazaspiro[4.6]undecan-1-one<br>LC-MS (IE, m/z): 453 (M + 1)+. |
| 41 | 9A | 20 | 9-(2-hydroxy-2-(2-methyl-4-(1H-tetrazol-1-yl)phenyl)ethyl)-2-(3-oxocyclopent-1-en-1-yl)-2,9-diazaspiro[5.5]undecan-1-one<br>LC-MS (IE, m/z): 451 (M + 1)+. |

TABLE 2-continued

Compounds prepared following a similar procedure as for EXAMPLES 1-6

| EXAMPLE | Epoxide Intermediate | Amine Intermediate | Structure, name and characterization |
|---|---|---|---|
| 42 | 4A | 20 | 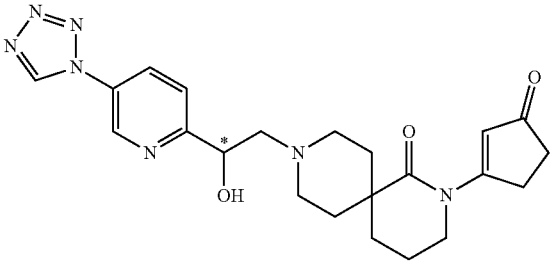<br>9-(2-(5-(1H-tetrazol-1-yl)pyridin-2-yl)-2-hydroxyethyl)-2-(3-oxocyclopent-1-en-1-yl)-2,9-diazaspiro[5.5]undecan-1-one<br>LC-MS (IE, m/z): 438 (M + 1)⁺. |
| 43 | 6A | 26B | 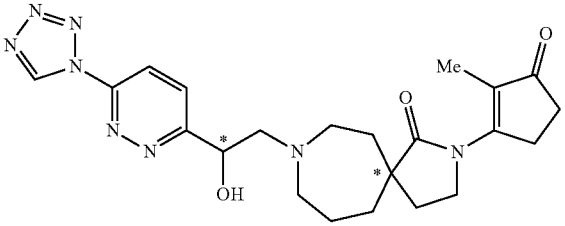<br>8-(2-(6-(1H-tetrazol-1-yl)pyridazin-3-yl)-2-hydroxyethyl)-2-(2-methyl-3-oxocyclopent-1-en-1-yl)-2,8-diazaspiro[4.6]undecan-1-one<br>LC-MS (IE, m/z): 453 (M + 1)⁺. |
| 44 | 6A | 23 | 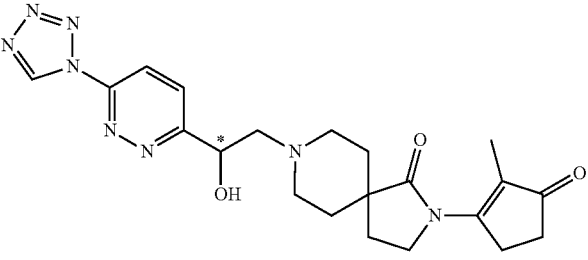<br>8-(2-(6-(1H-tetrazol-1-yl)pyridazin-3-yl)-2-hydroxyethyl)-2-(2-methyl-3-oxocyclopent-1-en-1-yl)-2,8-diazaspiro[4.5]decan-1-one<br>LC-MS (IE, m/z): 439 (M + 1)⁺. |
| 45 | 2A | 25 | 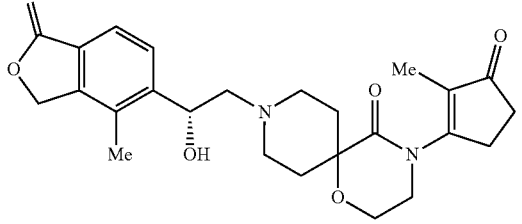<br>(R)-9-(2-hydroxy-2-(4-methyl-1-oxo-1,3-dihydroisobenzofuran-5-yl)ethyl)-4-(2-methyl-3-oxocyclopent-1-en-1-yl)-1-oxa-4,9-diazaspiro[5.5]undecan-5-one;<br>LC-MS (IE, m/z): 455 (M + 1)⁺. |

The following Thallium Flux Assay was performed on each of the final product compounds in the Examples.

Thallium Flux Assay

Cell Culture Conditions—

HEK293 cells stably expressing hROMK (hK$_{ir}$1.1) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, aspirate the media from the flask and rinse with 10 mL Calcium/Magnesium-free PBS. 5 mL of 1× trypsin (prepared in Ca/Mg Free PBS) was added to a T-225 flask and the flask was returned to the 37° C./$CO_2$ incubator for 2-3 minutes. The cell was dislodged by genitly banging the side of the flask by hand. The cells were titrated completely and then the cells were transferred to 25 mL complete media. The cells were centrifuged at 1,500 rpm for 6 min followed by resuspension in complete growth media and cell concentration was determined. 4E6 cells/T-225 flask attained >80% confluency in 4 days. Under ideal growth conditions and appropriate tissue culture practices, this cell line was stable for 40-45 passages.

FluxOR Kit Components (Invitrogen F10017)
- FluxOR™ Reagent (Component A)
- FluxOR™ Assay Buffer (Component B)—10× Concentrate
- PowerLoad™ Concentrate (Component C)—100× Concentrate
- Probenecid (Component D)—Lyophilized sample is kept at −20° C. Water soluble, 100× after solubilization in 1 mL water. Store at 4° C.
- FluxOR™ Chloride-free Buffer (Component E)—5× Concentrate
- Potassium sulfate ($K_2SO_4$) Concentrate (Component F)—125 mM in water. Store at 4° C.
- Thallium sulfate ($Tl_2SO_4$) Concentrate (Component G)—50 mM in water. Store at 4° C.
- DMSO (dimethyl sulfoxide, Component H)—1 mL (100%)

Reagent Preparation: FluxOR Working Solutions
- 1000× FluxOR™ Reagent: Reconstitute a vial of component A in 100 µl DMSO; Mix well; Store 10 µl aliquots at −20° C.
- 1× FluxOR™ Assay Buffer: Dilute Component B 10-fold with water; Adjust pH to 7.4 with Hepes/NaOH; Filter and store at 4° C.
- Probenecid/Assay Buffer: 100 mL of 1× FluxOR™ Assay Buffer; 1 mL of reconstituted component D; Store at 4° C.
- Loading Buffer (per microplate): 10 µl 1000× FluxOR™ Reagent; 100 µl component C; 10 mL Probenecid/Assay Buffer
- Compound Buffer (per microplate): 20 mL Probenecid/Assay Buffer; 0.3 mM ouabain (10 mM ouabain in water can be stored in amber bottle/aluminum foil at room temperature); Test compound
- 1× FluxOR™ Chloride-Free Buffer: Prepare 1× working solution in water. Can be stored at room temperature
- Stimulant Buffer (prepared at 5× final concentration in 1× FluxOR™ Chloride-Free Buffer): 7.5 mM Thallium sulfate and 0.75 mM Potassium sulfate (to give a final assay concentration of 3 mM Thallium/0.3 mM Potassium). Store at 4° C. when not in use. If kept sterile, this solution is good for months.

Assay Protocol—

The ROMK channel functional thallium flux assay was performed in 384 wells, using the FLIPR-Tetra instrument. HEK-hKir1.1 cells were seeded in Poly-D-Lysine microplates and kept in a 37° C.-10% $CO_2$ incubator overnight. On the day of the experiment, the growth media was replaced with the FluxOR™ reagent loading buffer and incubated, protected from light, at ambient temperature (23-25° C.) for 90 min. The loading buffer was replaced with assay buffer±test compound followed by 30 min incubation at ambient temperature, where the Thallium/Potassium stimulant was added to the microplate.

Step Protocol
1. Seed HEK-hKir1.1 cells (50 µl at 20,000 cells/well) in 384-well PDL coated Microplates
2. Allow cells to adhere overnight in humidified 37° C./10% $CO_2$ incubator
3. Completely remove cell growth media from microplate and replace with 25 µl loading buffer
4. Incubate Microplate at room temperature, protected form light, for 90 min
5. Remove loading buffer and replace with 25 µl 1× Assay Buffer±test compound.
6. Incubate microplate at room temperature, protected from light, for 30 min
7. At FLIPR-Tetra 384: Add stimulant (Thallium/Potassium) solution to microplate and monitor fluorescence. Excitation=400 nm, Emission=460 & 580 nm. Collect data for ~10 min.

Data Calculation—

The fluorescence intensity of wells containing 3 µM of a standard control ROMK inhibitor of the present invention is used to define the ROMK-sensitive component of thallium flux. Fluorescence in the presence of test compounds is normalized to control values to provide % fluorescence change. $IC_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be any compound of Formula I of the present invention, preferably with an $IC_{50}$ potency of less than 1 µM in this assay. Alternatively, the control could be another compound (outside the scope of Formula I) that has an $IC_{50}$ potency in this assay of less than 1 µM.

Data collected for compounds in the Examples of the present invention using the Thallium Flux Assay are shown in Table 3 below. All of the tested final product compounds in the Examples (diastereomeric mixtures and individual diastereomers) had $IC_{50}$ potencies less than 1 µM the Thallium Flux Assay.

TABLE 3

| Example No. | Thallium Flux IC50 (µM) |
| --- | --- |
| 1 | 0.6402 |
| 2 | 0.8422 |
| 3A | 0.3232 |
| 3B | 0.08629 |
| 4 | 0.4737 |
| 5 | 0.0491 |
| 6 | 0.294 |
| 7 | 0.7959 |
| 8 | 0.1674 |
| 9 | 0.1567 |

TABLE 3-continued

| Example No. | Thallium Flux IC50 (μM) |
|---|---|
| 10 | 0.2854 |
| 11 | 0.1216 |
| 12 | 0.5212 |
| 13 | 0.3557 |
| 14 | 0.08695 |
| 15 | 0.05589 |
| 16 | 0.2763 |
| 17 | 0.5985 |
| 18 | 0.04732 |
| 19 | 0.06223 |
| 20 | 0.4974 |
| 21 | 0.1177 |
| 22 | 0.1141 |
| 23 | 0.1869 |
| 24 | 0.3863 |
| 25 | 0.3469 |
| 26 | 0.08714 |
| 27 | 0.07449 |
| 28 | 0.2947 |
| 29 | 0.674 |
| 30 | 0.415 |
| 31 | 0.7511 |
| 32 | 0.6469 |
| 33 | 0.01727 |
| 34 | 0.01091 |
| 35 | 0.1964 |
| 36 | 0.5312 |
| 37 | 0.4611 |
| 38 | 0.08867 |
| 39 | 0.01513 |
| 40 | 0.07147 |
| 41 | 0.01074 |
| 42 | 0.05966 |
| 43 | 0.5684 |
| 44 | 0.1002 |
| 45 | 0.8923 |

What is claimed is:

1. A compound having structural Formula Ia, Formula Ib, Formula Id, Formula Ie, Formula If, or Formula Ig:

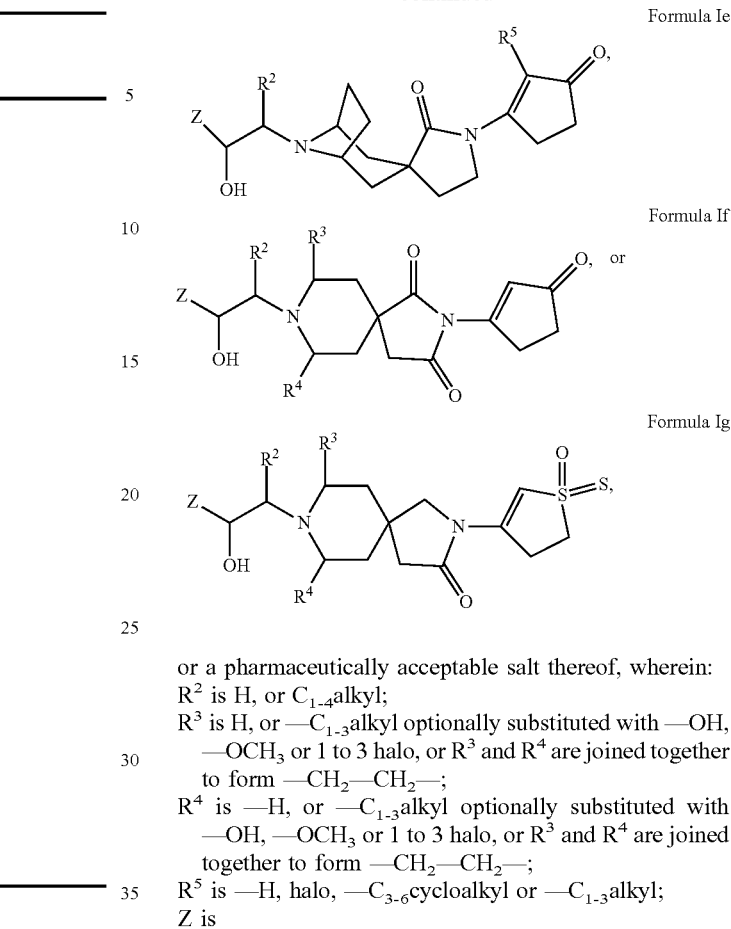

or a pharmaceutically acceptable salt thereof, wherein:

$R^2$ is H, or $C_{1-4}$alkyl;

$R^3$ is H, or —$C_{1-3}$alkyl optionally substituted with —OH, —$OCH_3$ or 1 to 3 halo, or $R^3$ and $R^4$ are joined together to form —$CH_2$—$CH_2$—;

$R^4$ is —H, or —$C_{1-3}$alkyl optionally substituted with —OH, —$OCH_3$ or 1 to 3 halo, or $R^3$ and $R^4$ are joined together to form —$CH_2$—$CH_2$—;

$R^5$ is —H, halo, —$C_{3-6}$cycloalkyl or —$C_{1-3}$alkyl;

Z is

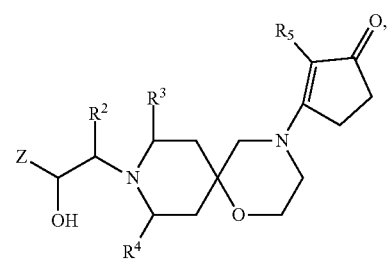

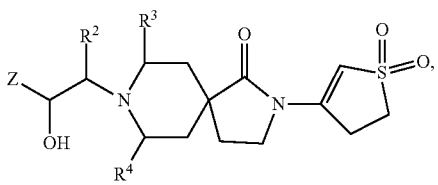

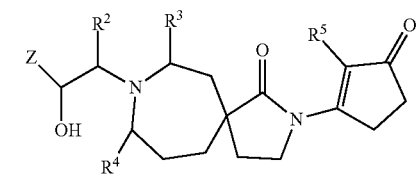

$Y^1$, $Y^2$, $Y^3$ and $Y^4$ are each independently selected from $C(R^9)$ or N;

provided that at most two of $Y^1$, $Y^2$, $Y^3$ and $Y^4$ are N;

each $R^9$ is independently —H, halo, $OC_{1-4}$alkyl or $C_{1-4}$alkyl optionally substituted with 1-3 of halo;

$R^{10}$ is —H, halo, or $C_{1-4}$alkyl optionally substituted with 1-3 halo;

$R^{11}$ is —H, $C_{1-4}$alkyl optionally substituted with 1-3 halo; and $R^{12}$ is —H or $C_{1-4}$alkyl.

2. The compound of claim 1, or a pharmaceutically acceptable salt thereof, wherein each of $R^3$ and $R^4$ are —H, or $R^3$ and $R^4$ are joined together to form —$CH_2CH_2$—.

3. The compound of claim 1, or a pharmaceutically acceptable salt thereof, wherein $R^5$ is —H or —CH$_3$.

4. The compound of claim 1, or a pharmaceutically acceptable salt thereof, wherein $R^5$ is —H.

5. The compound of claim 1, or a pharmaceutically acceptable salt thereof, wherein $R^5$ is —CH$_3$.

6. The compound of claim 1, or a pharmaceutically acceptable salt thereof, wherein Z is

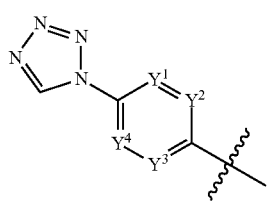

wherein each of the variables $Y^1$, $Y^2$, $Y^3$ and $Y^4$, are as defined in claim 1.

7. The compound of claim 1, or a pharmaceutically acceptable salt thereof, wherein Z is

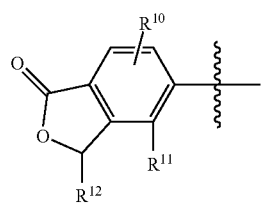

wherein each of the variables $R^{10}$, $R^{11}$, and $R^{12}$ are as defined in claim 1.

8. The compound of claim 1, or a pharmaceutically acceptable salt thereof, wherein Z, if present, is

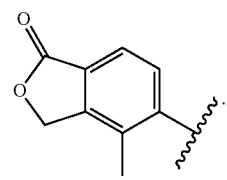 [SMILES: *c1ccc2c(c1C)COC2=O]

9. A compound which is:

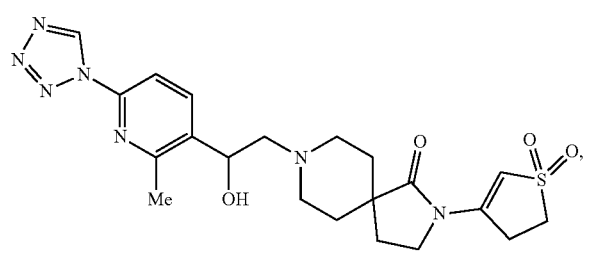

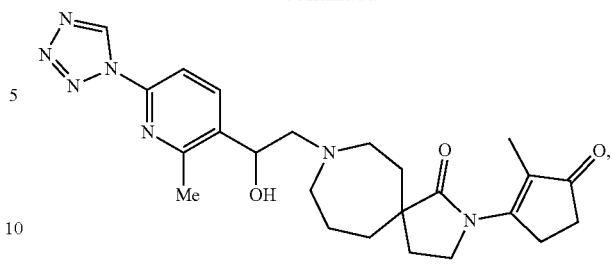

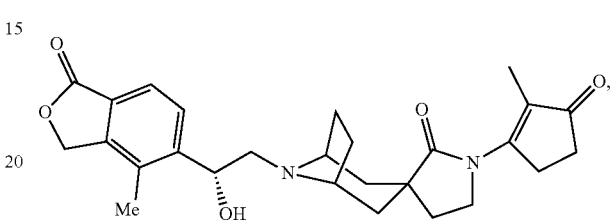

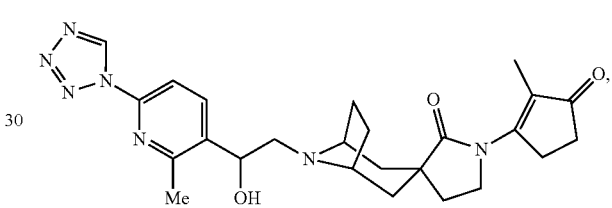

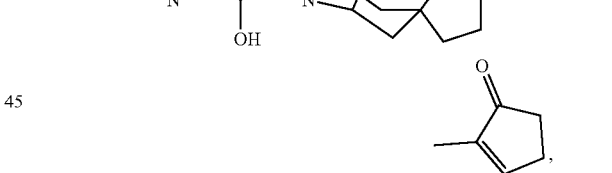

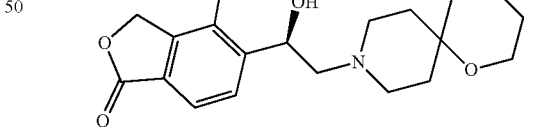

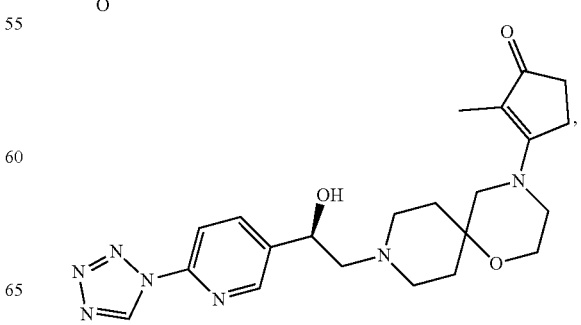

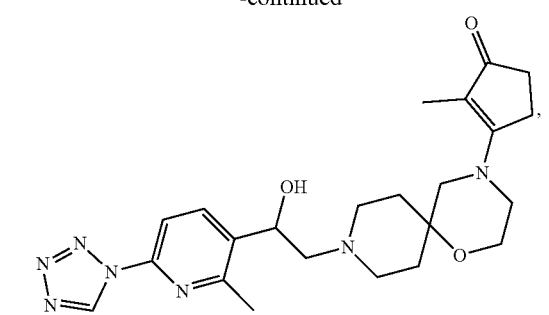
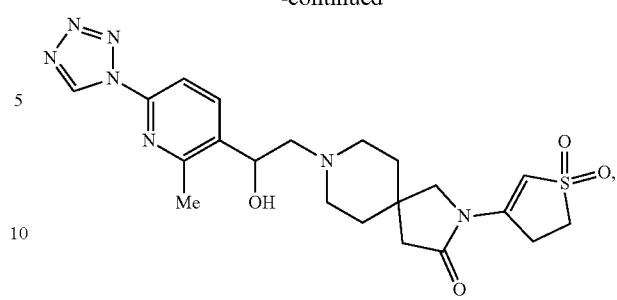
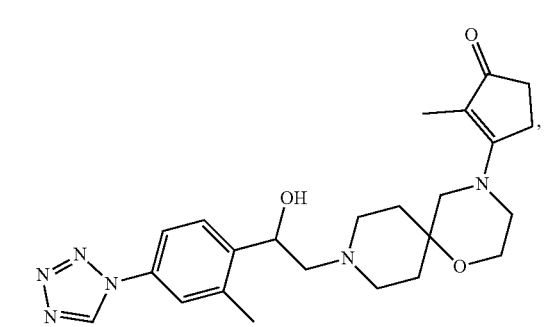
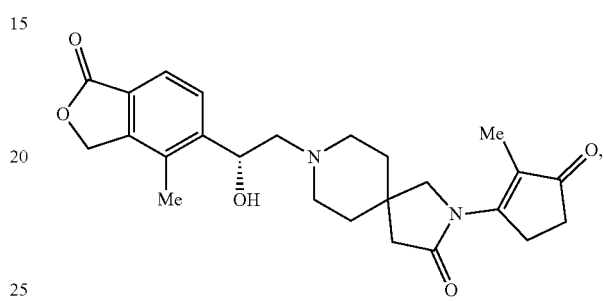
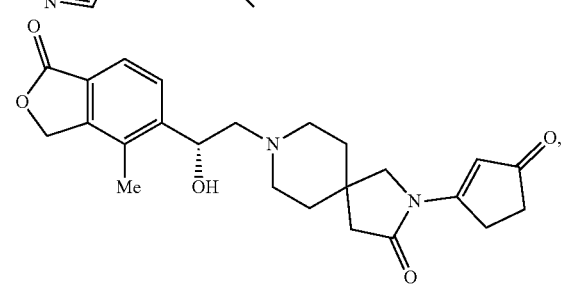
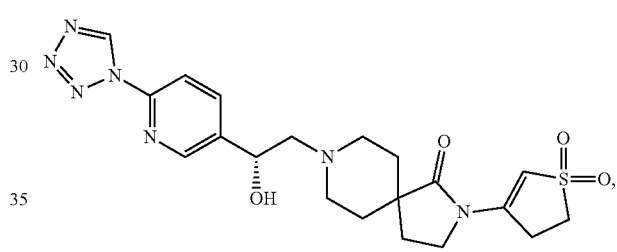
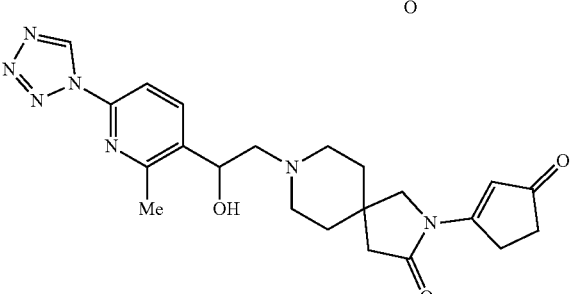
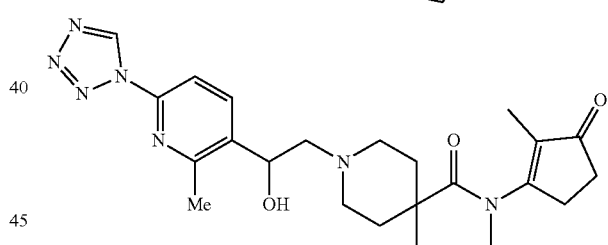
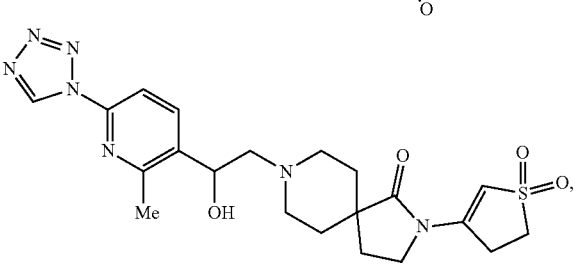
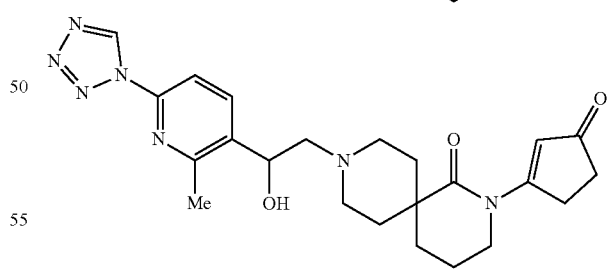
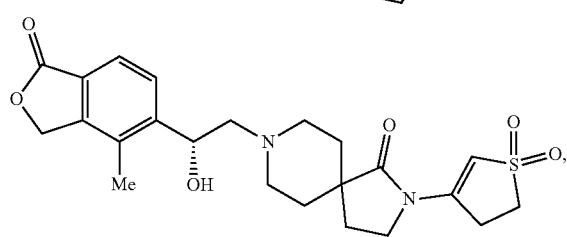
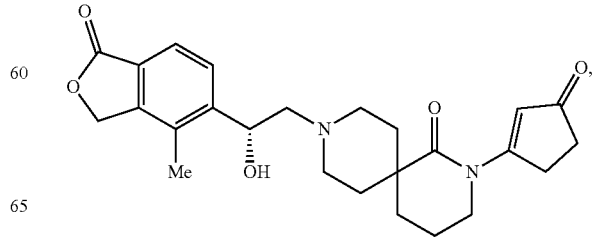

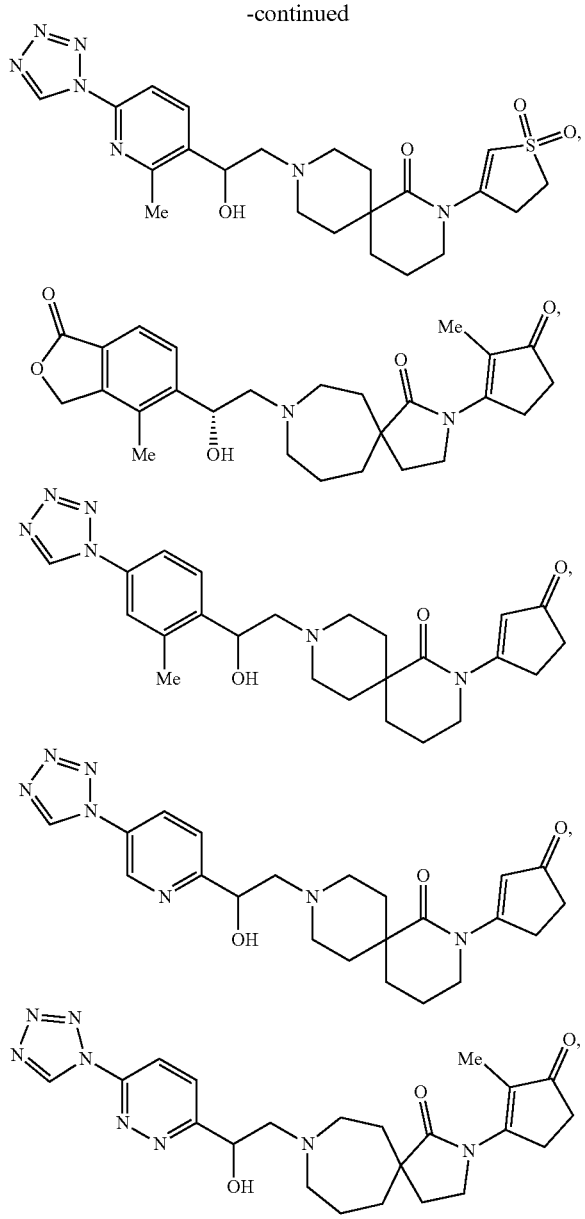

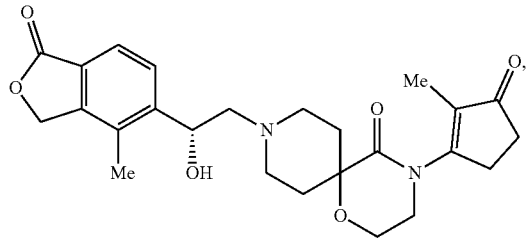

or a pharmaceutically acceptable salt thereof.

10. A pharmaceutical composition comprising a compound of claim 1, or a pharmaceutically acceptable salt thereof, and a pharmaceutically acceptable carrier.

11. The pharmaceutical composition of claim 10, further comprising an additional active agent selected from losartan, valsartan, candesartan, olmesartan, telmesartan, eprosartan, irbesartan, amlodipine, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, trandolapril, amiloride, spironolactone, epleranone or triamterene, or a pro-drug thereof, or a pharmaceutically acceptable salt of any of the foregoing.

12. A method for causing diueresis, natriuresis or both, comprising administering a compound of claim 1 or a pharmaceutically acceptable salt thereof in a therapeutically effective amount to a patient in need thereof.

13. A method for the treatment of one or more disorders selected from hypertension, acute heart failure, chronic heart failure, pulmonary arterial hypertension, cardiovascular disease, diabetes, endothelial dysfunction, diastolic dysfunction, stable and unstable angina pectoris, thromboses, restenosis, myocardial infarction, stroke, cardiac insufficiency, pulmonary hypertonia, atherosclerosis, hepatic cirrhosis, ascitis, pre-eclampsia, cerebral edema, nephropathy, nephrotic syndrome, acute kidney insufficiency, chronic kidney disease, hypercalcemia, Dent's disease, Meniere's disease, or edematous states comprising administering a compound of claim 1 or a pharmaceutically acceptable salt thereof in a therapeutically effective amount to a patient in need thereof.

* * * * *

UNITED STATES PATENT AND TRADEMARK OFFICE
CERTIFICATE OF CORRECTION

PATENT NO. : 10,513,518 B2
APPLICATION NO. : 15/544295
DATED : December 24, 2019
INVENTOR(S) : Reynalda K. deJesus et al.

Page 1 of 1

It is certified that error appears in the above-identified patent and that said Letters Patent is hereby corrected as shown below:

In the Claims

In Claim 1, Column 84, Line 10, replace:

"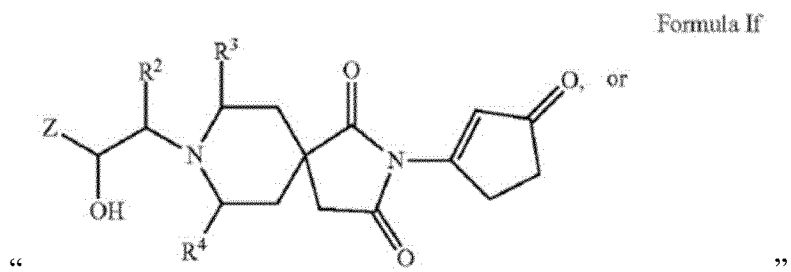"

With:

"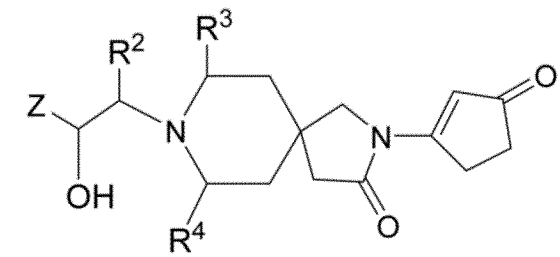"

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*